United States Patent
Törmäkangas et al.

(10) Patent No.: US 8,921,378 B2
(45) Date of Patent: *Dec. 30, 2014

(54) ANDROGEN RECEPTOR MODULATING CARBOXAMIDES

(75) Inventors: Olli Törmäkangas, Turku (FI); Gerd Wohlfahrt, Helsinki (FI); Harri Salo, Turku (FI); Rathna Durga Ramasubramanian, Turku (FI); Pranab Kumar Patra, Noida (IN); Arputharaj Ebenezer Martin, Noida (IN); Terhi Heikkinen, Lieto (FI); Anniina Vesalainen, Paimio (FI); Anu Moilanen, Turku (FI); Arja Karjalainen, Espoo (FI)

(73) Assignee: Orion Corporation, Espoo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 14/112,727

(22) PCT Filed: Apr. 20, 2012

(86) PCT No.: PCT/FI2012/000022
§ 371 (c)(1),
(2), (4) Date: Dec. 18, 2013

(87) PCT Pub. No.: WO2012/143599
PCT Pub. Date: Oct. 26, 2012

(65) Prior Publication Data
US 2014/0094474 A1    Apr. 3, 2014

(30) Foreign Application Priority Data
Apr. 21, 2011  (IN) .................. 570/KOL/2011

(51) Int. Cl.
| | | |
|---|---|---|
| A61K 31/519 | (2006.01) | |
| C07D 231/14 | (2006.01) | |
| C07D 487/04 | (2006.01) | |
| C07D 403/04 | (2006.01) | |
| C07D 471/04 | (2006.01) | |
| C07D 403/14 | (2006.01) | |
| C07D 401/14 | (2006.01) | |
| C07D 403/12 | (2006.01) | |
| C07D 401/04 | (2006.01) | |
| C07D 413/14 | (2006.01) | |
| C07D 413/12 | (2006.01) | |
| C07D 513/04 | (2006.01) | |

(52) U.S. Cl.
CPC ............ *C07D 487/04* (2013.01); *C07D 231/14* (2013.01); *C07D 403/04* (2013.01); *C07D 471/04* (2013.01); *C07D 403/14* (2013.01); *C07D 401/14* (2013.01); *C07D 403/12* (2013.01); *C07D 401/04* (2013.01); *C07D 413/14* (2013.01); *C07D 413/12* (2013.01); *C07D 513/04* (2013.01)
USPC ...................................... 514/259.1

(58) Field of Classification Search
CPC . A61K 31/415; A61K 31/4155; C07D 231/12
USPC ...................................... 514/259.1
See application file for complete search history.

(56) References Cited

U.S. PATENT DOCUMENTS

| | | |
|---|---|---|
| 6,087,509 A | 7/2000 | Claussner et al. |
| 6,673,799 B1 | 1/2004 | Taniguchi et al. |
| 7,271,188 B2 | 9/2007 | Tachibana et al. |
| 2012/0225867 A1 | 9/2012 | Wohlfahrt et al. |

FOREIGN PATENT DOCUMENTS

| | | |
|---|---|---|
| EP | 0 100 172 A1 | 2/1984 |
| EP | 1 790 640 A1 | 5/2007 |
| WO | WO 03/057669 A1 | 7/2003 |
| WO | WO 2004/099188 A1 | 11/2004 |

(Continued)

OTHER PUBLICATIONS

Benckova, M. et al, "Disubstituted Ureas of the 5-R-2-Furylethylene Type," Chemical Papers, 50(3): 148-150 (Jan. 1, 1996).

(Continued)

*Primary Examiner* — Rei-Tsang Shiao
*Assistant Examiner* — Christopher R Stone
(74) *Attorney, Agent, or Firm* — Finnegan, Henderson, Farabow, Garrett & Dunner, LLP

(57) ABSTRACT

Compounds of formula (I) or (II)

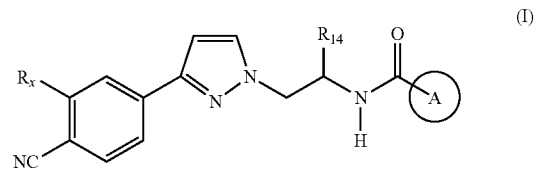

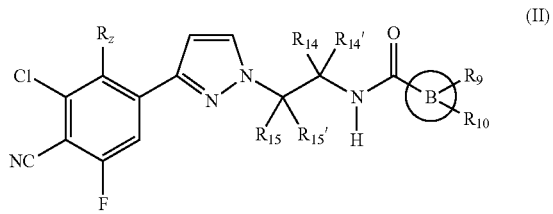

wherein $R_x$, $R_z$, $R_9$, $R_{10}$, $R_{14}$, $R_{14}'$, $R_{15}$, $R_{15}'$, A and B are as defined in the claims and pharmaceutically acceptable salts and esters thereof, are disclosed. The compounds possess utility as tissue-selective androgen receptor modulators (SARM) and are useful as medicaments in the treatment of prostate cancer and other AR dependent conditions and diseases where AR antagonism is desired.

12 Claims, No Drawings

(56) References Cited

FOREIGN PATENT DOCUMENTS

| WO | WO 2006/124118 A1 | 11/2006 |
| WO | WO 2006/133567 A1 | 12/2006 |
| WO | WO 2007/029035 | 3/2007 |
| WO | WO 2007/056155 | 5/2007 |
| WO | WO 2008/062878 | 5/2008 |
| WO | WO 2008/124000 | 10/2008 |
| WO | WO 2009/028543 A1 | 3/2009 |
| WO | WO 2009/055053 A2 | 4/2009 |
| WO | WO 2011/051540 | 5/2011 |

OTHER PUBLICATIONS

Database Registry, Chemical Abstracts Service, N-[2-(2,5-dimethyl-1-phenyl-1H-pyrrol-3-yl)ethyl]-4-phenyl-1-piperazinecarboxamide, XP002623901 (Mar. 2, 2007).

Database Registry, Chemical Abstracts Service, 1-cycloheptyl-N-[2-[3-(2-methylphenyl)-1-pyrrolidinyl]ethyl]-1H-1,2,3-Triazole-4-carboxamide, XP002623902 (Nov. 2, 2008).

Database Registry, Chemical Abstracts Service, N-[2-[5-(2-nitrophenyl)-2-furanyl]ethenyl]-4-morpholinecarboxamide, XP002623903 (Aug. 28, 2001).

English Abstract for WO 2008/062878, Basic Derwent Week: 200867 (2012).

International Search Report for International Application No. PCT/FI2010/000065, mailed Mar. 17, 2011.

Narayanan, R. et al, "Selective androgen receptor modulators in preclinical and ciinical development," Nuclear Receptor Signaling, 6:1-26 (2008).

Copending U.S. Appl. No. 13/504,511.

Office Action dated Nov. 27, 2013, from copending U.S. Appl. No. 13/504,511.

ANDROGEN RECEPTOR MODULATING CARBOXAMIDES

This is a national stage application under §371 of International Application No. PCT/FI2012/000022, filed on Apr. 20, 2012, which claims the benefit of priority of Indian Patent Application No. 570/KOL/2011, filed Apr. 21, 2011.

TECHNICAL FIELD

The present invention relates to therapeutically active compounds and pharmaceutically acceptable salts and esters thereof useful in the treatment of nuclear receptor, especially steroid receptor, and in particular androgen receptor (AR) dependent conditions and diseases, and to pharmaceutical compositions containing such compounds. In particular, the invention discloses non-steroidal carboxamide and structured compounds having utility as tissue-selective androgen receptor modulators (SARM). The compounds of the invention, which possess AR antagonist activity, are useful for treating patients requiring androgen receptor antagonist therapy. In particular, AR antagonists of the invention are useful in the treatment or prevention of cancer, particularly AR dependent cancer such as prostate cancer, and other diseases where AR antagonism is desired.

BACKGROUND OF THE INVENTION

In recent years, there has been growing interest in the development of nonsteroidal modulators for steroid receptors for therapeutical use. It has been shown that nonsteroidal ligands can achieve better receptor selectivity and better physicochemical, pharmacokinetic and pharmacological properties. For androgen receptor (AR), nonsteroidal antagonists (antiandrogens) are now used clinically to counteract the undesirable actions of excessive androgens.

Androgens, functioning through the AR, are essential for the initiation and progression of prostate cancer. Thus, treatment of advanced prostate cancer involves androgen-ablation therapies, such as surgical castration or hormonal manipulation using gonadotropin-releasing hormone (GnRH) agonists, anti-androgens or both. Although such therapies initially lead to disease regression, eventually all patients progress to a castration resistant late stage that is refractory to current therapies. Castration-resistant prostate cancer (CRPC) is associated with increased levels of AR. First generation anti-androgens such as bicalutamide display agonistic properties in cells engineered to express higher AR levels. In vitro and in vivo, increased AR expression has been shown to confer resistance of prostate cancer cell lines to anti-androgen therapy. To overcome resistance problems, second generation anti-androgens that retain antagonism in cells expressing excess AR may have utility in the treatment of CRPC.

Non-steroidal androgen receptor antagonists have been described earlier e.g. in patent publications EP 100172, EP 1790640, U.S. Pat. No. 6,087,509, U.S. Pat. No. 6,673,799, U.S. Pat. No. 7,271,188, WO 03/057669, WO 2004/099188, WO 2006/133567, WO 2008/124000, WO 2009/028543 and WO 2009/055053.

Related carboxamide structured compounds have been described in WO 2008/062878.

SUMMARY OF THE INVENTION

It has been found that compounds of formula (I) or (II) are potent androgen receptor (AR) modulators, in particular AR antagonists. Compounds of formula (I) or (II) show remarkably high affinity and strong antagonistic activity in androgen receptor. Also in cells which overexpress AR ("AR overexpressing cells") the compounds of the invention possess from high to full AR antagonism while exhibiting only minimal agonism. The compounds of the invention also effectively inhibited proliferation of prostatic cancer cell line. Moreover, the compounds of the invention have low potential for drug-drug interactions, high selectivity to androgen receptor, favourable safety profile and sufficient water solubility.

The compounds of the invention are therefore particularly useful as medicaments in the treatment of prostate cancer and other AR dependent conditions and diseases where AR antagonism is desired.

The present invention provides novel carboxamide structured compounds of formula (I) or (II)

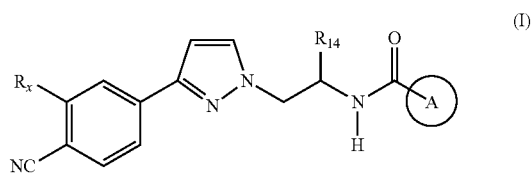

(I)

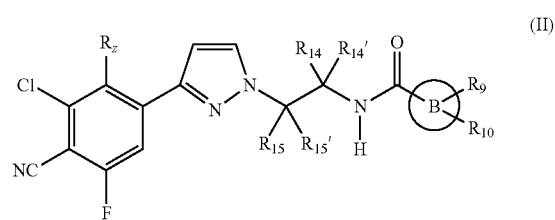

(II)

wherein ring A is any one of the following groups or tautomers thereof

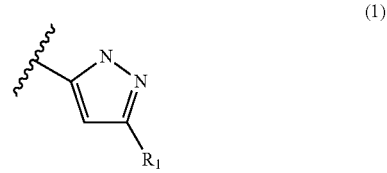

(1)

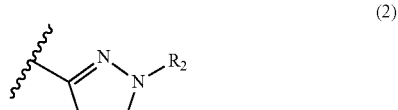

(2)

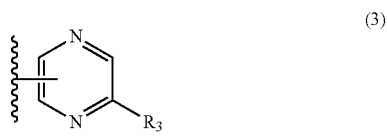

(3)

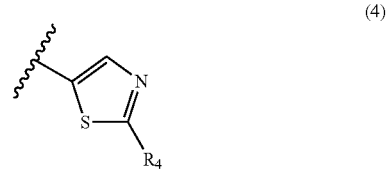

(4)

-continued (5)
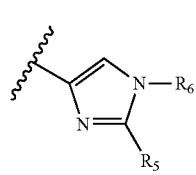

(6)
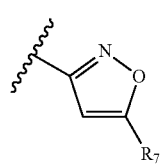

(7)
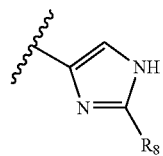

(8)
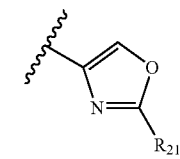

(9)
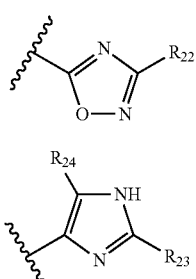

(10)
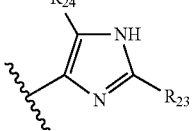

wherein $R_X$ is halogen or $CF_3$;

$R_Z$ is hydrogen or halogen;

$R_1$ is hydroxy $C_{3-7}$ alkyl, imidazolyl or —$R_A$—OC(O)—$R_B$;

$R_A$ is $C_{1-7}$ alkyl;

$R_B$ is $C_{1-7}$ alkyl, hydroxy $C_{1-7}$ alkyl or carboxy $C_{1-7}$ alkyl;

$R_2$ is $C_{1-7}$ alkyl, $C_{2-7}$ alkenyl, $C_{3-7}$ cycloalkyl, $C_{3-7}$ cycloalkyl $C_{1-7}$ alkyl, methylpyrazolyl or pyrimidinyl;

$R_3$ is halogen or pyridinyl;

$R_4$ is pyridinyl;

$R_5$ is $C_{1-7}$ alkyl, $C_{2-7}$ alkenyl, $C_{3-7}$ cycloalkyl, $C_{3-7}$ cycloalkyl $C_{1-7}$ alkyl, cyano, hydroxy $C_{1-7}$ alkyl, oxo $C_{1-7}$ alkyl, halogen or methylpyrazolyl;

$R_6$ is $C_{1-7}$ alkyl, $C_{2-7}$ alkenyl, $C_{3-7}$ cycloalkyl, $C_{3-7}$ cycloalkyl $C_{1-7}$ alkyl, hydroxy, hydroxy $C_{1-7}$ alkyl, cyano $C_{1-7}$ alkyl or $C_{1-7}$ alkoxycarbamoyl $C_{1-7}$ alkyl;

$R_7$ is hydroxy $C_4$ alkyl;

$R_8$ is halogen, $C_{2-7}$ alkyl, $C_{2-7}$ alkenyl, $C_{3-7}$ cycloalkyl, $C_{3-7}$ cycloalkyl $C_{1-7}$ alkyl, cyano, carboxy, oxo $C_{1-7}$ alkyl, halo $C_{1-7}$ alkyl, hydroxy $C_{1-7}$ alkyl, tetrahydro-2H-thiopyran or —C(O)—$NHR_{20}$;

$R_9$ is hydrogen, hydroxy, halogen, nitro, amino, cyano, oxo, $C_{1-7}$ alkyl, $C_{2-7}$ alkenyl, $C_{3-7}$ cycloalkyl, $C_{1-7}$ alkoxy, halo $C_{1-7}$ alkyl, hydroxy $C_{1-7}$ alkyl, cyano $C_{1-7}$ alkyl, amino $C_{1-7}$ alkyl, oxo $C_{1-7}$ alkyl, $C_{1-7}$ alkoxy $C_{1-7}$ alkyl, $C_{1-7}$ alkylamino, hydroxy $C_{1-7}$ alkylamino, $C_{1-7}$ alkoxy $C_{1-7}$ alkylamino, $C_{1-7}$ alkylamino $C_{1-7}$ alkyl, hydroxy $C_{1-7}$ alkylamino $C_{1-7}$ alkyl, hydroxyimino $C_{1-7}$ alkyl, $C_{1-7}$ alkoxycarbamoyl $C_{1-7}$ alkyl, —C(O)$R_{11}$, —OC(O)$R_{17}$, —NH—C(O)$R_{18}$—NH—$SO_2$—$R_{19}$ or an optionally substituted 5-12 membered carbocyclic or heterocyclic ring, each group linked to B-ring via a bond or via a $C_{1-7}$ alkylene linker;

$R_{10}$ is hydrogen, halogen, $C_{1-7}$ alkyl, $C_{2-7}$ alkenyl, $C_{3-7}$ cycloalkyl, $C_{3-7}$ cycloalkyl $C_{1-7}$ alkyl, oxo, hydroxy $C_{1-7}$ alkyl, oxo $C_{1-7}$ alkyl or an optionally substituted 5 or 6 membered carbocyclic or heterocyclic ring;

$R_{11}$ is hydrogen, hydroxy, $C_{1-7}$ alkyl, hydroxy $C_{1-7}$ alkyl, $C_{2-7}$ alkenyl, $C_{3-7}$ cycloalkyl, halo $C_{1-7}$ alkyl, $C_{1-7}$ alkoxy, $NR_{12}R_{13}$, or an optionally substituted 5-12 membered carbocyclic or heterocyclic ring;

$R_{12}$ is hydrogen, $C_{1-7}$ alkyl, $C_{2-7}$ alkenyl, $C_{3-7}$ cycloalkyl, $C_{3-7}$ cycloalkyl $C_{1-7}$ alkyl, $C_{1-7}$ alkoxy, hydroxy $C_{1-7}$ alkyl, amino $C_{1-7}$ alkyl or $C_{1-7}$ alkyl amino $C_{1-7}$ alkyl;

$R_{13}$ is hydrogen or $C_{1-7}$ alkyl;

$R_{14}$ and $R_{15}$ are, independently, hydrogen or $C_{1-7}$ alkyl;

$R_{14}'$ and $R_{15}'$ are, independently, hydrogen or $C_{1-7}$ alkyl, or $R_{14}'$ and $R_{15}'$ together form a bond;

$R_{17}$ is $C_{1-7}$ alkyl, $C_{2-7}$ alkenyl, $C_{3-7}$ cycloalkyl, $C_{3-7}$ cycloalkyl $C_{1-7}$ alkyl, $C_{1-7}$ alkoxy, amino $C_{1-7}$ alkyl, $C_{1-7}$ alkylamino or $C_{1-7}$ alkylamino $C_{1-7}$ alkyl;

$R_{18}$ is $C_{1-7}$ alkyl, $C_{2-7}$ alkenyl, $C_{3-7}$ cycloalkyl, $C_{3-7}$ cycloalkyl $C_{1-7}$ alkyl, amino $C_{1-7}$ alkyl, $C_{1-7}$ alkylamino or $C_{1-7}$ alkylamino $C_{1-7}$ alkyl;

$R_{19}$ is $C_{1-7}$ alkyl, $C_{2-7}$ alkenyl, $C_{3-7}$ cycloalkyl or $C_{3-7}$ cycloalkyl $C_{1-7}$ alkyl;

$R_{20}$ is hydrogen, $C_{1-7}$ alkyl, $C_{2-7}$ alkenyl, $C_{3-7}$ cycloalkyl, $C_{3-7}$ cycloalkyl $C_{1-7}$ alkyl or $C_{1-7}$ alkoxy;

$R_{21}$ is cyano $C_{1-7}$ alkyl or, in case $R_X$ is $CF_3$, $R_{21}$ can also be hydroxy $C_{1-7}$ alkyl;

$R_{22}$ is hydroxy $C_{1-7}$ alkyl;

$R_{23}$ is $C_{1-7}$ alkyl or hydroxy $C_{1-7}$ alkyl;

$R_{24}$ is hydroxy, halogen or $C_{1-7}$ alkoxy;

ring B is any one of the following groups or tautomers thereof (1')
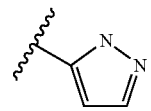

(2')
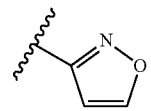

(3')
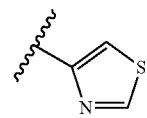

(4')
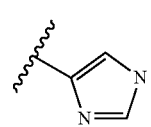

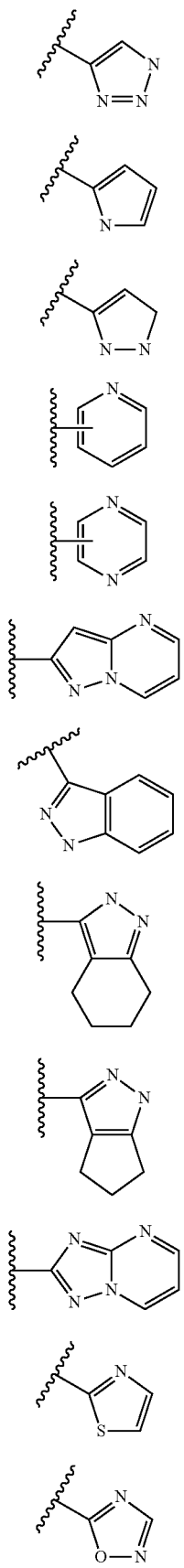
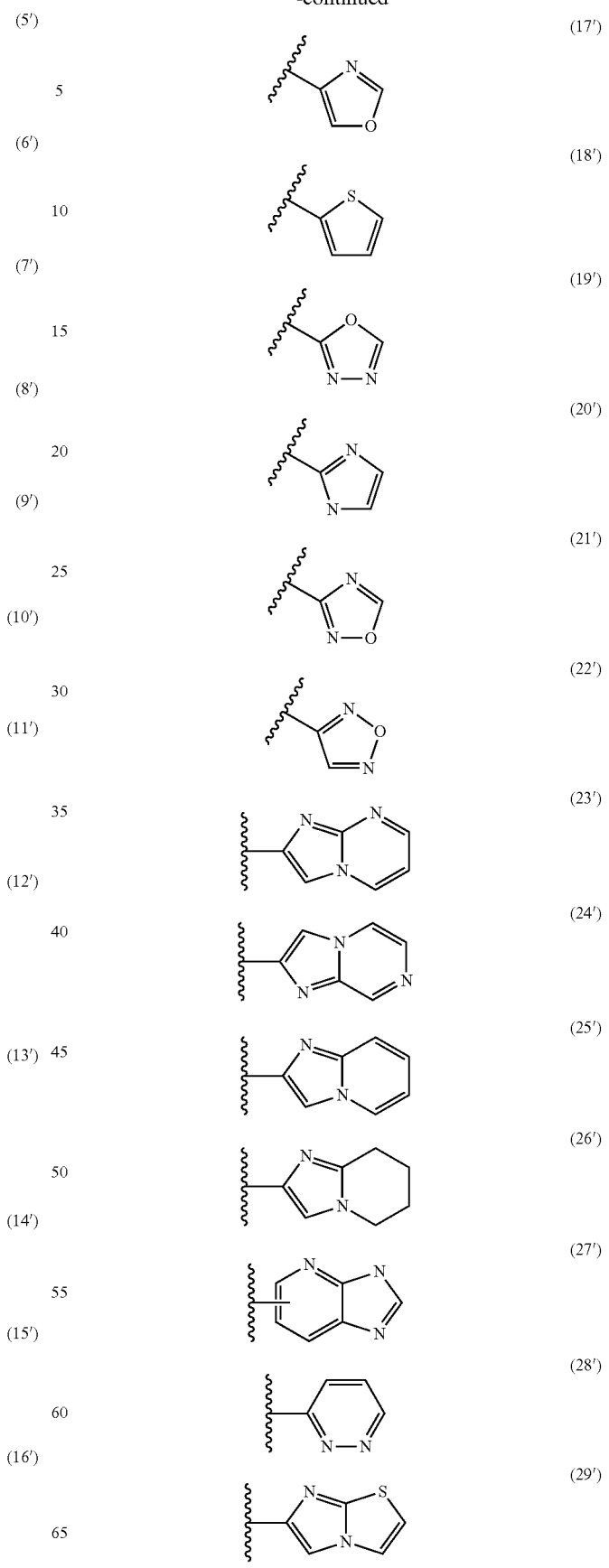

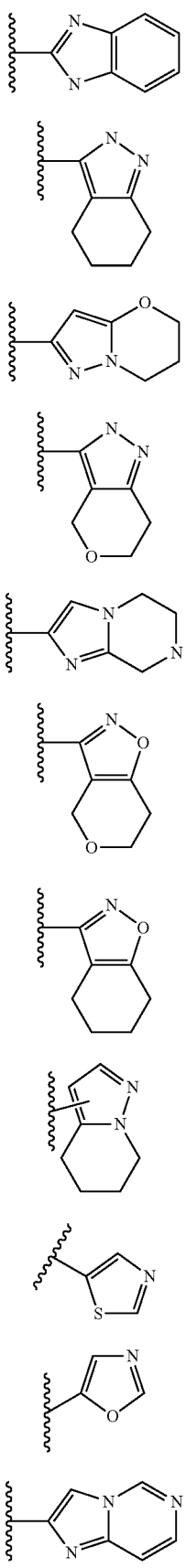
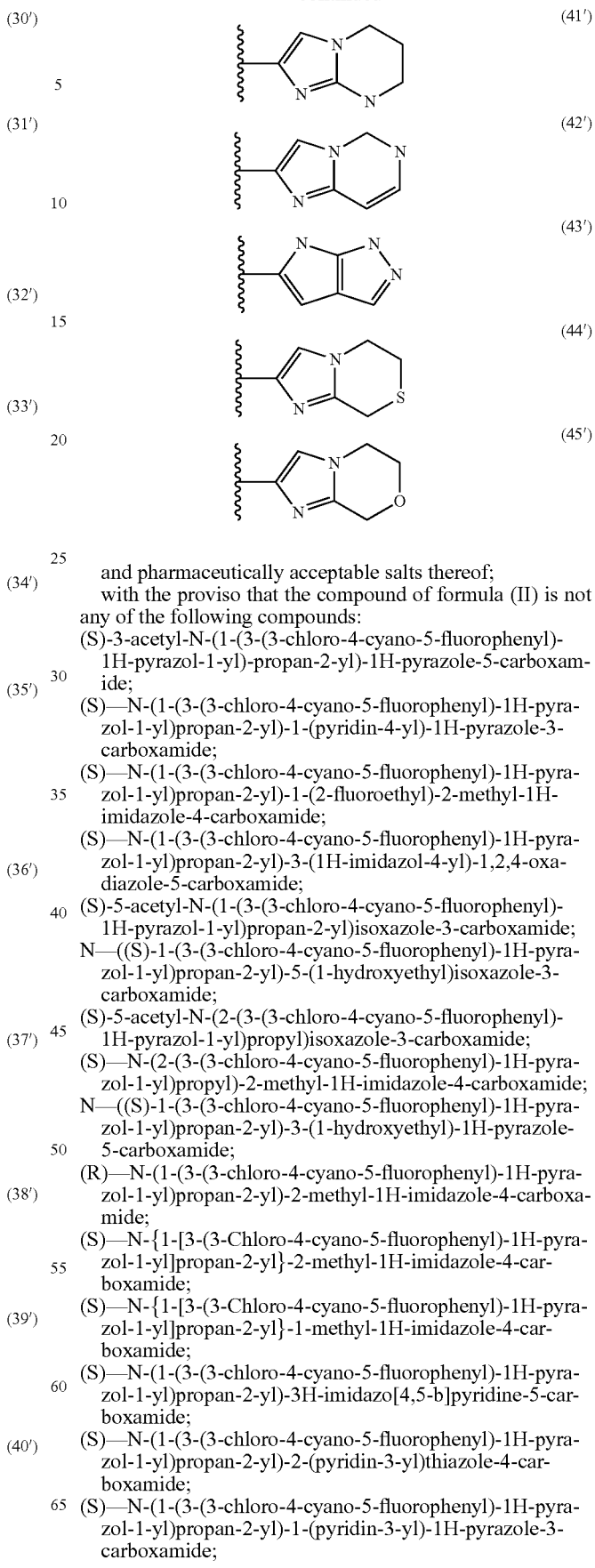

and pharmaceutically acceptable salts thereof;
with the proviso that the compound of formula (II) is not any of the following compounds:
(S)-3-acetyl-N-(1-(3-(3-chloro-4-cyano-5-fluorophenyl)-1H-pyrazol-1-yl)-propan-2-yl)-1H-pyrazole-5-carboxamide;
(S)—N-(1-(3-(3-chloro-4-cyano-5-fluorophenyl)-1H-pyrazol-1-yl)propan-2-yl)-1-(pyridin-4-yl)-1H-pyrazole-3-carboxamide;
(S)—N-(1-(3-(3-chloro-4-cyano-5-fluorophenyl)-1H-pyrazol-1-yl)propan-2-yl)-1-(2-fluoroethyl)-2-methyl-1H-imidazole-4-carboxamide;
(S)—N-(1-(3-(3-chloro-4-cyano-5-fluorophenyl)-1H-pyrazol-1-yl)propan-2-yl)-3-(1H-imidazol-4-yl)-1,2,4-oxadiazole-5-carboxamide;
(S)-5-acetyl-N-(1-(3-(3-chloro-4-cyano-5-fluorophenyl)-1H-pyrazol-1-yl)propan-2-yl)isoxazole-3-carboxamide;
N—((S)-1-(3-(3-chloro-4-cyano-5-fluorophenyl)-1H-pyrazol-1-yl)propan-2-yl)-5-(1-hydroxyethyl)isoxazole-3-carboxamide;
(S)-5-acetyl-N-(2-(3-(3-chloro-4-cyano-5-fluorophenyl)-1H-pyrazol-1-yl)propyl)isoxazole-3-carboxamide;
(S)—N-(2-(3-(3-chloro-4-cyano-5-fluorophenyl)-1H-pyrazol-1-yl)propyl)-2-methyl-1H-imidazole-4-carboxamide;
N—((S)-1-(3-(3-chloro-4-cyano-5-fluorophenyl)-1H-pyrazol-1-yl)propan-2-yl)-3-(1-hydroxyethyl)-1H-pyrazole-5-carboxamide;
(R)—N-(1-(3-(3-chloro-4-cyano-5-fluorophenyl)-1H-pyrazol-1-yl)propan-2-yl)-2-methyl-1H-imidazole-4-carboxamide;
(S)—N-{1-[3-(3-Chloro-4-cyano-5-fluorophenyl)-1H-pyrazol-1-yl]propan-2-yl}-2-methyl-1H-imidazole-4-carboxamide;
(S)—N-{1-[3-(3-Chloro-4-cyano-5-fluorophenyl)-1H-pyrazol-1-yl]propan-2-yl}-1-methyl-1H-imidazole-4-carboxamide;
(S)—N-(1-(3-(3-chloro-4-cyano-5-fluorophenyl)-1H-pyrazol-1-yl)propan-2-yl)-3H-imidazo[4,5-b]pyridine-5-carboxamide;
(S)—N-(1-(3-(3-chloro-4-cyano-5-fluorophenyl)-1H-pyrazol-1-yl)propan-2-yl)-2-(pyridin-3-yl)thiazole-4-carboxamide;
(S)—N-(1-(3-(3-chloro-4-cyano-5-fluorophenyl)-1H-pyrazol-1-yl)propan-2-yl)-1-(pyridin-3-yl)-1H-pyrazole-3-carboxamide;

(S)—N-(1-(3-(3-chloro-4-cyano-5-fluorophenyl)-1H-pyrazol-1-yl)propan-2-yl)-2-methyl-1-(3-oxobutyl)-1H-imidazole-4-carboxamide;
(S)—N-(1-(3-(3-chloro-4-cyano-5-fluorophenyl)-1H-pyrazol-1-yl)propan-2-yl)-1-(3-hydroxy-3-methylbutyl)-2-methyl-1H-imidazole-4-carboxamide;
(S)—N-(1-(3-(3-chloro-4-cyano-5-fluorophenyl)-1H-pyrazol-1-yl)propan-2-yl)imidazo[1,2-a]pyridine-2-carboxamide;
(S)—N-(1-(3-(3-chloro-4-cyano-5-fluorophenyl)-1H-pyrazol-1-yl)propan-2-yl)-1-(pyridin-3-yl)-1H-imidazole-4-carboxamide;
(S)—N-(1-(3-(3-chloro-4-cyano-5-fluorophenyl)-1H-pyrazol-1-yl)propan-2-yl)-2-(2-hydroxypropan-2-yl)oxazole-4-carboxamide;
(S)—N-(1-(3-(3-chloro-4-cyano-5-fluorophenyl)-1H-pyrazol-1-yl)propan-2-yl)imidazo[1,2-a]pyrimidine-2-carboxamide;
(S)—N-(1-(3-(3-chloro-4-cyano-5-fluorophenyl)-1H-pyrazol-1-yl)propan-2-yl)-3-fluoroimidazo pyridine-2-carboxamide;
(S)—N-(1-(3-(3-chloro-4-cyano-5-fluorophenyl)-1H-pyrazol-1-yl)propan-2-yl)-4,5,6,7-tetrahydro-2H-indazole-3-carboxamide;
(S)—N-(1-(3-(3-chloro-4-cyano-5-fluorophenyl)-1H-pyrazol-1-yl)propan-2-yl)-6,7-dihydro-5H-pyrazolo[5,1-b][1,3]oxazine-2-carboxamide;
(S)—N-(1-(3-(3-chloro-4-cyano-5-fluorophenyl)-1H-pyrazol-1-yl)propan-2-yl)-2,4,6,7-tetrahydropyrano[4,3-c]pyrazole-3-carboxamide;
(S)—N-(1-(3-(3-chloro-4-cyano-5-fluorophenyl)-1H-pyrazol-1-yl)propan-2-yl)-1-(6-methylpyridin-2-yl)-1H-imidazole-4-carboxamide;
(S)—N-(1-(3-(3-chloro-4-cyano-5-fluorophenyl)-1H-pyrazol-1-yl)propan-2-yl)-6,7-dihydro-4H-pyrano[3,4-d]isoxazole-3-carboxamide;
(S)—N-(1-(3-(3-chloro-4-cyano-5-fluorophenyl)-1H-pyrazol-1-yl)propan-2-yl)-5-(2-hydroxypropan-2-yl)isoxazole-3-carboxamide.

It is to be understood that each B-ring (1') to (45') above are substituted by $R_9$ and $R_{10}$ as shown in formula (II).

In a subclass of compounds of formula (I) or (II) are compounds of formula (I') or (II') and pharmaceutically acceptable salts thereof, wherein $R_x$, $R_z$, $R_9$, $R_{10}$, A and B are as defined above.

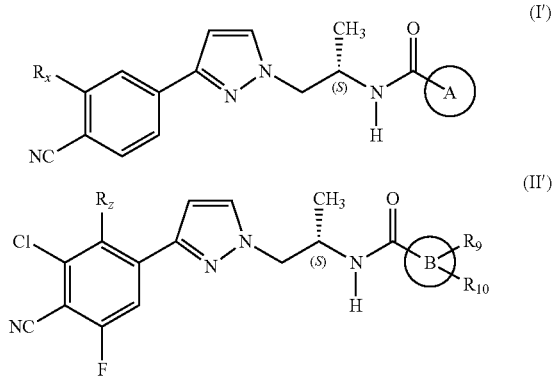

In a subclass of preferred compounds of formula (I) or (I') are compounds and pharmaceutically acceptable salts thereof wherein $R_x$ is halogen, $R_{14}$ is $C_{1-7}$ alkyl, and ring A is any of groups (1), (2), (3), (5), (6), (7) or (8). A further subclass of preferred compounds formula (I) or (I') are compounds and pharmaceutically acceptable salts thereof wherein $R_x$ is chloro, $R_{14}$ is methyl, and ring A is any of groups (1), (2), (5), (6) or (7), $R_1$ is hydroxy $C_{3-7}$ alkyl, imidazolyl or carboxy $C_{1-7}$ alkyl carbonyloxy $C_{1-7}$ alkyl, $R_2$ is $C_{1-7}$ alkyl, $C_{2-7}$ alkenyl or methylpyrazolyl, $R_5$ is $C_{1-7}$ alkyl, $C_{3-7}$ cycloalkyl, hydroxy $C_{1-7}$ alkyl or methylpyrazolyl, $R_6$ is $C_{1-7}$ alkyl, cyano $C_{1-7}$ alkyl or hydroxy $C_{1-7}$ alkyl and $R_8$ is $C_{1-7}$ alkyl, halogen, oxo $C_{1-7}$ alkyl or hydroxy $C_{1-7}$ alkyl.

In a subclass of preferred compounds of formula (II) or (II') are compounds and pharmaceutically acceptable salts thereof wherein $R_{14}$ is $C_{1-7}$ alkyl, $R_{14}'$, $R_{15}$ and $R_{15}'$ is hydrogen, ring B is any of groups (1'), (2'), (3'), (4'), (8'), (16'), (17'), (21'), (23'), (24'), (25'), (26'), (29'), (39'), (40'), (42') or (43'), $R_9$ is hydrogen, halogen, cyano, oxo, $C_{1-7}$ alkyl, $C_{2-7}$ alkenyl, $C_{3-7}$ cycloalkyl, halo $C_{1-7}$ alkyl, cyano $C_{1-7}$ alkyl, hydroxy $C_{1-7}$ alkyl, oxo $C_{1-7}$ alkyl, —NH—SO$_2$—R$_{19}$ or an optionally substituted 5-12 membered heterocyclic ring, each $R_9$ group linked to B-ring via a bond or via a $C_{1-7}$ alkylene linker, $R_{10}$ is hydrogen, $C_{1-7}$ alkyl or $C_{3-7}$ cycloalkyl, and $R_{19}$ is $C_{1-7}$ alkyl. Particularly preferred 5-12 membered heterocyclic ring in $R_9$ is pyrazole, pyridine, isoxazole or imidazole ring, which is attached to B-ring via a bond or via $C_{1-7}$ alkylene linker. Particularly preferred substituents in the 5-12 membered heterocyclic ring in $R_9$ are 1 to 3 substituents selected from $C_{1-7}$ alkyl, $C_{3-7}$ cycloalkyl, halogen or hydroxy $C_{1-7}$ alkyl groups.

Still another class of preferred compounds are compounds of formula (II) or (II') and pharmaceutically acceptable salts thereof wherein $R_z$ is hydrogen or fluoro, $R_{14}$ is methyl, $R_{14}'$, $R_{15}$ and $R_{15}'$ is hydrogen, ring B is any of groups (1'), (2'), (4'), (17'), (21') or (25'), $R_9$ is hydrogen, halogen, cyano, oxo, $C_{1-7}$ alkyl, $C_{2-7}$ alkenyl, $C_{3-7}$ cycloalkyl, halo $C_{1-7}$ alkyl, hydroxy $C_{1-3}$ alkyl, cyano $C_{1-7}$ alkyl, pyrazolyl, N-methyl pyrazolyl, pyridinyl, isoxazolyl, imidazolyl or imidazolyl methyl, and $R_{10}$ is hydrogen, $C_{1-7}$ alkyl or $C_{3-7}$ cycloalkyl.

The present invention provides further a method for the treatment or prevention of androgen receptor (AR) dependent conditions, comprising administering to a subject in need thereof a therapeutically effective amount of a compound of formula (I) or (II) or pharmaceutically acceptable salts thereof. For example, the AR dependent condition to be treated is cancer, particularly AR dependent cancer such as prostate cancer, benign prostatic hyperplasia, androgenic alopecia and acne. According to one embodiment of the invention, the AR dependent condition to be treated is castration-resistant prostate cancer (CRPC).

The present invention also provides a pharmaceutical composition comprising a compound of formula (I) or (II) or pharmaceutically acceptable salts thereof together with a pharmaceutically acceptable carrier.

DETAILED DESCRIPTION OF THE INVENTION

The compounds of the invention can be prepared by a variety of synthetic routes analogously to the methods known in the literature using suitable starting materials. For example, compounds of formula (I) or (II) can be prepared according to the reaction Scheme 1, wherein $R_z$, $R_{14}$, $R_{14}'$, $R_{15}$, $R_{15}'$, B, $R_9$, and $R_{10}$ are as defined above and X is a halogen. Preparation of compounds of formula (II) is shown in Schemes 1 and 2, but compounds of formula (I) can be prepared in analogous manner following the methods of Schemes 1 and 2. Optically active enantiomers or diastereomers of compounds of formula (I) or (II) can be prepared e.g. by using suitable optically active starting materials. Similarly, racemic compounds of formula (I) or (II) can be prepared by using racemic starting materials. Some compounds included in the formula (I) or (II) can be obtained by converting the functional groups of the other compounds of formula (I) or (II) obtained in accordance with Scheme 1, by well known reaction steps such as oxidation, reduction, hydrolysis, acylation, alkylation, amidation, amination and others.

SCHEME 1
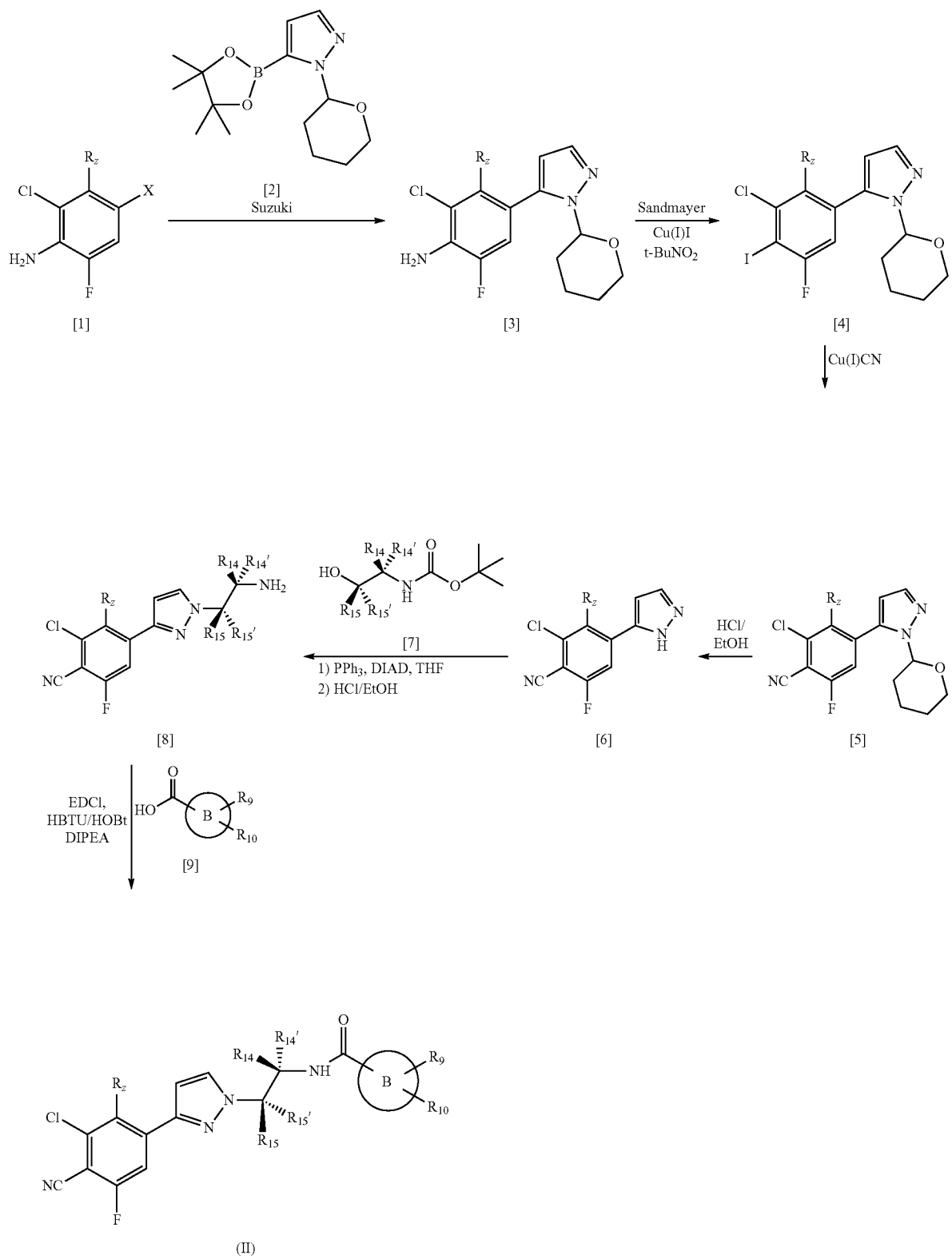
Alternatively, compounds of formula (I) or (II) can be prepared according to the Scheme 2. $R_z$, $R_{14}$, $R_{14}'$, $R_{15}$, $R_{15}'$, B, $R_9$, and $R_{10}$ are as defined above and X is a halogen.

SCHEME 2

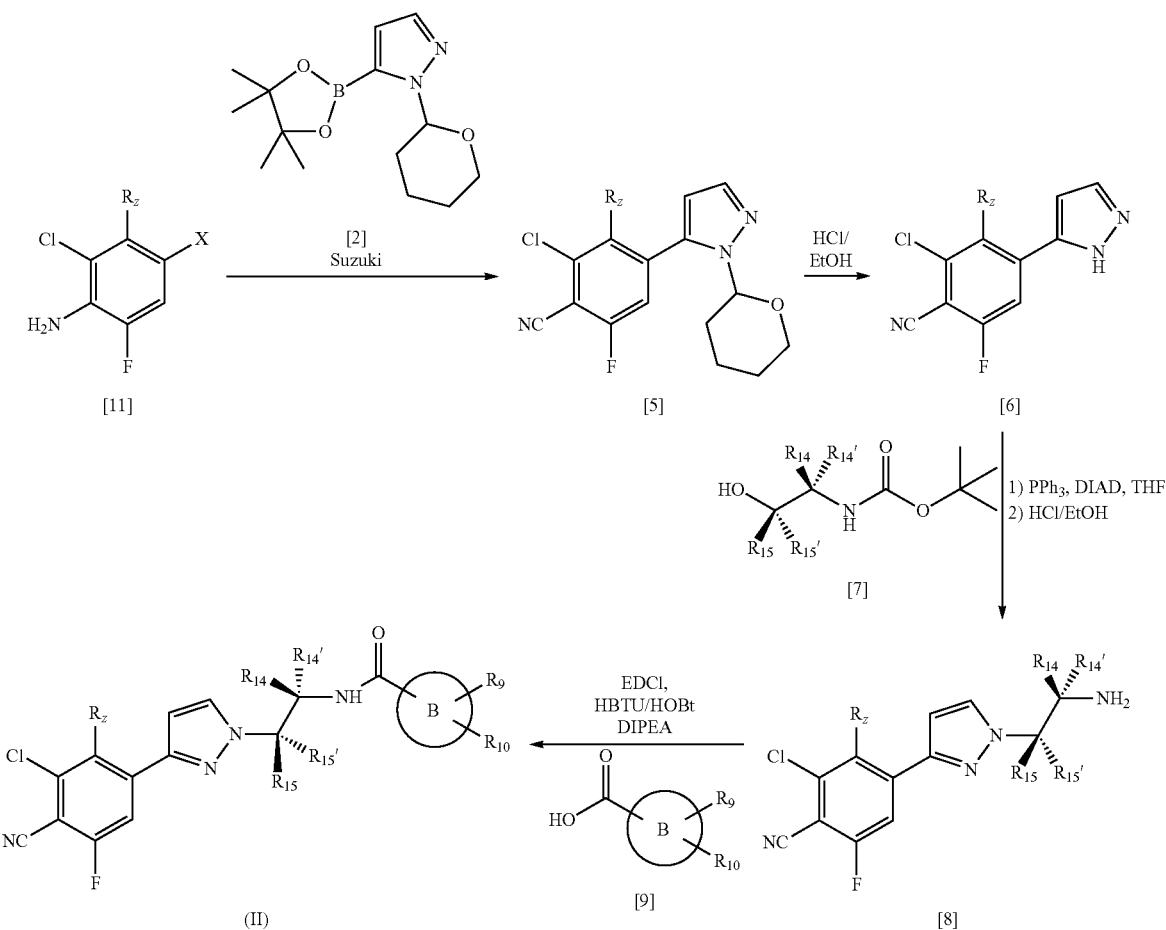

The starting compound [11] of Scheme 2 can be suitably prepared from 3-chloro-5-fluoroaniline according to Scheme 3, wherein X is a halogen.

SCHEME 3

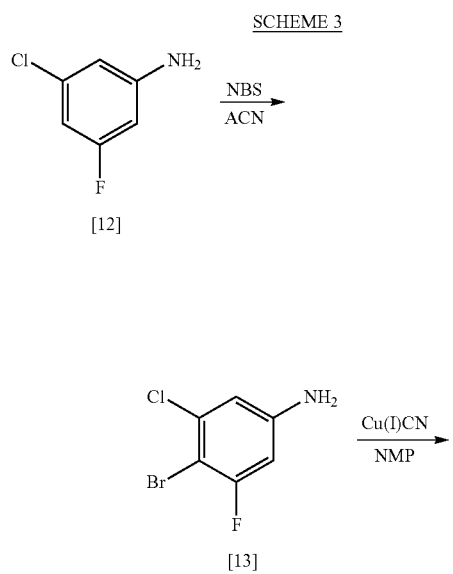

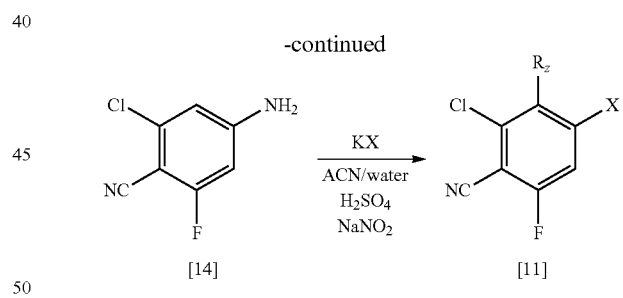

Other starting materials of the above Schemes are commercially available or can be prepared according to known methods.

Pharmaceutically acceptable salts, e.g. acid addition salts with both organic and inorganic acids are well known in the field of pharmaceuticals. Non-limiting examples of these salts include chlorides, bromides, sulfates, nitrates, phosphates, sulfonates, formates, tartrates, maleates, citrates, benzoates, salicylates and ascorbates. Pharmaceutically acceptable esters, when applicable, may be prepared by known methods using pharmaceutically acceptable acids that are conventional in the field of pharmaceuticals and that retain the pharmacological properties of the free form. Non-limiting examples of these esters include esters of aliphatic or aromatic alcohols, e.g. methyl, ethyl, propyl, isopropyl, butyl, isobutyl, sec-butyl, tert-butyl esters. Phosphate esters and carbonate esters, are also within the scope of the invention.

The definition of formula (I) or (II) above are inclusive of all the possible isotopes and stereoisomers of the compounds, including geometric isomers, e.g. Z and E isomers (cis and trans isomers), and optical isomers, e.g. diastereomers and enantiomers, and all prodrug esters, e.g. phosphate esters and carbonate esters. Furthermore, the invention includes in its scope both the individual isomers and any mixtures thereof, e.g. racemic mixtures.

In one embodiment, the term "isomer" is meant to encompass optical isomers of the compounds of the invention. It will be appreciated by those skilled in the art that the compounds of the present invention contain at least one chiral center. Accordingly, the compounds of the invention may exist in optically active or racemic forms. It is to be understood that the present invention encompasses any racemic or optically active form, or mixtures thereof. In one embodiment, the compounds of the invention are the pure (R)-isomers. In another embodiment, the compounds of the invention are the pure (S)-isomers. In another embodiment, the compounds of the invention are a mixture of the (R) and the (S) isomers. In another embodiment, the compounds of the invention are a racemic mixture comprising an equal amount of the (R) and the (S) isomers. The compounds of the invention may contain two chiral centers. In such case, according to one embodiment of the invention, the compounds of the invention are pure diasteromers. According to other embodiment of the invention, the compounds of the invention are a mixture of several diasteromers. The individual isomers may be obtained using the corresponding isomeric forms of the starting material or they may be separated after the preparation of the end compound according to conventional separation methods. For the separation of optical isomers, e.g. enantiomers or diastereomers, from the mixture thereof the conventional resolution methods, e.g. fractional crystallisation, may be used.

The terms employed herein have the following meanings:

The term "halo" or "halogen", as employed herein as such or as part of another group, refers to chlorine, bromine, fluorine or iodine.

The terms "$C_{1-7}$ alkyl", "$C_{2-7}$ alkyl" and "$C_4$ alkyl", as employed herein as such or as part of another group, refers to a saturated straight or branched carbon chain having 1 to 7 carbon atoms, 2 to 7 carbon atoms and 4 carbon atoms, respectively. Representative examples of $C_{1-7}$ alkyl include, but are not limited to, methyl, ethyl, n-propyl, isopropyl, n-butyl, isobutyl, sec-butyl, tert-butyl, n-pentyl, isopentyl, neopentyl, n-hexyl, and the like.

The term "$C_{2-7}$ alkenyl", as employed herein as such or as part of another group, refers to a straight or branched chain radical having 2 to 7 carbon atoms, which chain contains at least one double bond. Representative examples of $C_{2-7}$ alkenyl include, but are not limited to, ethenyl, propenyl, butenyl, and the like.

The term "$C_{1-7}$ alkylene linker" means a saturated straight or branched $C_{1-7}$ alkyl chain which connects two groups together. Representative examples of $C_{1-7}$ alkylene linker are methylene (—$CH_2$—) and ethylene (—$CH_2$—$CH_2$—) chains.

The term "$C_{3-7}$ cycloalkyl", as employed herein as such or as part of another group, refers to a saturated cyclic hydrocarbon group containing 3 to 7 carbons. Representative examples of $C_{3-7}$ cycloalkyl include, but are not limited to, cyclopropyl, cyclobutyl, cyclopentyl, cyclohexyl, and the like.

The term "$C_{3-7}$ cycloalkyl $C_{1-7}$ alkyl", as employed herein refers to a $C_{3-7}$ cycloalkyl group, as defined herein, appended to the parent molecular moiety through a $C_{1-7}$ alkyl group, as defined herein.

The term "hydroxy", as employed herein as such or as part of another group, refers to an —OH group.

The term "cyano", as employed herein as such or as part of another group, refers to a —CN group.

The term "hydroxy $C_{1-7}$ alkyl", as employed herein as such or as part of another group, refers to at least one hydroxy group, as defined herein, appended to the parent molecular moiety through a $C_{1-7}$ alkyl group, as defined herein. Representative examples of hydroxy $C_{1-7}$ alkyl include, but are not limited to, hydroxymethyl, 2,2-dihydroxyethyl, 1-hydroxyethyl, 3-hydroxypropyl, 1-hydroxypropyl, 1-methyl-1-hydroxyethyl, 1-methyl-1-hydroxypropyl, and the like.

The term "halo $C_{1-7}$ alkyl", as employed herein as such or as part of another group, refers to at least one halogen, as defined herein, appended to the parent molecular moiety through a $C_{1-7}$ alkyl group, as defined herein. Representative examples of halo $C_{1-7}$ alkyl include, but are not limited to, fluoromethyl, difluoro-methyl, trifluoromethyl, 2-chloroethyl, 3-bromopropyl, and the like.

The term "cyano $C_{1-7}$ alkyl", as employed herein as such or as part of another group, refers to at least one cyano group, appended to the parent molecular moiety through a $C_{1-7}$ alkyl group, as defined herein. Representative examples include, but are not limited to, cyanomethyl, 3-cyanopropyl, and the like.

The term "$C_{1-7}$ alkoxy $C_{1-7}$ alkyl", refers to $C_{1-7}$ alkoxy group as defined herein, appended to the parent molecular moiety through a $C_{1-7}$ alkyl group, as defined herein.

The term "oxo" as employed herein as such or as part of another group, refers to group (=O) attached as a substituent.

The term "carboxyl", as employed herein as such or as part of another group, refers to a —COOH group.

The term "carbamoyl", as employed herein as such or as part of another group, refers to a —(C=O)—$NH_2$ group.

The term "carbamoyl $C_{1-7}$ alkyl", as employed herein as such or as part of another group, refers to carbamoyl group appended to the parent molecular moiety through a $C_{1-7}$ alkyl group.

The term "carboxy $C_{1-7}$ alkyl" employed herein, refers to —COOH group appended to the parent molecular moiety through a $C_{1-7}$ alkyl group, as defined herein.

The term "$C_{1-7}$ alkoxycarbamoyl $C_{1-7}$ alkyl" as employed herein, refers to —$C_{1-7}$ alkyl-(C=O)—NH—O—$C_{1-7}$ alkyl group wherein $C_{1-7}$ alkyl is as defined herein.

The term "amino", as employed herein as such or as part of another group, refers to a —$NH_2$ group.

The term "oxo $C_{1-7}$ alkyl", as employed herein by itself or as part of another group, refers a $C_{1-7}$ alkyl group as defined herein containing a carbonyl radical anywhere in an alkyl chain. Examples thereof include acetyl, propanoyl, iso-propanoyl, butanoyl, sec-butanoyl, tert-butanoyl and pentanoyl.

The term "amino $C_{1-7}$ alkyl", as employed herein, refers to at least one amino group, as defined herein, appended to the parent molecular moiety through a $C_{1-7}$ alkyl group, as defined herein. Representative examples of amino $C_{1-7}$ alkyl include, but are not limited to, aminomethyl, 2-aminoethyl, 1-aminoethyl, 2,2-di-aminoethyl, 3-aminopropyl, 2-aminopropyl, 4-aminobutyl, 1-methyl-1-aminoethyl, and the like.

The term "$C_{1-7}$ alkylamino", as employed herein as such or as part of another group, refers to one or two $C_{1-7}$ alkyl group(s), as defined herein, appended to the parent molecular moiety through an amino group, as defined herein. Representative examples of $C_{1-7}$ alkylamino include, but are not limited to methylamino, ethylamino, propylamino, dimethylamino, diethylamino, N-ethyl-N-methylamino, and the like.

The term "$C_{1-7}$ alkylamino $C_{1-7}$ alkyl", as employed herein, refers to $C_{1-7}$ alkylamino group, as defined herein, appended to the parent molecular moiety through a $C_{1-7}$ alkyl group, as defined herein. Representative examples of $C_{1-7}$ alkylamino $C_{1-7}$ alkyl include, but are not limited to, N,N-dimethylaminomethyl, N,N-di-ethylaminomethyl, N-methylaminoethyl, N-methylaminopropyl, N-ethyl-N-methyl-aminomethyl, and the like.

The term "hydroxy $C_{1-7}$ alkylamino", as employed herein, refers to at least one hydroxy group appended to the parent molecular moiety through a $C_{1-7}$ alkylamino group, as defined herein. Representative examples of $C_{1-7}$ alkylamino $C_{1-7}$ alkyl include, but are not limited to, N-hydroxymethylamino, N-ethyl-N-hydroxymethylamino, and the like.

The term "$C_{1-7}$ alkoxy $C_{1-7}$ alkylamino", as employed herein refers to at least one $C_{1-7}$ alkoxy group appended to the parent molecular moiety through a $C_{1-7}$ alkylamino group, as defined herein. Representative examples include, but are not limited to, N-ethoxymethylamino, N-ethyl-N-metoxymethylamino and the like.

The term "hydroxy $C_{1-7}$ alkylamino $C_{1-7}$ alkyl", as employed herein, refers to hydroxy $C_{1-7}$ alkylamino group, as defined herein, appended to the parent molecular moiety through a $C_{1-7}$ alkyl group, as defined herein. Representative examples of $C_{1-7}$ alkylamino $C_{1-7}$ alkyl include, but are not limited to, N-hydroxymethylaminoethyl, N-ethyl-N-hydroxymethylaminomethyl, and the like.

The term "$C_{1-7}$ alkoxy $C_{1-7}$ alkyl", as employed herein, refers to at least one $C_{1-7}$ alkoxy group, as defined herein, appended to the parent molecular moiety through a $C_{1-7}$ alkyl group, as defined herein. Representative examples of $C_{1-7}$ alkoxy $C_{1-7}$ alkyl include, but are not limited to methoxymethyl, ethoxymethyl, 2-methoxy-ethyl, 2-ethoxyethyl, 3,3-dimethoxypropyl, 2,4-dimethoxybutyl and the like.

The term "imino $C_{1-7}$ alkyl", as employed herein, refers to at least one imino group (=NH) appended to the parent molecular moiety through a $C_{1-7}$ alkyl group, as defined herein.

The term "hydroxyimino $C_{1-7}$ alkyl", as employed herein, refers to =N—OH group appended to the parent molecular moiety through a $C_{1-7}$ alkyl group, as defined herein.

The term "5- or 6-membered heterocyclic ring" as employed herein, refers to a saturated, partially saturated or aromatic ring with 5 or 6 ring atoms, of which 1-3 atoms are heteroatoms selected from a group consisting of N, O and S. Representative examples of 5- or 6-membered heterocyclic ring include, but are not limited to, pyrazolyl, pyridinyl, isoxazolyl, imidazolyl, furanyl, piperazinyl, piperidinyl, rings and the like.

The term "5- or 6-membered carbocyclic ring" as employed herein, refers to a saturated, partially saturated or aromatic ring with 5 or 6 ring atoms consisting of carbon atoms only. Representative examples of 5- or 6-membered carbocyclic ring include, but are not limited to, phenyl and cyclohexyl rings and the like.

The term "5-12 membered heterocyclic ring" as employed herein, refers to a monocyclic or bicyclic saturated, partially saturated or aromatic ring with 5 to 12 ring atoms, of which 1-4 atoms are heteroatoms selected from a group consisting of N, O and S. Representative examples of 5-12 membered heterocyclic ring include, but are not limited to, pyrazolyl, pyridinyl, isoxazolyl, imidazolyl, furanyl, piperazinyl, piperidinyl, morpholinyl, pyrazinyl, indazolyl, pyrazolo[1,5-a]pyrimidinyl, isoxazolyl and thiazolyl rings and the like.

The term "5-12 membered carbocyclic ring" as employed herein, refers to a monocyclic or bicyclic saturated, partially saturated or aromatic ring with 5 to 12 ring atoms consisting of carbon atoms only. Representative examples of 5-12 membered carbocyclic rings include, but are not limited to, phenyl and naphtyl rings and the like.

The term "optionally substituted" as used herein in connection with various residues refers to halogen, $C_{1-7}$ alkyl, $C_{2-7}$ alkenyl, $C_{3-7}$ cycloalkyl, hydroxy, amino, halo $C_{1-7}$ alkyl, hydroxy $C_{1-7}$ alkyl, $C_{1-7}$ alkoxy, oxo $C_{1-7}$ alkyl, $C_{1-7}$ alkylamino, amino $C_{1-7}$ alkyl, methylsulfonyl, nitro, cyano or thiol substituents. Preferred substituents are halogen, $C_{1-7}$ alkyl, $C_{3-7}$ cycloalkyl, hydroxy $C_{1-7}$ alkyl, oxo $C_{1-7}$ alkyl substituents. The "optionally substituted" groups may contain 1 to 3, preferably 1 or 2, most preferably 1 of the above mentioned substituents.

Examples of preferred compounds of formula (I) or (II) include (S)—N-(1-(3-(3-Chloro-4-cyano-2,5-difluorophenyl)-1H-pyrazol-1-yl)propan-2-yl)-2-methyl-1H-imidazole-5-carboxamide;

(S)—N-(1-(3-(3-Chloro-4-cyano-2,5-difluorophenyl)-1H-pyrazol-1-yl)-propan-2-yl)-2-(2-hydroxypropan-2-yl)oxazole-5-carboxamide;

(S)—N-(1-(3-(3-Chloro-4-cyano-5-fluorophenyl)-1H-pyrazol-1-yl)propan-2-yl)-6-cyanoimidazo[1,2-a]pyridine-2-carboxamide;

(S)—N-(1-(3-(3-Chloro-4-cyano-5-fluorophenyl)-1H-pyrazol-1-yl)propan-2-yl)-7-oxo-5,6,7,8-tetrahydroimidazo[1,2-a]pyrimidine-2-carboxamide;

(S)—N-(1-(3-(3-Chloro-4-cyano-5-fluorophenyl)-1H-pyrazol-1-yl)propan-2-yl)-3-isopropyl-1,2,4-oxadiazole-5-carboxamide;

(S)—N-(1-(3-(3-Chloro-4-cyano-5-fluorophenyl)-1H-pyrazol-1-yl)propan-2-yl)-5,7-dimethylimidazo[1,2-c]pyrimidine-2-carboxamide;

(S)-5-((1H-Imidazol-1-yl)methyl)-N-(1-(3-(3-chloro-4-cyano-5-fluorophenyl)-1H-pyrazol-1-yl)propan-2-yl)isoxazole-3-carboxamide;

(S)—N-(1-(3-(3-Chloro-4-cyano-5-fluorophenyl)-1H-pyrazol-1-yl)propan-2-yl)-5-oxo-5,6-dihydroimidazo[1,2-c]pyrimidine-2-carboxamide;

(S)—N-(1-(3-(3-Chloro-4-cyano-5-fluorophenyl)-1H-pyrazol-1-yl)propan-2-yl)-1,6-dihydropyrrolo[2,3-c]pyrazole-5-carboxamide;

(S)—N-(1-(3-(3-Chloro-4-cyano-5-fluorophenyl)-1H-pyrazol-1-yl)propan-2-yl)imidazo[2,1-b]thiazole-6-carboxamide;

(S)—N-(1-(3-(3-Chloro-4-cyano-5-fluorophenyl)-1H-pyrazol-1-yl)propan-2-yl)-6-nitroimidazo[1,2-a]pyridine-2-carboxamide;

(S)—N-(1-(3-(3-Chloro-4-cyano-5-fluorophenyl)-1H-pyrazol-1-yl)propan-2-yl)-5,6,7,8-tetrahydroimidazo[1,2-a]pyridine-2-carboxamide;

(S)—N-(1-(3-(3-Chloro-4-cyano-5-fluorophenyl)-1H-pyrazol-1-yl)-propan-2-yl)-1-isopropyl-2-methyl-1H-imidazole-4-carboxamide;

(S)—N-(1-(3-(3-Chloro-4-cyano-5-fluorophenyl)-1H-pyrazol-1-yl)propan-2-yl)-5-(2-hydroxypropan-2-yl)-1H-pyrazole-3-carboxamide;

(S)—N-(1-(3-(3-Chloro-4-cyano-5-fluorophenyl)-1H-pyrazol-1-yl)-propan-2-yl)-1-(2,2-difluoroethyl)-2-methyl-1H-imidazole-4-carboxamide;

N—((S)-1-(3-(3-Chloro-4-cyano-5-fluorophenyl)-1H-pyrazol-1-yl)-propan-2-yl)-1-((R)-2-hydroxypropyl)-2-methyl-1H-imidazole-4-carboxamide;

(S)—N-(1-(3-(3-Chloro-4-cyano-5-fluorophenyl)-1H-pyrazol-1-yl)propan-2-yl)-1'-methyl-1'H-1,4'-bipyrazole-3-carboxamide;

(S)—N-(1-(3-(3-Chloro-4-cyano-5-fluorophenyl)-1H-pyrazol-1-yl)propan-2-yl)-1H,2'H-3,3'-bipyrazole-5-carboxamide;

N—((S)-1-(3-(3-Chloro-4-cyano-5-fluorophenyl)-1H-pyrazol-1-yl)-propan-2-yl)-1-((S)-2-hydroxypropyl)-2-methyl-1H-imidazole-4-carboxamide;

(S)—N-(1-(3-(3-Chloro-4-cyano-5-fluorophenyl)-1H-pyrazol-1-yl)propan-2-yl)-3,3'-bipyridine-6-carboxamide;

(S)—N-(1-(3-(3-Chloro-4-cyano-5-fluorophenyl)-1H-pyrazol-1-yl)-propan-2-yl)-6-(3,3-dimethylureido)imidazo[1,2-a]pyridine-2-carboxamide;

(S)—N-(1-(3-(3-Chloro-4-cyano-5-fluorophenyl)-1H-pyrazol-1-yl)-propan-2-yl)-6-(methylsulfonamido)imidazo[1,2-a]pyridine-2-carboxamide;

N—((S)-1-(3-(3-Chloro-4-cyano-5-fluorophenyl)-1H-pyrazol-1-yl)propan-2-yl)-5-(1-hydroxy-2-methylpropyl)isoxazole-3-carboxamide;

(S)—N-(1-(3-(3-Chloro-4-cyano-5-fluorophenyl)-1H-pyrazol-1-yl)propan-2-yl)-5-(1,5-dimethyl-1H-pyrazol-3-yl)-1,2,4-oxadiazole-3-carboxamide;

(S)—N-(1-(3-(3-Chloro-4-cyano-5-fluorophenyl)-1H-pyrazol-1-yl)propan-2-yl)-5-(isoxazol-3-yl)-1,2,4-oxadiazole-3-carboxamide;

(S)—N-(1-(3-(3-Chloro-4-cyano-5-fluorophenyl)-1H-pyrazol-1-yl)-propan-2-yl)-3-(1H-imidazol-4-yl)-1H-pyrazole-5-carboxamide;

(S)—N-(1-(3-(3-Chloro-4-cyano-5-fluorophenyl)-1H-pyrazol-1-yl)-propan-2-yl)-2-(chloropropan-2-yl)oxazole-4-carboxamide;

(S)—N-(1-(3-(3-Chloro-4-cyano-5-fluorophenyl)-1H-pyrazol-1-yl)-propan-2-yl)-2-(2-propen-2-yl)oxazole-4-carboxamide;

(S)—N-(1-(3-(3-Chloro-4-cyano-5-fluorophenyl)-1H-pyrazol-1-yl)propan-2-yl)-N-5-cyclopropylisoxazole-3,5-dicarboxamide;

(S)-2-Bromo-N-(1-(3-(3-chloro-4-cyano-5-fluorophenyl)-1H-pyrazol-1-yl)-propan-2-yl)-1H-imidazole-4-carboxamide;

(S)—N-(1-(3-(3-Chloro-4-cyano-5-fluorophenyl)-1H-pyrazol-1-yl)propan-2-yl)-1-(2-methylprop-1-enyl)-1H-pyrazole-3-carboxamide;

(S)—N-(1-(3-(3-Chloro-4-cyano-5-fluorophenyl)-1H-pyrazol-1-yl)propan-2-yl)-1-cyclopropyl-1H-pyrazole-3-carboxamide;

N—((S)-1-(3-(3-Chloro-4-cyano-5-fluorophenyl)-1H-pyrazol-1-yl)propan-2-yl)-2-(1-hydroxyethyl)-1H-imidazole-4-carboxamide;

(S)-2-acetyl-N-(1-(3-(3-chloro-4-cyano-5-fluorophenyl)-1H-pyrazol-1-yl)-propan-2-yl)-1H-imidazole-4-carboxamide;

(S)—N-(1-(3-(3-Chloro-4-cyano-5-fluorophenyl)-1H-pyrazol-1-yl)propan-2-yl)-2-(2-hydroxypropan-2-yl)-1H-imidazole-4-carboxamide;

(S)—N-(1-(3-(3-Chloro-4-cyano-5-fluorophenyl)-1H-pyrazol-1-yl)propan-2-yl)-2-cyclopropyl-1-methyl-1H-imidazole-4-carboxamide;

(S)—$N^4$-(1-(3-(3-Chloro-4-cyano-5-fluorophenyl)-1H-pyrazol-1-yl)propan-2-yl)-1H-imidazole-2,4-dicarboxamide:

4-(1-(3-((S)-1-(3-(3-Chloro-4-cyanophenyl)-1H-pyrazol-1-yl)propan-2-ylcarbamoyl)-1H-pyrazol-5-yl)ethoxy)-4-oxobutanoic acid;

(S)-5-Chloro-N-(1-(3-(3-chloro-4-cyanophenyl)-1H-pyrazol-1-yl)-propan-2-yl)pyrazine-2-carboxamide;

N—((S)-1-(3-(3-Chloro-4-cyanophenyl)-1H-pyrazol-1-yl)propan-2-yl)-1-((S)-2-hydroxypropyl)-2-methyl-1H-imidazole-4-carboxamide;

(S)-1-Butyl-N-(1-(3-(3-chloro-4-cyanophenyl)-1H-pyrazol-1-yl)propan-2-yl)-2-methyl-1H-imidazole-4-carboxamide;

(S)—N-(1-(3-(3-Chloro-4-cyanophenyl)-1H-pyrazol-1-yl)propan-2-yl)-5-(2-hydroxypropan-2-yl)-1H-pyrazole-3-carboxamide;

(S)—N-(1-(3-(3-Chloro-4-cyanophenyl)-1H-pyrazol-1-yl)propan-2-yl)-1'-methyl-1'H-1,4'-bipyrazole-3-carboxamide;

N—((S)-1-(3-(3-Chloro-4-cyanophenyl)-1H-pyrazol-1-yl)propan-2-yl)-1-((R)-2-hydroxypropyl)-2-methyl-1H-imidazole-4-carboxamide;

(S)-2-Bromo-N-(1-(3-(3-chloro-4-cyanophenyl)-1H-pyrazol-1-yl)-propan-2-yl)-1H-imidazole-4-carboxamide;

N—((S)-1-(3-(3-Chloro-4-cyanophenyl)-1H-pyrazol-1-yl)propan-2-yl)-5-(1-hydroxy-2-methylpropyl)isoxazole-3-carboxamide;

(S)—N-(1-(3-(3-Chloro-4-cyanophenyl)-1H-pyrazol-1-yl)propan-2-yl)-1-(2-cyanoethyl)-2-methyl-1H-imidazole-4-carboxamide;

N—((S)-1-(3-(3-Chloro-4-cyanophenyl)-1H-pyrazol-1-yl)propan-2-yl)-1-(1-cyanoethyl)-2-methyl-1H-imidazole-4-carboxamide;

(S)—N-(1-(3-(3-Chloro-4-cyanophenyl)-1H-pyrazol-1-yl)propan-2-yl)-1-(2-methylprop-1-enyl)-1H-pyrazole-3-carboxamide;

(S)—N-(1-(3-(3-Chloro-4-cyanophenyl)-1H-pyrazol-1-yl)propan-2-yl)-3-(1H-imidazol-4-yl)-1H-pyrazole-5-carboxamide;

(S)—N-(1-(3-(3-Chloro-4-cyanophenyl)-1H-pyrazol-1-yl)propan-2-yl)-1-cyclopropyl-1H-pyrazole-3-carboxamide;

(S)—N-(1-(3-(3-Chloro-4-cyanophenyl)-1H-pyrazol-1-yl)propan-2-yl)-1-(6-(dimethylamino)pyridin-3-yl)-1H-pyrazole-3-carboxamide;

(S)—N-(1-(3-(3-Chloro-4-cyanophenyl)-1H-pyrazol-1-yl)propan-2-yl)-4,5,6,7-tetrahydropyrazolo[1,5-a]pyridine-2-carboxamide);

N—((S)-1-(3-(3-Chloro-4-cyanophenyl)-1H-pyrazol-1-yl)propan-2-yl)-2-(1-hydroxyethyl)-1H-imidazole-4-carboxamide;

(S)—N-(1-(3-(3-Chloro-4-cyanophenyl)-1H-pyrazol-1-yl)propan-2-yl)-2-isopropyl-1H-imidazole-4-carboxamide;

(S)-2-Butyl-N-(1-(3-(3-chloro-4-cyanophenyl)-1H-pyrazol-1-yl)propan-2-yl)-1-methyl-1H-imidazole-4-carboxamide;

(S)—N-(1-(3-(3-Chloro-4-cyanophenyl)-1H-pyrazol-1-yl)propan-2-yl)-2-(2-hydroxypropan-2-yl)-1-methyl-1H-imidazole-4-carboxamide;

(S)—N-(1-(3-(3-Chloro-4-cyanophenyl)-1H-pyrazol-1-yl)propan-2-yl)-1-methyl-2-(1-methyl-1H-pyrazol-4-yl)-1H-imidazole-4-carboxamide;

(S)—N-(1-(3-(3-Chloro-4-cyanophenyl)-1H-pyrazol-1-yl)propan-2-yl)-2-cyclopropyl-1-methyl-1H-imidazole-4-carboxamide;

(S)—$N^4$-(1-(3-(3-Chloro-4-cyanophenyl)-1H-pyrazol-1-yl)propan-2-yl)-1H-imidazole-2,4-dicarboxamide;

(S)—N-(1-(3-(4-Cyano-3-(trifluoromethyl)phenyl)-1H-pyrazol-1-yl)propan-2-yl)-2-(2-hydroxypropan-2-yl)oxazole-4-carboxamide and pharmaceutically acceptable salts thereof.

Further examples of preferred compounds of formula (I) or (II) include (S)—N-(2-(3-(3-Chloro-4-cyano-5-fluorophenyl)-1H-pyrazol-1-yl)propyl)-2-(2-hydroxypropan-2-yl)oxazole-4-carboxamide;

(R)—N-(2-(3-(3-Chloro-4-cyano-5-fluorophenyl)-1H-pyrazol-1-yl)propyl)-2-(2-hydroxypropan-2-yl)oxazole-4-carboxamide;

(R)—N-(2-(3-(3-Chloro-4-cyano-5-fluorophenyl)-1H-pyrazol-1-yl)propyl)-2-(2-hydroxypropan-2-yl)-1H-imidazole-4-carboxamide;

(S)—N-(1-(3-(3-Chloro-4-cyano-5-fluorophenyl)-1H-pyrazol-1-yl)propan-2-yl)-2-(2,2,2-trifluoroethyl)-1H-imidazole-4-carboxamide;

(S)—N-(1-(3-(3-Chloro-4-cyano-5-fluorophenyl)-1H-pyrazol-1-yl)propan-2-yl)-2-(trifluoromethyl)-1H-imidazole-4-carboxamide;

N—((S)-1-(3-(3-Chloro-4-cyano-5-fluorophenyl)-1H-pyrazol-1-yl)propan-2-yl)-3-((S)-1-hydroxyethyl)-1,2,4-oxadiazole-5-carboxamide;

N—((S)-1-(3-(3-chloro-4-cyano-5-fluorophenyl)-1H-pyrazol-1-yl)propan-2-yl)-3-((R)-1-hydroxyethyl)-1,2,4-oxadiazole-5-carboxamide;

(S)—N-(2-(3-(3-Chloro-4-cyano-5-fluorophenyl)-1H-pyrazol-1-yl)propyl)-3-(2-hydroxypropan-2-yl)-1,2,4-oxadiazole-5-carboxamide;

(S)—N-(1-(3-(3-Chloro-4-cyano-5-fluorophenyl)-1H-pyrazol-1-yl)propan-2-yl)-3-(2-hydroxypropan-2-yl)-1,2,4-oxadiazole-5-carboxamide;

(S)—N-(1-(3-(3-Chloro-4-cyano-5-fluorophenyl)-1H-pyrazol-1-yl)propan-2-yl)-2-cyclopropyl-1H-imidazole-4-carboxamide;

(S)—N$^4$-(1-(3-(3-Chloro-4-cyano-5-fluorophenyl)-1H-pyrazol-1-yl)propan-2-yl)-N$^2$,N$^2$-dimethyl-1H-imidazole-2,4-dicarboxamide;

(S)—N-(1-(3-(3-Chloro-4-cyano-5-fluorophenyl)-1H-pyrazol-1-yl)propan-2-yl)-2-(2-ethoxypropan-2-yl)-1H-imidazole-4-carboxamide;

N—((S)-1-(3-(3-Chloro-4-cyano-5-fluorophenyl)-1H-pyrazol-1-yl)propan-2-yl)-2-(1-ethoxyethyl)-1H-imidazole-4-carboxamide;

(S)—N-(1-(3-(3-Chloro-4-cyano-5-fluorophenyl)-1H-pyrazol-1-yl)propan-2-yl)-2-(2-ethoxypropan-2-yl)oxazole-4-carboxamide;

(S)—N-(1-(3-(3-Chloro-4-cyano-5-fluorophenyl)-1H-pyrazol-1-yl)propan-2-yl)-5-(2-hydroxy-2-methylpropyl)-1H-pyrazole-3-carboxamide and pharmaceutically acceptable salts thereof.

Compounds of the invention may be administered to a patient in therapeutically effective amounts which range usually from about 0.1 to about 5000 mg, preferably from about 1 to about 2000 mg, per day depending on the age, weight, ethnic group, condition of the patient, condition to be treated, administration route and the androgen (AR) modulator used. The compounds of the invention can be formulated into dosage forms using the principles known in the art. It can be given to a patient as such or in combination with suitable pharmaceutical excipients in the form of tablets, granules, capsules, suppositories, emulsions, suspensions or solutions. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds and other ingredients normally used in this field of technology may be also used. The compositions containing the active compound can be given enterally or parenterally, the oral route being the preferred way. The contents of the active compound in the composition is from about 0.5 to 100%, preferably from about 1 to about 85%, per weight of the total composition.

The compounds of the invention can be given to the subject as the sole active ingredient or in combination with one of more other active ingredients suitable for the treatment or prevention of an AR dependent condition, e.g. AR dependent cancer such as prostate cancer, and other diseases where AR antagonism is desired.

The present invention will be explained in more detail by the following examples. The examples are meant only for illustrating purposes and do not limit the scope of the invention defined in claims.

EXAMPLES

The end products of the following Examples were prepared as a mixture of diastereomers unless otherwise indicated.

Example 1

(S)—N-(1-(3-(3-Chloro-4-cyano-2,5-difluorophenyl)-1H-pyrazol-1-yl)propan-2-yl)-2-methyl-1H-imidazole-5-carboxamide a) 4-Bromo-2-chloro-3,6-difluoroaniline 2-Chloro-3,6-difluoroaniline (18.34 mmol, 3 g) was dissolved in ACN and cooled to 0° C. with an ice bath. A solution of N-bromosuccinimide (18.34 mmol, 3.26 g) dissolved in ACN was added using a dropping funnel maintaining the internal temperature of the reaction mixture below 5° C. After addition the mixture was stirred for 15 min letting the temperature slowly rise to ambient temperature. The reaction mixture was diluted with 10% aq. NaHSO$_3$, stirred for 10 min and evaporated to ⅓ of the original volume. The residue was diluted with water and extracted twice with excess of ethyl acetate. The organics were dried, filtered and evaporated. The product was purified with flash chromatography. 4.087 g of the title compound was obtained. $^1$H-NMR (400 MHz, DMSO-d$_6$): δ 5.97 (s, 2H), 7.42-7.52 (m, 1H).

b) 2-Chloro-3,6-difluoro-4-(1-(tetrahydro-2H-pyran-2-yl)-1H-pyrazol-5-yl)-aniline 4-Bromo-2-chloro-3,6-difluoroaniline (12.37 mmol, 3 g) and 1-(tetrahydro-2H-pyran-2-yl)-1H-pyrazole-5-boronic acid pinacol ester (12.37 mmol, 3.44 g) were dissolved in DME. Bis(triphenylphosphine)palladium(II) chloride (0.619 mmol, 0.434 g) and sodium carbonate, 2 M solution (12.37 mmol, 1.311 g) were added. The reaction mixture was refluxed at 80° C. for 4 h and the stirring was continued at 50° C. overnight. The solvent was evaporated and the residue was extracted three times with EtOAc. The combined organics were washed with water and brine. The organics were dried, filtered and evaporated. The crude product was purified by flash chromatography. 1.935 g of the title compound was obtained. $^1$H-NMR (400 MHz, MeOH-d$_4$): δ 1.49-1.79 (m, 2H), 1.80-1.88 (m, 1H), 1.93-2.19 (m, 2H), 2.33-2.47 (m, 1H), 3.47-3.77 (m, 1H), 3.96-4.07 (m, 1H), 5.09-5.43 (m, 1H), 6.30-6.39 (m, 1H), 7.04-7.13 (m, 1H), 7.50-7.63 (m, 1H).

c) 5-(3-Chloro-2,5-difluoro-4-iodophenyl)-1-(tetrahydro-2H-pyran-2-yl)-1H-pyrazole Copper(I) iodide (7.43 mmol, 1.415 g) and tert-butyl nitrite (10.40 mmol, 1.073 g) were stirred in ACN. The mixture was warmed to 75° C. 2-Chloro-3,6-difluoro-4-(1-(tetrahydro-2H-pyran-2-yl)-1H-pyrazol-5-yl)aniline (6.17 mmol, 1.935 g) dissolved in ACN was added dropwise during 20 min. The resulting mixture was stirred for 6 h at 75° C. The mixture was cooled to RT and a solution of aqueous sodium thiosulfate was added. The mixture was extracted three times with ethyl acetate. The combined organics were washed with brine, dried, filtered and evaporated. The crude product was purified by flash chromatography. 0.716 g of the title compound was obtained. $^1$H-NMR (400 MHz, DMSO-$d_6$): δ 1.48-1.74 (m, 3H), 1.81-2.02 (m, 2H), 2.30-2.44 (m, 1H), 3.47-3.58 (m, 1H), 3.86-3.96 (m, 1H), 5.28 (dd, 1H), 6.60-6.65 (m, 1H), 7.46-7.52 (m, 1H), 7.69-7.72 (m, 1H).

d) 2-Chloro-3,6-difluoro-4-(1-(tetrahydro-2H-pyran-2-yl)-1H-pyrazol-5-yl)-benzonitrile 5-(3-Chloro-2,5-difluoro-4-iodophenyl)-1-(tetrahydro-2H-pyran-2-yl)-1H-pyrazole (1.686 mmol, 0.716 g) and copper(I) cyanide (1.686 mmol, 0.151 g) were suspended in NMP. The resulting mixture was stirred at 170° C. for 7 h. The reaction was quenched by, pouring the mixture onto 12% ammonia solution and stirred for 20 min. The formed precipitate was filtered and washed with water. 0.276 g of the title product was obtained. Identification after the next step due to low solubility of the product.

e) 2-Chloro-3,6-difluoro-4-(1H-pyrazol-5-yl)benzonitrile

2-Chloro-3,6-difluoro-4-(1-(tetrahydro-2H-pyran-2-yl)-1H-pyrazol-5-yl)-benzonitrile (0.853 mmol, 0.276 g) was stirred in ethanol. 10% HCl/EtOH solution (5 ml) was slowly added. The resulting mixture was stirred at RT overnight. The reaction mixture was neutralized with NaHCO$_3$ and extracted twice with EtOAc. The combined organics were washed with water, dried, filtered and evaporated. 0.219 g of the title compound was obtained. $^1$H-NMR (400 MHz, DMSO-$d_6$): δ 6.86 (bs, 1H), 7.88-8.10 (m, 2H), 13.57 (bs, 1H).

f) (S)-4-(1-(2-Aminopropyl)-1H-pyrazol-3-yl)-2-chloro-3,6-difluorobenzonitrile 2-Chloro-3,6-difluoro-4-(1H-pyrazol-5-yl)benzonitrile (0.835 mmol, 0.2 g) was dissolved in THF under nitrogen atmosphere. (S)-tert-butyl (1-hydroxypropan-2-yl)carbamate (0.835 mmol, 0.146 g) and triphenylphosphine (1.252 mmol, 0.328 g) were dissolved in THF and added to the previous mixture. The resulting mixture was cooled to 0° C. Di-tert-butyl azodicarboxylate (1.252 mmol, 0.288 g) was added in small portions and stirred under cold conditions for 10 min. The flask was warmed to RT and stirred overnight. The solvent was evaporated. The residue was dissolved in ethanol and 10% HCl(g)/EtOH solution (15 ml) was slowly added. The resulting mixture was stirred overnight. The mixture was diluted with water and extracted twice with DCM. The combined organics were washed with water. The aqueous phases were combined and the pH was adjusted to 12 with 2 M NaOH. The aqueous phase was extracted three times with DCM. The combined organics were dried, filtered and evaporated. 0.167 g of the title compound was obtained. $^1$H-NMR (400 MHz, CDCl$_3$): δ 1.17 (d, 3H), 1.31 (bs, 2H), 3.53 (bs, 1H), 3.88-4.04 (m, 1H), 4.09-4.26 (m, 1H), 6.82 (dd, 1H), 7.55 (d, 1H), 7.88 (dd, 1H).

g) (S)—N-(1-(3-(3-Chloro-4-cyano-2,5-difluorophenyl)-1H-pyrazol-1-yl)-propan-2-yl)-2-methyl-1H-imidazole-5-carboxamide 2-Methyl-1H-imidazole-4-carboxylic acid (0.202 mmol, 0.026 g) was dissolved in DMF (5 ml) under nitrogen atmosphere. EDCI (0.202 mmol, 0.039 g), DIPEA (0.270 mmol, 0.035 g) and HBTU (0.034 mmol, 0.013 g) were added and the resulting mixture was stirred for 20 min at RT. (S)-4-(1-(2-aminopropyl)-1H-pyrazol-3-yl)-2-chloro-3,6-difluorobenzonitrile (0.135 mmol, 0.04 g) dissolved in DMF (2 ml) was added and the resulting mixture was stirred at RT for 3 days. The mixture was diluted with water and EtOAc, washed with 2M Na$_2$CO$_3$, water and brine. The combined organics were dried, filtered and evaporated. The crude product was purified by flash chromatography. 0.0324 g of the title compound was obtained. $^1$H-NMR (400 MHz, MeOH-$d_4$) δ ppm 1.23 (d, 3H), 2.38 (s, 3H), 4.28-4.47 (m, 2H), 4.48-4.58 (m, 1H), 6.77-6.82 (m, 1H), 7.46 (s, 1H), 7.77 (d, 1H), 7.83-7.96 (m, 1H).

Example 2

(S)—N-(1-(3-(3-Chloro-4-cyano-2,5-difluorophenyl)-1H-pyrazol-1-yl)-propan-2-yl)-2-(2-hydroxypropan-2-yl)oxazole-5-carboxamide a) Ethyl 2-chlorooxazole-4-carboxylate

Ethyl 2-aminooxazole-4-carboxylate (20 g, 128 mmol) was added to a solution of cupric chloride (32.8 g, 192 mmol) and t-butylnitrite (23 ml, 192 mmol) in ACN (500 ml) at 80° C. and the resulting mixture was refluxed for 4 h. The reaction mixture was concentrated and treated with concentrated HCl and extracted with EtOAc. The product was purified with flash chromatography. Yield 10.5 g. $^1$H-NMR (400 MHz; CDCl$_3$): δ 1.36 (t, 3H), 4.39 (q, 2H), 8.47 (s, 1H).

b) Ethyl 2-(1-ethoxyvinyl)oxazole-4-carboxylate

Ethyl 2-(1-ethoxyvinyl)oxazole-4-carboxylate was prepared using the procedure described in Example 33(a), starting from ethyl 2-chlorooxazole-4-carboxylate (10.5 g, 59.8 mmol) and tributyl(1-ethoxyvinyl)stannane (24 ml, 65.8 mmol), The product was purified with flash-chromatography. Yield 10.3 g. $^1$H-NMR (400 MHz; CDCl$_3$): δ ppm 1.23-1.46 (m, 6H), 3.94-3.99 (m, 2H), 4.36-4.42 (m, 2H), 4.8 (d, 1H), 5.33 (s, 1H), 8.19 (s, 1H).

c) Ethyl 2-acetyloxazole-4-carboxylate

Ethyl 2-acetyloxazole-4-carboxylate was prepared using the procedure described in Example 33(b), starting from ethyl 2-(1-ethoxyvinyl)oxazole-4-carboxylate (10.3 g, 48.8 mmol). Yield 7.0 g. $^1$H-NMR (400 MHz; CDCl$_3$): δ 1.46 (t, 3H), 2.73 (s, 3H), 4.41 (q, 2H), 8.34 (s, 1H).

d) Ethyl 2-(2-hydroxypropan-2-yl)oxazole-4-carboxylate

Into a flask containing a solution of ethyl 2-acetyloxazole-4-carboxylate (2.0 g, 10.9 mmol) in THF (50 ml), 3M solution of MeMgI in ether (5.0 ml, 13.11 mmol) was added at 0° C. The resulting mixture was stirred at RT for 5 h. The mixture was quenched with aqueous NH$_4$Cl solution and extracted with EtOAc. The organic layer was concentrated and purified with flash chromatography. Yield 1.0 g. $^1$H-NMR (400 MHz; CDCl$_3$): δ 1.59 (s, 3H), 1.66 (s, 6H), 2.70 (s, 1H), 4.39 (q, 2H), 8.17 (s, 1H).

e) 2-(2-Hydroxypropan-2-yl)oxazole-4-carboxylic acid 2-(2-Hydroxypropan-2-yl)oxazole-4-carboxylic acid was prepared using the procedure described in Example 32(d)

starting from ethyl 2-(2-hydroxypropan-2-yl)oxazole-4-carboxylate (1.0 g, 5.02 mmol). Yield 500 mg. $^1$H-NMR (400 MHz; DMSO-d$_6$): δ 1.50 (s, 6H), 5.67 (s, 1H), 8.67 (s, 1H), 12.98 (s, 1H).

f) (S)—N-(1-(3-(3-Chloro-4-cyano-2,5-difluorophenyl)-1H-pyrazol-1-yl)-propan-2-yl)-2-(2-hydroxypropan-2-yl)oxazole-5-carboxamide 2-(2-Hydroxypropan-2-yl)oxazole-4-carboxylic acid (0.514 mmol, 0.088 g) was dissolved in DMF (10 ml) under nitrogen atmosphere. EDCI (0.514 mmol, 0.098 g), DIPEA (0.856 mmol, 0.111 g) and HOBt (0.214 mmol, 0.029 g) were added and the resulting mixture was stirred for 20 min at RT. (S)-4-(1-(2-amino-propyl)-1H-pyrazol-3-yl)-2-chloro-3,6-difluorobenzonitrile (0.428 mmol, 0.127 g) dissolved in DMF (5 ml) was added and the resulting mixture was stirred at RT for 3 days. The mixture was diluted with water and EtOAc, washed with 2 M Na$_2$CO$_3$, water and brine. The combined organics were dried, filtered and evaporated. The crude product was purified by flash chromatography. 0.059 g of the title compound was obtained. $^1$H-NMR (400 MHz, MeOH-d$_4$): δ 1.26 (d, 3H), 1.61 (s, 6H), 4.34-4.46 (m, 2H), 4.54-4.63 (m, 1H), 6.78-6.82 (m, 1H), 7.76 (d, 1H), 7.87-7.93 (m, 1H), 8.24 (s, 1H).

Example 3

(S)—N-(1-(3-(3-Chloro-4-cyano-5-fluorophenyl)-1H-pyrazol-1-yl)propan-2-yl)-6-cyanoimidazo[1,2-a]pyridine-2-carboxamide a) 4-Bromo-3-chloro-5-fluoroaniline

3-Chloro-5-fluoroaniline (2061 mmol, 300 g) was dissolved in ACN (3000 ml) and the solution cooled to 0° C. NBS (2061 mmol, 367 g) was added to the reaction mixture in small portions keeping the temperature below 10° C. Reaction mixture was stirred at 10±5° C. for 3.5 h. 10% Aqueous NaHSO$_3$ was added and the reaction mixture was concentrated under vacuum to remove organic solvents. Water and DCM was added, stirred for 15 min and the phases were separated. The water phase was extracted with DCM. The combined organics were washed with water. The organic phase was evaporated. 2-Propanol was added to the residue and distilled until the steam temperature was 80° C. Water was added and the temperature was kept at 40±10° C. The mixture was cooled to 5° C. and stirred for 4 h. The precipitate was removed by filtration, washed with water and dried under vacuum. 440.7 g of the title compound was obtained. $^1$H-NMR (400 MHz, DMSO-d$_6$): δ 5.87 (s, 2H), 6.42-6.49 (m, 1H), 6.62-6.66 (m, 1H).

b) 4-Amino-2-chloro-6-fluorobenzonitrile

4-Bromo-3-Chloro-5-fluoroaniline (980 mmol, 220 g), copper(I)cyanide (980 mmol, 88 g) and NMP (1000 ml) were added into the reaction flask, heated up to 160° C. and stirred for 3 h to complete the reaction. The reaction mixture was cooled to RT. Water and 25% ammonia solution was added keeping the mixture at RT. The mixture was stirred overnight and the formed precipitate was separated by filtration and flushed with water. The filtered precipitate was dried under vacuum to give 117.7 g of the title compound. $^1$H-NMR (400 MHz, DMSO-d$_6$): δ 6.41-6.47 (m, 1H), 6.58-6.62 (m, 1H), 6.86 (bs, 2H).

c) 2-Chloro-6-fluoro-4-iodobenzonitrile

4-Amino-2-chloro-6-fluorobenzonitrile (293 mmol, 50 g) was dissolved in ACN (1550 ml) and water (460 ml). Sulphuric acid (879 mmol, 46.9 ml) was added carefully. The reaction mixture was cooled to 0° C. Sodium nitrite (322 mmol, 22.25 g) dissolved in water (150 ml) was slowly added keeping the reaction temperature below 10° C. Thereafter potassium iodide (586 mmol, 97 g) dissolved in 150 ml of water was added slowly while keeping the reaction temperature below 10° C. The reaction mixture was allowed to warm up to RT and stirred overnight at RT. The phases were separated and the organic phase was evaporated. Ethyl acetate was added into the evaporation residue and washed three times with 10% aqueous NaHSO$_3$. The organic phase was evaporated and the residue was dissolved in DCM. 5 g of active carbon was added and stirred for 2 h. The mixture was filtered through a layer of Celite and washed with DCM. The DCM-phase was evaporated and heptanes were added into the residue. The mixture was heated to 60° C. and stirred for 2 h. The oil and heptanes layers were separated by decantation. The heptanes phase was evaporated and 39.6 g of the title compound was obtained. $^1$H-NMR (400 MHz, DMSO-d$_6$): δ 8.06-8.10 (m, 1H), 8.10-8.11 (m, 1H).

d) 2-Chloro-6-fluoro-4-(1-(tetrahydro-2H-pyran-2-yl)-1H-pyrazol-5-yl)benzonitrile 2-Chloro-6-fluoro-4-iodobenzonitrile (291 mmol, 82 g), THF (800 ml) and 1-(tetra-hydro-2H-pyran-2-yl)-1H-pyrazole-5-boronic acid pinacol ester (350 mmol, 97 g) were added into a flask and stirred. Bis(triphenylphosphine)palladium(II) chloride (14.57 mmol, 10.22 g), sodium carbonate (699 mmol, 74.1 g) and water (350 ml) were added. The resulting mixture was heated to 60° C. and stirred for 2 h. The solvents were evaporated. Water was added and the mixture was left to stir overnight. EtOAc and water were added and the insoluble precipitates were removed by filtration. The organic phase was separated from the filtrate and the water phase was extracted with more EtOAc. The combined organics were evaporated and the residue was combined with previously filtrated solid. The collected solids were suspended in EtOH and water. The mixture was heated to boiling point, allowed to cool to RT and stirred for an hour at ambient temperature. The mixture was cooled to 0° C. and stirred for another hour. The precipitate was washed with a small amount of cold 1:1 water/EtOH. The filtered solids were dried under vacuum. 91.2 g of the title compound was obtained. $^1$H-NMR (400 MHz, DMSO-d$_6$): δ 1.50-1.70 (m, 3H), 1.79-1.89 (m, 1H), 1.92-2.03 (m, 1H), 2.30-2.44 (m, 1H), 3.56-3.67 (m, 1H), 3.93-4.02 (m, 1H), 5.36 (dd, 1H), 6.78 (d, 1H), 7.66 (d, 1H), 7.73 (dd, 1H), 7.80-7.83 (m, 1H).

e) 2-Chloro-6-fluoro-4-(1H-pyrazol-5-yl)benzonitrile hydrochloride

2-Chloro-6-fluoro-4-(1-(tetrahydro-2H-pyran-2-yl)-1H-pyrazol-5-yl)benzo-nitrile (298 mmol, 91 g) and 10% HCl/EtOH (339 ml) were mixed in a flask under nitrogen atmosphere. The resulting mixture was refluxed for 5 h during which 113 ml of 10% HCl/EtOH was added. The mixture was cooled to RT and stirred overnight. Next morning 40 ml of 10% HCl/EtOH was added and the mixture was refluxed for 3.5 h, cooled to 0° C. and stirred for an hour. The precipitate was removed by filtration and dried under vacuum. Half of the solvents in filtrate were evaporated and the remaining mixture was stirred at 0° C. for 3 h. The precipitates were again removed by filtration and dried under vacuum. The collected solids were combined to afford 51.8 g of the title compound. $^1$H-NMR (400 MHz, DMSO-$d_6$): δ 7.06 (d, 1H), 7.88 (d, 1H), 7.95 (dd, 1H), 8.03-8.07 (m, 1H).

f) 2-Chloro-6-fluoro-4-(1H-pyrazol-5-yl)benzonitrile

2-Chloro-6-fluoro-4-(1H-pyrazol-5-yl)benzonitrile hydrochloride (201 mmol, 51.8 g) was dissolved in THF (510 ml). Sodium hydroxide 50% (401 mmol, 32.1 g) was added and the resulting mixture was stirred at RT for 3 h. Almost all the solvents were evaporated and water was added to the residue. The mixture was stirred overnight at RT. The precipitate was removed by filtration the solid was flushed twice with water. The solid was dried under vacuum. 35.8 g of the title compound was obtained. $^1$H-NMR (400 MHz, DMSO-$d_6$): δ 7.05 (d, 1H), 7.88-7.97 (m, 2H), 8.02-8.07 (m, 1H), 13.37 (bs, 1H).

g) (S)-4-(1-(2-Aminopropyl)-1H-pyrazol-3-yl)-2-chloro-6-fluorobenzonitrile (S)-tert-Butyl (1-hydroxypropan-2-yl)carbamate (259 mmol, 45.4 g) and triphenylphosphine (259 mmol, 68.0 g) were mixed in dry EtOAc (380 ml) under nitrogen atmosphere. 2-Chloro-6-fluoro-4-(1H-pyrazol-3-yl)benzonitrile (130 mmol, 35.9 g) was added and the resulting mixture was stirred for 10 min. DIAD (259 mmol, 52.4 g) was added slowly while keeping the temperature between 15-25° C. with an ice bath. After the addition the mixture was allowed to warm to RT and stirred for 4 h. Water and concentrated HCl (1296 mmol, 106 ml) was added to the mixture and stirred for 6 days during which more HCl (107 ml in total) was added. Water and DCM was added and the mixture was stirred for a while before separating the phases. The organic phase was extracted twice with water. The water phases were combined and washed twice with DCM. DCM was added to the water phase and the pH of the water phase was adjusted to 12.5 with 50% NaOH. The phases were separated and the water phase was extracted once more with DCM. The DCM phases were combined and washed once with water. The separated DCM phase was evaporated and dried under vacuum. 24.0 g of the title compound was obtained. $^1$H-NMR (400 MHz, DMSO-$d_6$): δ 0.96 (d, 3H), 1.18 (bs, 2H), 3.19-3.29 (m, 1H), 3.97-4.08 (m, 2H), 7.03 (d, 1H), 7.85-7.92 (m, 2H), 7.98-8.02 (m, 1H).

h) (S)—N-(1-(3-(3-Chloro-4-cyano-5-fluorophenyl)-1H-pyrazol-1-yl)propan-2-yl)-6-cyanoimidazo[1,2-a]pyridine-2-carboxamide ORM-19702

6-Cyanoimidazo[1,2-a]pyridine-2-carboxylic acid (0.770 mmol, 0.144 g), HOBt (0.770 mmol, 0.104 g) and DIPEA (1.539 mmol, 0.199 g) were dissolved in DCM (5 ml) and DMF (1 ml). EDCI (0.770 mmol, 0.148 g) was added and the resulting mixture was stirred for 10 min at RT. (S)-4-(1-(2-aminopropyl)-1H-pyrazol-3-yl)-2-chloro-6-fluorobenzonitrile (0.592 mmol, 0.22 g) dissolved in small amount of DCM was added and the reaction mixture was stirred overnight at RT. The mixture was diluted with DCM, washed with 1M Na$_2$CO$_3$ and water. The organic phase was dried, filtered and evaporated. The crude product was purified by trituration from ACN. 0.054 g of the title compound was obtained. $^1$H-NMR (400 MHz, DMSO-$d_6$): δ 1.15 (d, 3H), 4.31-4.45 (m, 2H), 4.46-4.57 (m, 1H), 7.00 (d, 1H), 7.61-7.66 (m, 1H), 7.72-7.77 (m, 1H), 7.86-7.92 (m, 2H), 7.93-7.96 (m, 1H), 8.35-8.37 (m, 1H), 8.69 (d, 1H), 9.34-9.37 (m, 1H).

Example 4

(S)—N-(1-(3-(3-Chloro-4-cyano-5-fluorophenyl)-1H-pyrazol-1-yl)propan-2-yl)-7-oxo-5,6,7,8-tetrahydroimidazo[1,2-a]pyrimidine-2-carboxamide a) Ethyl 7-oxo-5,6,7,8-tetrahydroimidazo[1,2-a]pyrimidine-2-carboxylate Ethyl 2-amino-1H-imidazole-4-carboxylate (6.45 mmol, 1 g) and triethylamine (10.04 mmol, 1.016 g) were suspended in dry ACN (30 ml) and cooled to 0° C. Acryloyl chloride (9.67 mmol, 0.875 g) dissolved in dry ACN (4 ml) was added dropwise. The resulting mixture was slowly warmed to RT and subsequently heated to 50° C. for 16 h. The solvent was evaporated and the residue purified by flash chromatography. 0.358 g of the title compound was obtained. $^1$H-NMR (400 MHz, CDCl$_3$): δ 1.37 (t, 3H), 2.92 (t, 2H), 4.18 (t, 2H), 4.37 (q, 2H), 7.40 (s, 1H), 8.78 (bs, 1H).

b) 7-Oxo-5,6,7,8-tetrahydroimidazo[1,2-a]pyrimidine-2-carboxylic acid

Ethyl 7-oxo-5,6,7,8-tetrahydroimidazo[1,2-a]pyrimidine-2-carboxylate (1.711 mmol, 0.358 g) was dissolved in ethanol (5 ml) and cooled to 0° C. 1N solution of NaOH (5 ml) was slowly added. The resulting mixture was heated to 60° C. for 1.5 h. Ethanol was evaporated, the residue diluted with tert-butyl methyl ether and acidified with 2 N HCl solution under cold conditions. The mixture was stirred for overnight. DCM and water was added and the precipitate was filtered. Phases in the filtrate were separated and the water phase was evaporated. The residue from water and precipitate were combined. 0.592 g of the title compound was obtained. $^1$H-NMR (400 MHz, DMSO-$d_6$): δ 2.73 (t, 2H), 4.12 (t, 2H), 7.58 (s, 1H), 11.09 (bs, 1H).

c) (S)—N-(1-(3-(3-Chloro-4-cyano-5-fluorophenyl)-1H-pyrazol-1-yl)propan-2-yl)-7-oxo-5,6,7,8-tetrahydroimidazo[1,2-a]pyrimidine-2-carboxamide 7-Oxo-5,6,7,8-tetrahydroimidazo[1,2-a]pyrimidine-2-carboxylic acid (1.513 mmol, 0.274 g) was dissolved in DMF (5 ml) under nitrogen atmosphere. EDCI (1.891 mmol, 0.362 g), DIPEA (3.78 mmol, 0.489 g) and HOBt (1.891 mmol, 0.255 g) were added and the resulting mixture was stirred for 20 min at RT. (S)-4-(1-(2-Aminopropyl)-1H-pyrazol-3-yl)-2-chloro-6-fluorobenzonitrile (1.260 mmol, 0.351 g) dissolved in DMF (5 ml) was added and the resulting mixture was stirred at RT for 2 days. The mixture was diluted with water and EtOAc, washed with 2M Na$_2$CO$_3$, water and brine. The combined organics were dried, filtered and evaporated. The crude product was purified by preparative HPLC. 0.0089 g of the title compound was obtained. $^1$H-NMR (400 MHz, CDCl$_3$): δ 1.28 (d, 3H), 2.89 (t, 2H), 4.16 (t, 2H), 4.33-4.39 (m, 2H), 4.54-4.65 (m, 1H), 6.59 (d, 1H), 7.36 (s, 1H), 7.53 (d, 1H), 7.57 (dd, 1H), 7.72-7.75 (m, 1H), 7.83 (d, 1H).

Example 5

(S)—N-(1-(3-(3-Chloro-4-cyano-5-fluorophenyl)-1H-pyrazol-1-yl)propan-2-yl)-3-isopropyl-1,2,4-oxadiazole-5-carboxamide a) Ethyl 3-isopropyl-1,2,4-oxadiazole-5-carboxylate (E)-N'-hydroxyisobutyrimidamide (27.6 mmol, 2.82 g) was dissolved in pyridine (10 ml) and cooled to 0° C. Ethyl oxalyl chloride (35.9 mmol, 4.90 g) was added dropwise to the previous mixture and stirred for 10 min at 0° C., warmed to RT and later heated to 70° C. for 1.5 h. The mixture was poured to ice-cold water. The residue was extracted twice with t-butyl methyl ether and water. The organic phase was dried, filtered and evaporated. The crude product was purified by flash chromatography. 1.919 g of the title compound was obtained. $^1$H-NMR (400 MHz, CDCl$_3$): δ 1.39 (d, 6H), 1.47 (t, 3H), 3.14-3.28 (m, 1H), 4.54 (q, 2H).

b) 3-Isopropyl-1,2,4-oxadiazole-5-carboxylic acid

Ethyl 3-isopropyl-1,2,4-oxadiazole-5-carboxylate (10.42 mmol, 1.919 g) was dissolved in EtOH (20 ml). Sodium hydroxide pellets (12.50 mmol, 0.500 g) were dissolved in cold water (10 ml) and solution slowly added. The resulting solution was heated at 60° C. for 1.5 h. EtOH was removed under vacuum. The residue was diluted with tert-butyl methyl ether. The mixture was acidified under cold conditions by adding 2 N HCl solution. The mixture was stirred overnight and washed with DCM. Water phase was evaporated precipitating the product. 1.673 g of the title compound was obtained. $^1$H-NMR (400 MHz, D$_2$O): δ 1.33 (d, 6H), 3.10-3.25 (m, 1H).

c) (S)—N-(1-(3-(3-Chloro-4-cyano-5-fluorophenyl)-1H-pyrazol-1-yl)propan-2-yl)-3-isopropyl-1,2,4-oxadiazole-5-carboxamide 3-Isopropyl-1,2,4-oxadiazole-5-carboxylic acid (1.281 mmol, 0.2 g) was dissolved in DMF (5 ml) under nitrogen atmosphere. EDCI (1.601 mmol, 0.307 g), DIPEA (3.20 mmol, 0.414 g) and HOBt (1.601 mmol, 0.216 g) were added and the resulting mixture was stirred for 20 min at RT. (S)-4-(1-(2-Aminopropyl)-1H-pyrazol-3-yl)-2-chloro-6-fluorobenzonitrile (1.067 mmol, 0.298 g) dissolved in DMF (5 ml) was added and the resulting mixture was stirred at RT for 2 days. The mixture was diluted with water and EtOAc, washed with 2 M Na$_2$CO$_3$, water and brine. The combined organics were dried, filtered and evaporated. The crude product was purified by preparative HPLC. 0.0056 g of the title compound was obtained. $^1$H-NMR (400 MHz, CDCl$_3$): δ 1.25 (d, 3H), 1.38 (d, 6H), 3.11-3.26 (m, 1H), 4.26-4.35 (m, 1H), 4.41-4.50 (m, 1H), 4.55-4.67 (m, 1H), 6.65-6.69 (m, 1H), 7.54-7.57 (m, 1H), 7.64-7.69 (m, 1H), 7.74-7.77 (m, 1H), 8.39 (d, 1H).

Example 6

(S)—N-(1-(3-(3-Chloro-4-cyano-5-fluorophenyl)-1H-pyrazol-1-yl)propan-2-yl)-5,7-dimethylimidazo[1,2-c]pyrimidine-2-carboxamide a) Ethyl 5,7-dimethylimidazo[1,2-c]pyrimidine-2-carboxylate 4-Amino-2,6-dimethylpyrimidine (16.24 mmol, 2 g) was mixed with ethanol (30 ml) and stirred well. Ethyl bromopyruvate (20.30 mmol, 3.96 g) was added in small portions. The resulting mixture was refluxed for 5.5 h and stirred at RT overnight. The solvent was evaporated, DCM was added and washed with Na$_2$HCO$_3$. The organic phase was dried, filtered and evaporated. The crude product was purified by flash chromatography and trituration from EtOAc/heptane, respectively. 0.287 g of the title product was obtained. $^1$H-NMR (400 MHz, DMSO-d$_6$): δ 1.33 (t, 3H), 2.42 (d, 3H), 2.80 (s, 3H), 4.33 (q, 2H), 7.32 (s, 1H), 8.50 (d, 1H).

b) 5,7-Dimethylimidazo[1,2-c]pyrimidine-2-carboxylic acid

Ethyl 5,7-dimethylimidazo[1,2-c]pyrimidine-2-carboxylate (1.268 mmol, 0.278 g) was dissolved in ethanol (10 ml) and cooled to 0° C. 2 M NaOH solution was added to the reaction mixture. The resulting mixture was stirred at 0° C. for 30 min and for an hour at RT. The solvent was evaporated and water added to the residue. The water phase was made acidic with 1 M HCl and extracted three times with EtOAc. The combined organics were dried, filtered and evaporated. 0.292 g of the title compound was obtained. $^1$H-NMR (400 MHz, DMSO-d$_6$): δ 2.46 (s, 3H), 2.83 (s, 3H), 7.39 (s, 1H), 8.57 (s, 1H).

c) (S)—N-(1-(3-(3-Chloro-4-cyano-5-fluorophenyl)-1H-pyrazol-1-yl)propan-2-yl)-5,7-dimethylimidazo[1,2-c]pyrimidine-2-carboxamide The title compound was prepared using the procedure described in Example 3(h) starting from 5,7-dimethyl-imidazo[1,2-c]pyrimidine-2-carboxylic acid (0.753 mmol, 0.144 g) and (S)-4-(1-(2-aminopropyl)-1H-pyrazol-3-yl)-2-chloro-6-fluoro-benzonitrile (0.538 mmol, 0.2 g). DMF (6 ml) was used as a solvent and HBTU (0.054 mmol, 0.020 g) was used instead of HOBt. The crude product was purified by trituration from ACN. 0.045 g of the title compound was obtained. $^1$H-NMR (400 MHz, CDCl$_3$): δ 1.26 (d, 3H), 2.53-2.56 (m, 3H), 2.82 (s, 3H), 4.30 (dd, 1H), 4.48 (dd, 1H), 4.60-4.72 (m, 1H), 6.63 (d, 1H), 7.23-7.26 (m, 1H), 7.52 (d, 1H), 7.75-7.83 (m, 2H), 8.00-8.06 (m, 1H), 8.27 (d, 114).

Example 7

(S)-5-((1H-Imidazol-1-yl)methyl)-N-(1-(3-(3-chloro-4-cyano-5-fluorophenyl)-1H-pyrazol-1-yl)propan-2-yl)isoxazole-3-carboxamide a) 5-(Bromomethyl)isoxazole-3-carboxylic acid Ethyl 5-(bromomethyl)isoxazole-3-carboxylate (4.27 mmol, 1 g) and lithium hydroxide (10.68 mmol, 0.256 g) were dissolved in THF (6.5 ml) and water (6.5 ml). The resulting mixture was stirred for 30 min at RT. The pH was adjusted to 4 with 1 M HCl and diluted with water. The mixture was extracted three times with EtOAc. The combined organics were dried, filtered and evaporated. 0.543 g of the title compound was obtained. $^1$H-NMR (400 MHz, DMSO-d$_6$): δ 4.88 (s, 2H), 6.92 (s, 1H), 14.09 (bs, 1H).

b) (S)-5-(Bromomethyl)-N-(1-(3-(3-chloro-4-cyano-5-fluorophenyl)-1H-pyrazol-1-yl)propan-2-yl)isoxazole-3-carboxamide 5-(Bromomethyl)isoxazole-3-carboxylic acid (0.718 mmol, 0.148 g) was dissolved in DCM (5 ml) and THF (1 ml). 1,3-Dicyclohexylcarbodiimide (0.718 mmol, 0.148 g) was added and the resulting mixture was stirred at RT. The precipitate formed was filtered and (S)-4-(1-(2-aminopropyl)-1H-pyrazol-3-yl)-2-chloro-6-fluorobenzonitrile (0.359 mmol, 0.1 g), triethylamine (0.359 mmol, 0.036 g) and dry DCM (5 ml) was added to the filtrate. The filtrate was stirred at RT under nitrogen atmosphere for two days during which more 1,3-dicyclohexylcarbodiimide (0.148 g), triethylamine (0.050 ml) and 5-(bromomethyl)isoxazole-3-carboxylic acid (0.1 g) were added. The reaction mixture was diluted with DCM and washed with NaHCO$_3$. The organic phase was dried, filtered and evaporated. The crude product was purified with flash chromatography. 0.064 g of the title compound was obtained. $^1$H-NMR (400 MHz, CDCl$_3$): δ 1.25 (d, 3H), 4.00-4.09 (m, 2H), 4.23-4.31 (m, 1H), 4.41-4.48 (m, 1H), 4.53-4.63 (m, 1H), 6.60-6.66 (m, 1H), 6.74-6.78 (m, 1H), 7.48-7.53 (m, 1H), 7.64 (d, 1H), 7.79-7.88 (m, 2H).

c) (S)-5-((1H-Imidazol-1-yl)methyl)-N-(1-(3-(3-chloro-4-cyano-5-fluorophenyl)-1H-pyrazol-1-yl)propan-2-yl)isoxazole-3-carboxamide (S)-5-(Bromomethyl)-N-(1-(3-(3-chloro-4-cyano-5-fluorophenyl)-1H-pyrazol-1-yl)propan-2-yl)isoxazole-3-carboxamide (0.137 mmol, 0.064 g) was suspended in DMF (5 ml). Imidazole (2.74 mmol, 0.187 g) was added and the resulting mixture was stirred at RT for 2.5 h. The reaction mixture was heated to 60° C. for 1.5 h. The mixture was diluted with EtOAc and washed four times with water. The organic phase was dried, filtered and evaporated. The crude product was purified by preparative HPLC. 0.017 g of the title compound was obtained. $^1$H-NMR (400 MHz, DMSO-d$_6$): δ 1.15 (d, 3H), 4.31 (d, 2H), 4.37-4.50 (m, 1H), 5.50 (s, 2H), 6.63 (s, 1H), 6.94 (s, 1H), 6.99 (d, 1H), 7.22-7.24 (m, 1H), 7.76 (s, 1H), 7.83 (d, 1H), 7.84-7.88 (m, 1H), 7.96 (s, 1H), 8.81 (d, 1H).

Example 8

(S)—N-(1-(3-(3-Chloro-4-cyano-5-fluorophenyl)-1H-pyrazol-1-yl)propan-2-yl)-5-oxo-5,6-dihydroimidazo[1,2-c]pyrimidine-2-carboxamide a) ethyl 5-oxo-5,6-dihydroimidazo[1,2-c]pyrimidine-2-carboxylate Ethyl bromopyruvate (18.00 mmol, 3.51 g) was dissolved in ethanol (50 ml). Cytosine (18.00 mmol, 2 g) was added and the resulting mixture was refluxed for 5.5 h. The mixture was evaporated and DCM was added. The precipitate was filtered and washed with water. The filtrate was washed with NaHCO$_3$, water and evaporated. The evaporation residue and the previously filtered precipitate were purified by flash chromatography and trituration from water, respectively. 0.526 g of the title compound was obtained. $^1$H-NMR (400 MHz, DMSO-d$_6$): δ 1.31 (t, 3H), 4.29 (q, 2H), 6.60 (d, 1H), 7.30-7.38 (m, 1H), 8.22 (s, 1H), 11.77 (bs, 1H).

b) 5-Oxo-5,6-dihydroimidazo[1,2-c]pyrimidine-2-carboxylic acid

Ethyl 5-oxo-5,6-dihydroimidazo[1,2-c]pyrimidine-2-carboxylate (2.510 mmol, 0.52 g) was suspended in ethanol (20 ml). Cesium carbonate (5.02 mmol, 1.635 g) dissolved in water (4 ml) was added and the resulting mixture was stirred at RT for 3.5 h after which the mixture was refluxed for 8 h. The ethanol was evaporated, and the residue was diluted with water. The pH was adjusted to 4 with 1 M HCl and the solvent was evaporated. The residue was purified by trituration from DMF. 0.137 g of the title compound was obtained. $^1$H-NMR (400 MHz, CDCl$_3$): δ 7.17-7.31 (m, 2H), 7.86-7.99 (m, 1H).

c) (S)—N-(1-(3-(3-Chloro-4-cyano-5-fluorophenyl)-1H-pyrazol-1-yl)propan-2-yl)-5-oxo-5,6-dihydroimidazo[1,2-c]pyrimidine-2-carboxamide 5-Oxo-5,6-dihydroimidazo[1,2-c]pyrimidine-2-carboxylic acid (0.323 mmol, 0.058 g), HBTU (0.027 mmol, 10.21 mg), DIPEA (0.323 mmol, 0.042 g) and EDCI (0.323 mmol, 0.062 g) were suspended in DMF (2 ml) and the resulting mixture was stirred at RT for 10 min. (S)-4-(1-(2-Aminopropyl)-1H-pyrazol-3-yl)-2-chloro-6-fluorobenzonitrile (0.269 mmol, 0.1 g) dissolved in DMF (2 ml) was added and the resulting mixture was stirred for 17 h at RT. At this point more starting materials were added so that the amount of every starting material was raised by half of the original amount. The amount of (S)-4-(1-(2-aminopropyl)-1H-pyrazol-3-yl)-2-chloro-6-fluorobenzonitrile was not changed. The reaction was continued for another 22 h after which the temperature was raised to 80° C. for 4.5 h. The reaction mixture was diluted with EtOAc and washed with 1M Na$_2$CO$_3$, brine and water. The organic phase was dried, filtered and evaporated. The crude product was purified by preparative HPLC. 0.006 g of the title compound was obtained. $^1$H-NMR (400 MHz, MeOH-d$_4$): δ 1.25 (d, 3H), 4.30-4.37 (m, 1H), 4.42-4.49 (m, 1H), 4.54-4.65 (m, 1H), 6.61 (dd, 1H), 6.70 (d, 1H), 7.18 (d, 1H), 7.63 (d, 1H), 7.75-7.82 (m, 2H), 8.26 (s, 1H).

Example 9

(S)—N-(1-(3-(3-Chloro-4-cyano-5-fluorophenyl)-1H-pyrazol-1-yl)propan-2-yl)-1,6-dihydropyrrolo[2,3-c]pyrazole-5-carboxamide a) Ethyl 1,6-dihydropyrrolo[2,3-c]pyrazole-5-carboxylate 3-Aminopyrazole (1.203 mmol, 0.1 g), ethyl bromopyruvate (1.504 mmol, 0.293 g) and methanol were added into a flask and refluxed for 1.5 h. The solvent was evaporated and the residue was dissolved in DCM and washed with Na$_2$HCO$_3$. The organic phase was dried, filtered and evaporated. 0.238 g of the title compound was obtained. $^1$H-NMR (400 MHz, DMSO-d$_6$): δ 1.30 (t, 3H), 4.26 (q, 2H), 6.76 (d, 1H), 7.68 (s, 1H).

b) 1,6-Dihydropyrrolo[2,3-c]pyrazole-5-carboxylic acid

Ethyl 1,6-dihydropyrrolo[2,3-c]pyrazole-5-carboxylate (1.328 mmol, 0.238 g) was dissolved in ethanol (10 ml). Cesium carbonate (2.66 mmol, 0.866 g) dissolved in water (2 ml) was added and the resulting mixture was stirred at RT for a day after which more cesium carbonate (2.66 mmol, 0.866 g) dissolved in water (2 ml) was added. The temperature was raised to 80° C. for 7 h. Ethanol was evaporated and the residue was diluted with water. pH was adjusted to 4 with 2 M HCl and extracted three times with EtOAc and washed with water. The combined organics were dried, filtered and evaporated. 0.041 g of the title compound was obtained. LC-MS [M+1]: 152.

c) (S)—N-(1-(3-(3-Chloro-4-cyano-5-fluorophenyl)-1H-pyrazol-1-yl)propan-2-yl)-1,6-dihydropyrrolo[2,3-c]pyrazole-5-carboxamide The title compound was prepared using the procedure described in Example 3(h), starting from 1,6-dihydropyrrolo[2,3-c]pyrazole-5-carboxylic acid (0.280 mmol, 0.042 g) and (S)-4-(1-(2-aminopropyl)-1H-pyrazol-3-yl)-2-chloro-6-fluorobenzo-nitrile (0.215 mmol, 0.080 g). The crude product was purified by preparative HPLC. 0.0164 g of the title compound was obtained. $^1$H-NMR (400 MHz, MeOH-d$_4$): δ 1.29 (d, 3H), 4.27-4.34 (m, 1H), 4.36-4.43 (m, 1H), 4.50-4.60 (m, 1H), 6.75-6.79 (m, 2H), 7.58 (s, 1H), 7.60-7.65 (m, 1H), 7.69 (d, 1H), 7.79-7.82 (m, 1H).

Example 10

(S)—N-(1-(3-(3-Chloro-4-cyano-5-fluorophenyl)-1H-pyrazol-1-yl)propan-2-yl)imidazo[2,1-b]thiazole-6-carboxamide The title compound was prepared using the procedure described in Example 3(h) starting from imidazo[2,1-b]thiazole-6-carboxylic acid (1.041 mmol, 0.175 g) and (S)-4-(1-(2-aminopropyl)-1H-pyrazol-3-yl)-2-chloro-6-fluorobenzonitrile (1.041 mmol, 0.290 g). DMF (10 ml) was used as the solvent and the reaction time was 2 days. The work up was done by diluting the reaction mixture with water and ethyl acetate and washing it with 2M Na$_2$CO$_3$, water and brine. The combined organics were dried, filtered and eveaporated. The crude product was purified by flash chromatography. 0.186 g of the title compound was obtained. $^1$H-NMR (400 MHz, MeOH-d$_4$): δ 1.24 (d, 3H), 4.32-4.39 (m, 1H), 4.40-4.47 (m, 1H), 4.53-4.61 (m, 1H), 6.79 (d, 1H), 7.20 (d, 1H), 7.73 (d, 1H), 7.76 (d, 1H), 7.77-7.81 (m, 1H), 7.89-7.91 (m, 1H), 8.10 (s, 1H).

Example 11

(S)—N-(1-(3-(3-Chloro-4-cyano-5-fluorophenyl)-1H-pyrazol-1-yl)propan-2-yl)-6-nitroimidazo[1,2-a]pyridine-2-carboxamide The title compound was prepared using the procedure described in Example 3(h) starting from 6-nitroimidazo[1,2-a]pyridine-2-carboxylic acid (0.551 mmol, 0.114 g) and (S)-4-(1-(2-aminopropyl)-1H-pyrazol-3-yl)-2-chloro-6-fluorobenzo-nitrile (0.459 mmol, 0.128 g). DMF (4 ml) was used as the solvent and HBTU (0.046 mmol, 0.017 g) was used instead of HOBt. The crude product was purified by preparative HPLC. 0.0405 g of the title compound was obtained. $^1$H-NMR (400 MHz, MeOH-d$_4$): δ 1.37 (d, 3H), 4.30-4.37 (m, 1H), 4.38-4.46 (m, 1H), 4.59-4.72 (m, 1H), 6.72 (d, 1H), 7.54 (d, 1H), 7.68 (d, 1H), 7.72 (s, 1H), 7.78 (d, 1H), 8.15-8.21 (m, 1H), 8.38 (s, 1H), 10.40-10.44 (m, 1H).

Example 12

(S)—N-(1-(3-(3-Chloro-4-cyano-5-fluorophenyl)-1H-pyrazol-1-yl)propan-2-yl)-5,6,7,8-tetrahydroimidazo[1,2-a]pyridine-2-carboxamide The title compound was prepared using the procedure described in Example 3(h) starting from 5,6,7,8-tetrahydroimidazo[1,2-a]pyridine-2-carboxylic acid (2.58 mmol, 428 mg) and (S)-4-(1-(2-aminopropyl)-1H-pyrazol-3-yl)-2-chloro-6-fluoro-benzonitrile (1.717 mmol, 479 mg). DMF (10 ml) was used as the solvent. The reaction mixture was diluted with water and extracted three times with DCM. The combined organics were washed twice with water. The organic phase was evaporated. The crude product was purified by flash chromatography. 515 mg of the title compound was obtained. $^1$H-NMR (400 MHz, DMSO-d$_6$): δ 1.07 (d, 3H), 1.78-1.94 (m, 4H), 2.76 (t, 2H), 3.95 (t, 2H), 4.24-4.31 (m, 1H), 4.33-4.46 (m, 2H), 7.01 (d, 1H), 7.43 (s, 1H), 7.84 (d, 1H), 7.90-7.95 (m, 1H), 8.00 (s, 1H), 8.08 (d, 1H).

Example 13

(S)—N-(1-(3-(3-Chloro-4-cyano-5-fluorophenyl)-1H-pyrazol-1-yl)-propan-2-yl)-1-isopropyl-2-methyl-1H-imidazole-4-carboxamide a) Ethyl 1-isopropyl-2-methyl-1H-imidazole-4-carboxylate Ethyl 2-methyl-1H-imidazole-4-carboxylate (0.649 mmol, 100 mg) and KOH (0.973 mmol, 54.6 mg) were dissolved in DMF (2 ml) under nitrogen atmosphere. 2-Iodopropane(isopropyliodide), stabilized over copper (+98%, 0.973 mmol, 165 mg) was added and the resulting mixture was stirred at RT overnight. NH$_4$Cl solution was added and the mixture was extracted three times with EtOAc. The combined organics were washed with water, dried, filtered and evaporated. The crude product was purified by flash chromatography. 83 mg of the title compound was obtained. $^1$H-NMR (400 MHz, DMSO-d$_6$): δ 1.25 (t, 3H), 1.36 (d, 6H), 2.32 (s, 3H), 4.18 (q, 2H), 4.31-4.43 (m, 1H), 7.87 (s, 1H).

b) 1-Isopropyl-2-methyl-1H-imidazole-4-carboxylic acid

Ethyl 1-isopropyl-2-methyl-1H-imidazole-4-carboxylate (0.423 mmol, 83 mg) was dissolved in methanol (0.5 ml) and THF (4 ml). NaOH 2 M (2.115 mmol, 1.057 ml) was added and the resulting mixture was stirred at RT overnight. The pH of the reaction mixture was adjusted to about 5 with 1 M HCl and the mixture was evaporated. Ethanol was added and the salt was removed by filtration. The salt was flushed few times with ethanol. 51 mg of the title compound was obtained. $^1$H-NMR (400 MHz, DMSO-d$_6$): δ 1.38 (d, 6H), 2.39 (s, 3H), 4.35-4.49 (m, 1H), 7.97 (s, 1H).

c) (S)—N-(1-(3-(3-Chloro-4-cyano-5-fluorophenyl)-1H-pyrazol-1-yl)propan-2-yl)-1-isopropyl-2-methyl-1H-imidazole-4-carboxamide The title compound was prepared using the procedure described in Example 3(h) using 1-isopropyl-2-methyl-1H-imidazole-4-carboxylic acid (0.303 mmol, 51 mg), (S)-4-(1-(2-aminopropyl)-1H-pyrazol-3-yl)-2-chloro-6-fluorobenzonitrile (0.253 mmol, 70.4 mg) and only a catalytic amount of HOBt (0.025 mmol, 3.41 mg). DMF (2 ml) was used as the solvent in the reaction. The work up was done by adding water to the reaction mixture and extracting it three times with DCM. The combined organics were washed twice with water. The organic phase was evaporated and the residue was purified by flash chromatography. 86 mg of the title compound was obtained. $^1$H-NMR (400 MHz, DMSO-d$_6$): δ 1.06 (d, 3H), 1.34 (d, 6H), 2.35 (s, 3H), 4.23-4.47 (m, 4H), 7.02 (d, 1H), 7.62 (s, 1H), 7.86 (d, 1H), 7.90-7.96 (m, 1H), 8.00 (s, 1H), 8.04 (d, 1H).

Example 14

(S)—N-(1-(3-(3-Chloro-4-cyano-5-fluorophenyl)-1H-pyrazol-1-yl)propan-2-yl)-5-(2-hydroxypropan-2-yl)-1H-pyrazole-3-carboxamide a) Ethyl 5-(2-hydroxypropan-2-yl)-1H-pyrazole-3-carboxylate Zinc trifluoromethanesulfonate (2.378 mmol, 0.864 g), 2-methyl-3-butyn-2-ol (11.89 mmol, 1 g) and triethylamine (17.83 mmol, 1.804 g) were added into a flask under nitrogen atmosphere. Ethyl diazoacetate (14.27 mmol, 1.628 g) was added slowly and the temperature was carefully raised to 100° C. and stirred for 8 h. Water was added and the mixture was extracted twice with DCM. The combined DCM phases were dried, filtered and evaporated. The crude product was purified by flash chromatography. 0.658 g of the title compound was obtained. $^1$H-NMR (400 MHz, DMSO-d$_6$): δ 1.28 (t, 3H), 1.45 (s, 6H), 4.24 (q, 2H), 5.34 (s, 1H), 6.52 (s, 1H), 13.22 (bs, 1H).

b) 5-(2-Hydroxypropan-2-yl)-1H-pyrazole-3-carboxylic acid

Ethyl 5-(2-hydroxypropan-2-yl)-1H-pyrazole-3-carboxylate (1.609 mmol, 0.319 g) was dissolved in ethanol (1 ml) and THF (4 ml). 2 M NaOH (8.05 mmol, 4.02 ml) was added and the resulting mixture was stirred overnight at RT. The reaction mixture was carefully neutralized with HCl and evaporated. The residue was dissolved in a small amount of ethanol and the salts were removed by filtration. The filtrate was evaporated. 0.227 g of the title compound was obtained. $^1$H-NMR (400 MHz, DMSO-d$_6$): δ 1.39 (s, 6H), 4.72 (bs, 1H), 6.24 (s, 1H), 12.20 (bs, 1H).

c) (S)—N-(1-(3-(3-Chloro-4-cyano-5-fluorophenyl)-1H-pyrazol-1-yl)propan-2-yl)-5-(2-hydroxypropan-2-yl)-1H-pyrazole-3-carboxamide The title compound was prepared using the procedure described in Example 3(h) using 5-(2-hydroxypropan-2-yl)-1H-pyrazole-3-carboxylic acid (0.646 mmol, 110 mg) and (S)-4-(1-(2-amino-propyl)-1H-pyrazol-3-yl)-2-chloro-6-fluorobenzo-nitrile (0.539 mmol, 150 mg) and only a catalytic amount of HOBt (0.054 mmol, 7.28 mg). DMF was used as the solvent. Water was added to the reaction mixture and the mixture was extracted it three times with DCM. The combined organics were washed twice with water. The organic phase was evaporated and the residue was purified by flash chromatography and preparative HPLC, respectively. 45.4 mg of the title compound was obtained. $^1$H-NMR (400 MHz, DMSO-d$_6$): δ 1.13 (d, 3H), 1.43 (s, 6H), 4.17-4.55 (m, 3H), 5.27 (bs, 1H), 6.37 (bs, 1H), 6.99 (d, 1H), 7.82 (d, 1H), 7.86 (d, 1H), 7.97 (s, 1H), 8.08 (bs, 1H), 12.94 (bs, 1H).

Example 15

(S)—N-(1-(3-(3-Chloro-4-cyano-5-fluorophenyl)-1H-pyrazol-1-yl)-propan-2-yl)-1-(2,2-difluoroethyl)-2-methyl-1H-imidazole-4-carboxamide a) Ethyl 1-(2,2-difluoroethyl)-2-methyl-1H-imidazole-4-carboxylate Ethyl 2-methyl-1H-imidazole-4-carboxylate (1.622 mmol, 250 mg) and KOH (2.432 mmol, 136 mg) were suspended in DMF (2 ml). 1,1-Difluoro-2-iodoethane (4.86 mmol, 934 mg) was added and the resulting mixture was stirred overnight at RT. During the stirring additional 0.3 ml of 1,1-difluoro-2-iodoethane was added to complete the reaction. Aqueous NH$_4$Cl solution was added and the mixture was extracted three times with EtOAc. The combined organics were washed with water, dried, filtered and evaporated. The crude product was purified by flash chromatography. 0.3 g of the title compound was obtained. Two isomers were obtained in the reaction and separated in later steps. Isomer 1: $^1$H-NMR (400 MHz, DMSO-d$_6$): δ 1.28 (t, 3H), 2.33 (s, 3H), 4.25 (q, 2H), 4.45-4.58 (m, 2H), 6.23-6.53 (m, 1H), 7.80 (s, 1H). Isomer 2: $^1$H-NMR (400 MHz, DMSO-d$_6$): δ 1.25 (t, 3H), 2.39 (s, 3H), 4.19 (q, 2H), 4.70-4.83 (m, 2H), 6.18-6.49 (m, 1H), 7.59 (s, 1H).

b) 1-(2,2-Difluoroethyl)-2-methyl-1H-imidazole-4-carboxylic acid

Ethyl 1-(2,2-difluoroethyl)-2-methyl-1H-imidazole-4-carboxylate (1.375 mmol, 300 mg) was dissolved in methanol (0.5 ml) and THF (4 ml). NaOH 2 M (4.12 mmol, 2.062 ml) was added and the resulting mixture was stirred for 2.5 h at RT. The pH of the mixture was adjusted to about 6 with 5 M HCl and the solvents were evaporated. Ethanol was added and filtered. The filtrate was evaporated. 176 mg of the title compound was obtained. The two isomers formed in the previous reaction were still present. Isomer 1: $^1$H-NMR (400 MHz, DMSO-d$_6$): δ 2.25 (s, 3H), 4.67-4.80 (m, 2H), 6.09-6.44 (m, 1H), 6.94 (s, 1H). Isomer 2: $^1$H-NMR (400 MHz, DMSO-d$_6$): δ 2.27 (s, 3H), 4.32-4.44 (m, 2H), 6.17-6.47 (m, 1H), 7.15 (s, 1H).

c) (S)—N-(1-(3-(3-Chloro-4-cyano-5-fluorophenyl)-1H-pyrazol-1-yl)propan-2-yl)-1-(2,2-difluoroethyl)-2-methyl-1H-imidazole-4-carboxamide The title compound was prepared using the procedure described in Example 3(h) using 1-(2,2-difluoro-ethyl)-2-methyl-1H-imidazole-4-carboxylic acid (0.926 mmol, 176 mg), (S)-4-(1-(2-aminopropyl)-1H-pyrazol-3-yl)-2-chloro-6-fluorobenzo-nitrile (0.617 mmol, 172 mg) and only a catalytic amount of HOBt (0.062 mmol, 8.34 mg). DMF was used as the solvent. Water was added to the reaction mixture and the mixture was extracted it three times with DCM. The combined organics were washed twice with water. The organic phase was evaporated and the residue was purified by flash chromatography and preparative HPLC, respectively. 15.5 mg of the title compound was obtained. $^1$H-NMR (400 MHz, DMSO-d$_6$): δ 1.07 (d, 3H), 2.36 (s, 3H), 4.23-4.55 (m, 5H), 6.19-6.51 (m, 1H), 7.02 (d, 1H), 7.53 (s, 1H), 7.86 (d, 1H), 7.90-7.95 (m, 1H), 8.00 (s, 1H), 8.12 (d, 1H).

Example 16

N—((S)-1-(3-(3-Chloro-4-cyano-5-fluorophenyl)-1H-pyrazol-1-yl)-propan-2-yl)-1-((R)-2-hydroxypropyl)-2-methyl-1H-imidazole-4-carboxamide a) (R)-Ethyl 1-(2-hydroxypropyl)-2-methyl-1H-imidazole-4-carboxylate Ethyl 2-methyl-1H-imidazole-4-carboxylate (3.24 mmol, 500 mg) and potassium carbonate (32.4 mmol, 4482 mg) were dissolved in DMF (10 ml). (R)-(+)-propylene oxide (48.6 mmol, 3.41 ml) was added and the resulting mixture was stirred at 60° C. for 5.5 h. More (R)-(+)-propylene oxide (1.5 ml) was added and the heating continued for another hour. The mixture was evaporated and the residue was purified by flash chromatography. 525 mg of the title compound was obtained. $^1$H-NMR (400 MHz, DMSO-d$_6$): δ 1.06 (d, 3H), 1.25 (t, 3H), 2.30 (s, 3H), 3.68-4.00 (m, 3H), 4.18 (q, 2H), 4.95 (d, 1H), 7.73 (s, 1H).

b) (R)-1-(2-Hydroxypropyl)-2-methyl-1H-imidazole-4-carboxylic acid (R)-Ethyl 1-(2-hydroxypropyl)-2-methyl-1H-imidazole-4-carboxylate (2.474 mmol, 525 mg) was dissolved in methanol (1 ml) and THF (8 ml). NaOH 2 M (7.42 mmol, 3.71 ml) was added and the resulting mixture was stirred overnight at RT. The pH of the mixture was adjusted to about 5 with 1M HCl and the solvents were evaporated. Ethanol was added and the salts were removed by filtration. The filtrate was evaporated. 393 mg of the title compound was obtained. $^1$H-NMR (400 MHz, DMSO-d$_6$): δ 1.03 (m, 6H), 2.30 (s, 3H), 3.71-3.80 (m, 1H), 3.81-3.97 (m, 2H), 4.95 (bs), 7.67 (s, 1H).

c) N—((S)-1-(3-(3-Chloro-4-cyano-5-fluorophenyl)-1H-pyrazol-1-yl)propan-2-yl)-1-((R)-2-hydroxypropyl)-2-methyl-1H-imidazole-4-carboxamide The title compound was prepared using the procedure described in Example 3(h) starting from (R)-1-(2-hydroxypropyl)-2-methyl-1H-imidazole-4-carboxylic acid (1.059 mmol, 195 mg) and (S)-4-(1-(2-aminopropyl)-1H-pyrazol-3-yl)-2-chloro-6-fluorobenzonitrile (0.882 mmol, 246 mg) and using dry DMF (2 ml) as the solvent. After the reaction was finished, DCM was added and the reaction mixture was concentrated. The crude product was purified by flash chromatography and preparative HPLC, respectively. 177.8 mg of the title compound was obtained. $^1$H-NMR (400 MHz, DMSO-d$_6$): δ 1.00-1.10 (m, 6H), 2.34 (s, 3H), 3.69-3.90 (m, 3H), 4.22-4.48 (m, 3H), 4.91 (d, 1H), 7.02 (d, 1H), 7.47 (s, 1H), 7.86 (d, 1H), 7.91-7.96 (m, 1H), 8.00 (s, 1H), 8.06 (d, 1H).

Example 17

(S)—N-(1-(3-(3-Chloro-4-cyano-5-fluorophenyl)-1H-pyrazol-1-yl)propan-2-yl)-1'-methyl-1'H-1,4'-bipyrazole-3-carboxamide a) Methyl 1'-methyl-1'H-1,4'-bipyrazole-3-carboxylate Into a solution of methyl 1H-pyrazole-3-carboxylate (10 g, 79.3 mmol) in DMF (80 ml), cuprous oxide (0.567 g, 3.96 mmol), salicylaldoxime (1.08 g, 7.93 mmol), Cs$_2$CO$_3$ (64.4 g, 198.4 mmol) and 1-methyl-4-iodo pyrazole (16.5 g, 79.9 mmol) were added and the mixture was stirred at 110° C. for 48 h. The reaction mixture was quenched with saturated solution of aqueous NaHCO$_3$ and extracted with EtOAc. The organic layer was concentrated and purified by flash-chromatography. Yield 2.9 g. 1H-NMR (400 MHz; DMSO-d6): δ 3.83 (s, 3H), 3.88 (s, 3H), 7.90 (s, 1H), 8.29 (d, 2H). LC-MS: [M+H]=207.

b) 1'-Methyl-1'H-1,4'-bipyrazole-3-carboxylic acid

The title compound was prepared using the procedure described in Example 33(c) starting from methyl 1'-methyl-1'H-1,4'-bipyrazole-3-carboxylate (2.9 g, 13.5 mmol). Yield 1.4 g. 1H-NMR (400 MHz; DMSO-d6): δ 3.88 (s, 3H), 6.87 (d, 1H), 7.88 (s, 1H), 8.25 (d, 2H), 12.8 (bs, 1H). LC-MS: [M+1]=193.19.

c) (S)—N-(1-(3-(3-Chloro-4-cyano-5-fluorophenyl)-1H-pyrazol-1-yl)propan-2-yl)-1'-methyl-1'H-1,4'-bipyrazole-3-carboxamide The title compound was prepared using the procedure described in Example 3(h) starting from 1'-methyl-1'H-[1,4'-bipyrazole]-3-carboxylic acid (0.861 mmol, 165 mg) and (S)-4-(1-(2-aminopropyl)-1H-pyrazol-3-yl)-2-chloro-6-fluorobenzo-nitrile (0.718 mmol, 200 mg) and using DMF (2 ml) as the solvent. DCM was added and the reaction mixture was evaporated. The residue was purified by flash chromatography. The purified product was dissolved in DCM and washed three times with 1 M NaHCO$_3$. The combined organics were evaporated. 134 mg of the title compound was obtained. $^1$H-NMR (400 MHz, DMSO-d$_6$): δ 1.15 (d, 3H), 3.88 (s, 3H), 4.28-4.42 (m, 2H), 4.42-4.52 (m, 1H), 6.75 (d, 1H), 7.01 (d, 1H), 7.81-7.88 (m, 3H), 7.94 (s, 1H), 8.13-8.17 (m, 2H), 8.18 (s, 1H).

Example 18

(S)—N-(1-(3-(3-Chloro-4-cyano-5-fluorophenyl)-1H-pyrazol-1-yl)propan-2-yl)-1H,2'H-3,3'-bipyrazole-5-carboxamide a) Ethyl 1H,2'H-3,3'-bipyrazole-5-carboxylate Pieces of sodium (0.26 g) were slowly added to ethanol (12 ml) with stirring until all sodium had dissolved. 1-(1H-Pyrazol-5-yl)ethanone (8.61 mmol, 0.948 g) and diethyl oxalate (8.61 mmol, 1.258 g) was added. The mixture was heated to 75° C. for 3 h after which the stirring continued at RT overnight. Hydrazine hydrochloride (8.61 mmol, 0.590 g) dissolved in water (6 ml) was added. The resulting mixture was again heated to 75° C. for 3 h. The mixture was cooled to RT and neutralized by adding 2 M NaOH. The mixture was extracted twice with EtOAc and the combined organics were washed with water and brine. The organic phase was dried, filtered and evaporated. The crude product was purified by flash chromatography. 0.404 g of the title compound was obtained. $^1$H-NMR (400 MHz, MeOH-d$_4$): δ 1.39 (t, 3H), 4.38 (q, 2H), 6.69 (d, 1H), 7.10 (bs, 1H), 7.70 (bs, 1H).

b) 1H,2'H-3,3'-Bipyrazole-5-carboxylic acid

Ethyl 1H,2'H-3,3'-bipyrazole-5-carboxylate (1.959 mmol, 0.404 g) was dissolved in ethanol (5 ml) and cooled in an ice bath. NaOH 1 M solution (1.959 mmol, 4 ml) was slowly added. The solution was heated to 60° C. for 1 h. Ethanol was removed under vacuum and the residue was diluted with tert-butyl methyl ether. The solution was again cooled with an ice bath and acidified with 2 N HCl solution. The solution was allowed to warm to ambient temperature and stirred overnight. Water and DCM was added and the phases were separated. Both phases were evaporated and combined. 0.551 g of the title compound was obtained. $^1$H-NMR (400 MHz, DMSO-d$_6$): δ 6.70 (d, 1H), 7.04 (s, 1H), 7.77 (d, 1H).

c) (S)—N-(1-(3-(3-Chloro-4-cyano-5-fluorophenyl)-1H-pyrazol-1-yl)propan-2-yl)-1H,2'H-3,3'-bipyrazole-5-carboxamide The title compound was prepared using the procedure described in Example 3(h) starting from 1H,2'H-3,3'-bipyrazole-5-carboxylic acid (2.245 mmol, 0.4 g) and (S)-4-(1-(2-aminopropyl)-1H-pyrazol-3-yl)-2-chloro-6-fluorobenzonitrile (1.871 mmol, 0.521 g) and using DMF (10 ml) as the solvent. Water was added to the reaction mixture and the mixture was extracted with EtOAc. The organic phase was washed with 2M Na$_2$CO$_3$, water and brine. The organic phase was dried, filtered and evaporated. The crude product was purified by flash chromatography and preparative HPLC, respectively. 0.1277 g of the title compound was obtained. $^1$H-NMR (400 MHz, DMSO-d$_6$): δ 1.19 (d, 3H), 4.27-4.56

(m, 3H), 6.64 (bs, 1H), 6.84 (bs, 1H), 6.98 (d, 1H), 7.77 (bs, 1H), 7.81-7.87 (m, 2H), 7.93-7.6 (m, 1H), 8.07 (br. s, 1H), 12.57-13.78 (m, 2H).

Example 19

N—((S)-1-(3-(3-Chloro-4-cyano-5-fluorophenyl)-1H-pyrazol-1-yl)-propan-2-yl)-1-((S)-2-hydroxypropyl)-2-methyl-1H-imidazole-4-carboxamide a) (S)-Ethyl 1-(2-hydroxypropyl)-2-methyl-1H-imidazole-4-carboxylate

Ethyl 2-methyl-1H-imidazole-4-carboxylate (1.622 mmol, 250 mg) and potassium carbonate (16.22 mmol, 2241 mg) were dissolved in dry DMF (5 ml) under nitrogen atmosphere. (S)-2-methyloxirane (24.32 mmol, 1.723 ml) was added and the resulting mixture was heated to 60° C. and stirred for 5.5 h. More (S)-2-methyloxirane (1 ml) was added and the stirring continued at 60° C. for one additional hour. The solvent was evaporated. The crude product was purified by flash chromatography. 139 mg of the title compound was obtained. $^1$H-NMR (400 MHz, DMSO-d$_6$): δ 1.06 (d, 3H), 1.24 (t, 3H), 2.30 (s, 3H), 3.71-3.89 (m, 4H), 4.18 (q, 2H), 7.73 (s, 1H).

b) (S)-1-(2-Hydroxypropyl)-2-methyl-1H-imidazole-4-carboxylic acid (S)-Ethyl 1-(2-hydroxypropyl)-2-methyl-1H-imidazole-4-carboxylate (0.655 mmol, 139 mg) was dissolved in methanol (0.5 ml) and THF (4 ml). NaOH 2 M (1.965 mmol, 0.982 ml) was added and the resulting mixture was stirred overnight at RT. The mixture was acidified (pH-5) with 1 M HCl and evaporated. Ethanol was added and the salts were removed by filtration. The filtrate was evaporated. 112 mg of the title compound was obtained. $^1$H-NMR (400 MHz, DMSO-d$_6$): δ 1.06 (d, 3H), 2.30 (s, 3H), 3.70-3.91 (m, 4H), 7.59 (s, 1H).

b) N—((S)-1-(3-(3-Chloro-4-cyano-5-fluorophenyl)-1H-pyrazol-1-yl)propan-2-yl)-1-((S)-2-hydroxypropyl)-2-methyl-1H-imidazole-4-carboxamide The title compound was prepared using the procedure described in Example 3(h) starting from (S)-1-(2-hydroxypropyl)-2-methyl-1H-imidazole-4-carboxylic acid (0.608 mmol, 112 mg) and (S)-4-(1-(2-aminopropyl)-1H-pyrazol-3-yl)-2-chloro-6-fluorobenzonitrile (0.507 mmol, 141 mg) using DMF (2 ml) as the solvent. After the reaction had stopped, DCM was added and the reaction mixture was evaporated. The residue was purified by flash chromatography. The purified product was dissolved in a mixture of MeOH/DCM and washed twice with 1M NaHCO$_3$. The organic phase was dried, filtered and evaporated. The product was further purified by trituration from diethyl ether, filtered and dried with vacuum. 31 mg of the title compound was obtained. $^1$H-NMR (400 MHz, DMSO-d$_6$): δ 1.01-1.08 (m, 6H), 2.33 (s, 3H), 3.68-3.91 (m, 3H), 4.22-4.48 (m, 3H), 4.91 (d, 1H), 7.02 (d, 1H), 7.47 (s, 1H), 7.86 (d, 1H), 7.94 (d, 1H), 8.01 (s, 1H), 8.06 (d, 1H).

Example 20

(S)—N-(1-(3-(3-Chloro-4-cyano-5-fluorophenyl)-1H-pyrazol-1-yl)propan-2-yl)-3,3'-bipyridine-6-carboxamide a) tert-Butyl 5-bromopicolinate

5-Bromopicolinic acid (5 g, 24.8 mmol) was dissolved in t-BuOH (100 ml). To the solution, DMAP (0.303 g, 2.47 mmol), (Boc)$_2$O (8.1 g, 37.12 mmol) were added and stirred at 50° C. overnight. The solvent was concentrated under reduced pressure. The residue was diluted with H$_2$O and extracted with EtOAc. The organic layer was concentrated. Yield 3.6 g. $^1$H-NMR (400 MHz; DMSO-d$_6$): δ 1.55 (s, 9H), 7.92 (d, 1H), 8.23 (dd, 1H), 8.83 (d, 1H).

b) tert-Butyl 3,3'-bipyridine-6-carboxylate

Into a solution of tert-butyl 5-bromopicolinate (3.5 g, 13.56 mmol) in DMF (40 ml) Pd(OAc)$_2$ (0.152 g, 0.68 mmol), dppf (0.753 g, 1.37 mmol), CuCl (1.4 g, 13.57 mmol), Cs$_2$CO$_3$ (8.9 g, 27.13 mmol) and pyridin-3-yl boronic acid (3.4 g, 27.13 mmol) were added under inert atmosphere. The reaction mixture was stirred at 110° C. overnight and diluted with H$_2$O. The mixture was filtered through a celite bed, and the filtrate was extracted with EtOAc. The organic layer was concentrated. Yield 1.75 g. $^1$H-NMR (400 MHz; CDCl$_3$): δ 1.67 (s, 9H), 7.43-7.47 (m, 1H), 7.91 (d, J=8.0 Hz, 1H), 8.01 (dd, 1H), 8.17 (d, 1H), 8.70 (dd, 1H), 8.88 (d, 1H), 8.97 (d, 1H).

c) 3,3'-Bipyridine-6-carboxylic acid

A solution of tert-butyl 3,3'-bipyridine-6-carboxylate (3.2 g, 12.5 mmol) in 4 M HCl in dioxane (100 ml) was stirred at 110° C. overnight. The reaction mixture was evaporated completely under reduced pressure and triturated twice from diethyl ether. Yield 3.2 g. $^1$H-NMR (400 MHz; D$_2$O): δ 8.23-8.27 (m, 1H), 8.50 (d, 1H), 8.84 (d, 1H), 8.93 (d, 1H), 8.98 (d, 1H), 9.16 (s, 1H), 9.26 (s, 1H).

d) (S)—N-(1-(3-(3-Chloro-4-cyano-5-fluorophenyl)-1H-pyrazol-1-yl)propan-2-yl)-3,3'-bipyridine-6-carboxamide The title compound was prepared using the procedure described in Example 3(h) starting from 3,3'-bipyridine-6-carboxylic acid (0.861 mmol, 172 mg) and (S)-4-(1-(2-aminopropyl)-1H-pyrazol-3-yl)-2-chloro-6-fluorobenzonitrile (0.718 mmol, 200 mg) using DMF (2 ml) as the solvent. After the reaction had stopped, DCM was added and the reaction mixture was evaporated. The residue was purified by flash chromatography and trituration from methanol, respectively. 75 mg of the title compound was obtained. $^1$H-NMR (400 MHz, DMSO-d$_6$): δ 1.18 (d, 3H), 4.35-4.59 (m, 3H), 7.02 (d, 1H), 7.55-7.62 (m, 1H), 7.87-7.93 (m, 2H), 7.98 (s, 1H), 8.06-8.10 (m, 1H), 8.19-8.25 (m, 1H), 8.35 (dd, 1H), 8.68 (dd, 1H), 8.99-9.05 (m, 2H), 9.13 (d, 1H).

Example 21

(S)—N-(1-(3-(3-Chloro-4-cyano-5-fluorophenyl)-1H-pyrazol-1-yl)-propan-2-yl)-6-(3,3-dimethylureido)imidazo[1,2-a]pyridine-2-carboxamide a) Ethyl 6-(3,3-dimethylureido)imidazo[1,2-a]pyridine-2-carboxylate

Ethyl 6-aminoimidazo[1,2-a]pyridine-2-carboxylate (0.975 mmol, 0.2 g) was dissolved in THF (10 ml). Triethylamine (2.92 mmol, 0.296 g) was added and the reaction mixture was cooled to 0° C. Dimethylcarbamyl chloride (1.462 mmol, 0.135 ml) was added carefully and the mixture was allowed to warm to ambient temperature with stirring. More of dimethylcarbamyl chloride (1.462 mmol, 0.135 ml) was added and the stirring continued for another hour. The solvent was evaporated, DCM was added and the resulting mixture was washed with NaHCO₃ solution and water. The organic phase was dried, filtered and evaporated. The crude product was purified by flash chromatography. 0.066 g of the title compound was obtained. ¹H-NMR (400 MHz, DMSO-$d_6$): δ 1.31 (t, 3H), 2.95 (s, 6H), 4.29 (q, 2H), 7.39-7.44 (m, 1H), 7.50-7.54 (m, 1H), 8.41 (s, 1H), 8.54 (s, 1H), 8.89-8.93 (m, 1H).

b) 6-(3,3-Dimethylureido)imidazo[1,2-a]pyridine-2-carboxylic acid

Ethyl 6-(3,3-dimethylureido)imidazo[1,2-a]pyridine-2-carboxylate (0.239 mmol, 0.066 g) was dissolved in ethanol (5 ml). The solution was cooled to 0° C. and NaOH 2 M solution (0.478 mmol, 0.239 ml) was added. The resulting mixture was stirred at 0° C. Ethanol was evaporated and water was added. The pH of the water phase was adjusted to ~4 with HCl. The mixture was extracted with EtOAc and the organic phase was dried, filtered and evaporated. The residue was triturated with MeOH/DCM ⅑. The filtered precipitate was dried under vacuum. 0.067 g of the title compound was obtained. LC-MS: [M−1]=247.24.

c) (S)—N-(1-(3-(3-Chloro-4-cyano-5-fluorophenyl)-1H-pyrazol-1-yl)propan-2-yl)-6-(3,3-dimethylureido)imidazo[1,2-a]pyridine-2-carboxamide The title compound was prepared using the procedure described in Example 3(h) starting from 6-(3,3-dimethylureido)imidazo[1,2-a]pyridine-2-carboxylic acid (0.270 mmol, 0.067 g) and (S)-4-(1-(2-aminopropyl)-1H-pyrazol-3-yl)-2-chloro-6-fluorobenzonitrile (0.108 mmol, 0.04 g) using DMF (4 ml) as the solvent. HBTU (0.027 mmol, 10.24 mg) was used instead of HOBt. The product precipitated into the water phase and was separated by filtration. The organic phase also contained the product. The organic phase was dried, filtered and evaporated. The combined precipitates were purified by preparative HPLC. 0.0192 g of the title compound was obtained. ¹H-NMR (400 MHz, DMSO-$d_6$) δ ppm 1.13 (d, 3H), 2.95 (s, 6H), 4.30-4.54 (m, 3H), 7.01 (d, 1H), 7.40-7.45 (m, 1H), 7.47-7.52 (m, 1H), 7.87 (d, 1H), 7.93 (dd, 1H), 7.97 (s, 1H), 8.30 (s, 1H), 8.39 (bs, 1H), 8.49 (d, 1H), 8.87-8.91 (m, 1H).

Example 22

(S)—N-(1-(3-(3-Chloro-4-cyano-5-fluorophenyl)-1H-pyrazol-1-yl)-propan-2-yl)-6-(methylsulfonamido)imidazo[1,2-a]pyridine-2-carboxamide a) Ethyl 6-(N-(methylsulfonyl)methylsulfonamido)imidazo[1,2-a]pyridine-2-carboxylate Ethyl 6-aminoimidazo[1,2-a]pyridine-2-carboxylate (0.975 mmol, 0.2 g) was dissolved in THF (10 ml). Triethylamine (9.75 mmol, 0.986 g) was added and the mixture was cooled to 0° C. Methanesulfonyl chloride (9.75 mmol, 1.116 g) was slowly added and the mixture was allowed to cool to RT. The stirring continued at RT until the reaction was finished. The solvent was evaporated, DCM was added and washed with NaHCO₃ solution and water. The organic phase was dried, filtered and evaporated. The crude product was purified with flash chromatography. 0.149 g of the title compound was obtained. ¹H-NMR (400 MHz, DMSO-$d_6$): δ 1.33 (t, 3H), 3.61 (s, 6H), 4.34 (q, 2H), 7.50 (dd, 1H), 7.69-7.74 (m, 1H), 8.54-8.56 (m, 1H), 9.00-9.02 (m, 1H).

b) 6-(Methylsulfonamido)imidazo[1,2-a]pyridine-2-carboxylic acid

Ethyl 6-(N-(methylsulfonyl)methylsulfonamido)imidazo[1,2-a]pyridine-2-carboxylate (0.412 mmol, 0.149 g) was dissolved in ethanol (10 ml) and cooled to 0° C. with an ice bath. NaOH 2 M solution (0.825 mmol, 0.412 ml) was added and stirred at 0° C. for 3.5 h after which the temperature was allowed to warm to RT. The stirring continued overnight. The temperature was raised to 50° C. and stirred for 5 h. The mixture was again stirred at RT overnight. Ethanol was evaporated and water was added. The pH was adjusted to 4 with 1 M HCl after which the product started to precipitate. The precipitate was removed by filtration and dried under vacuum. 0.057 g of the title compound was obtained. ¹H-NMR (400 MHz, DMSO-$d_6$): δ 3.05 (s, 3H), 7.22-7.29 (m, 1H), 7.60-7.66 (m, 1H), 8.49-8.53 (m, 1H), 8.55 (s, 1H), 9.81 (s, 1H).

c) (S)—N-(1-(3-(3-Chloro-4-cyano-5-fluorophenyl)-1H-pyrazol-1-yl)propan-2-yl)-6-(methylsulfonamido)imidazo[1,2-a]pyridine-2-carboxamide The title compound was prepared using the procedure described in Example 3(h) starting from 6-(methylsulfonamido)imidazo[1,2-a]pyridine-2-carboxylic acid (0.215 mmol, 0.055 g) and (S)-4-(1-(2-aminopropyl)-1H-pyrazol-3-yl)-2-chloro-6-fluorobenzo-nitrile (0.179 mmol, 0.050 g) using DCM (10 ml) as the solvent. HBTU (0.018 mmol, 6.80 mg) was used instead of HOBt. The mixture was diluted with DCM and washed with Na₂CO₃ solution and water. The organic phase was evaporated. The water phase and Na₂CO₃ phase were washed with EtOAc. The evaporated organic phases were combined and purified by preparative HPLC. 0.0174 g of the title compound was obtained. ¹H-NMR (400 MHz, DMSO-$d_6$): δ 1.14 (d, 3H), 3.04 (s, 3H), 4.27-4.58 (m, 3H), 7.00 (d, 1H), 7.27 (dd, 1H), 7.57-7.62 (m, 1H), 7.87 (d, 1H), 7.91 (dd, 1H), 7.95-7.97 (m, 1H), 8.36 (d, 1H), 8.49-8.51 (m, 1H), 8.55 (d, 1H), 9.77 (s, 1H).

Example 23

N—((S)-1-(3-(3-Chloro-4-cyano-5-fluorophenyl)-1H-pyrazol-1-yl)propan-2-yl)-5-(1-hydroxy-2-methylpropyl)isoxazole-3-carboxamide a) Ethyl 5-(1-hydroxy-2-methylpropyl)isoxazole-3-carboxylate Ethyl chlorooximidoacetate (6.79 mmol, 1.029 g) and 4-methyl-1-pentyn-3-ol (20.38 mmol, 2 g) were dissolved in toluene (20 ml). Et₃N (6.79 mmol, 0.947 ml) dissolved in toluene was added dropwise. The mixture was stirred overnight at RT. The mixture was diluted with EtOAc and washed with water. The organic phase was dried, filtered and evaporated. The crude product was purified by flash chromatography. 0.828 g of the title compound was obtained. ¹H-NMR (400 MHz, MeOH-$d_4$): δ 0.92 (d, 3H), 0.97 (d, 3H), 1.39 (t, 3H), 2.03-2.16 (m, 1H), 4.41 (q, 2H), 4.58 (d, 1H), 6.65 (s, 1H).

b) 5-(1-Hydroxy-2-methylpropyl)isoxazole-3-carboxylic acid

Ethyl 5-(1-hydroxy-2-methylpropyl)isoxazole-3-carboxylate (2.345 mmol, 0.5 g) was dissolved in ethanol (5 ml)

and cooled to 0° C. NaOH 1 M solution (5 ml) was slowly added and the resulting mixture was allowed to warm to RT. The solution was heated to 60° C. for 3 h. Ethanol was removed by evaporation and the residue was diluted with tert-butyl methyl ether. The mixture was cooled to 0° C. and acidified with 2 N HCl solution. The mixture was allowed to warm to ambient temperature and stirred overnight. The mixture was extracted with DCM. Both organic and aqueous phases contained the product so both they were combined and evaporated. 0.691 g of the title compound was obtained. $^1$H-NMR (400 MHz, DMSO-$d_6$): δ 0.85 (d, 3H), 0.91 (d, 3H), 2.03 (qd, 1H), 4.54 (d, 1H), 6.66 (s, 1H).

c) N—((S)-1-(3-(3-Chloro-4-cyano-5-fluorophenyl)-1H-pyrazol-1-yl)propan-2-yl)-5-(1-hydroxy-2-methylpropyl)isoxazole-3-carboxamide The title compound was prepared using the procedure described in Example 3(h) starting from 5-(1-hydroxy-2-methylpropyl)isoxazole-3-carboxylic acid (2.160 mmol, 0.4 g) and (S)-4-(1-(2-aminopropyl)-1H-pyrazol-3-yl)-2-chloro-6-fluoro-benzonitrile (1.800 mmol, 0.502 g) using DMF (10 ml) as the solvent. The reaction mixture was diluted with water and EtOAc, the phases were separated and the organic phase was washed with 2 M $Na_2CO_3$, water and brine. The organic phase was dried, filtered and evaporated. The crude product was purified by flash chromatography and preparative HPLC, respectively. 0.0146 g of the title compound was obtained. $^1$H-NMR (400 MHz, MeOH-$d_4$): δ 0.89 (d, 3H), 0.92-0.98 (m, 3H), 1.26 (d, 3H), 2.01-2.13 (m, 1H), 4.28-4.45 (m, 2H), 4.51-4.64 (m, 2H), 6.53 (d, 1H), 6.79 (d, 1H), 7.68-7.77 (m, 2H), 7.91 (s, 1H).

Example 24

(S)—N-(1-(3-(3-Chloro-4-cyano-5-fluorophenyl)-1H-pyrazol-1-yl)propan-2-yl)-5-(1,5-dimethyl-1H-pyrazol-3-yl)-1,2,4-oxadiazole-3-carboxamide a) Ethyl 5-(1,5-dimethyl-1H-pyrazol-3-yl)-1,2,4-oxadiazole-3-carboxylate

Ethyl aminohydroxyiminoacetate (3.78 mmol, 0.5 g), 1,5-dimethyl-1H-pyrazole-3-carboxylic acid (95%, 3.78 mmol, 0.530 g) and 1,3-diisopropylcarbodiimide (4.16 mmol, 0.525 g) were suspended in DCM (70 ml) under nitrogen atmosphere. The mixture was stirred at RT for a day. The solvent was evaporated and pyridine was added to the residue. The resulting mixture was refluxed for 6 h and stirred at RT overnight. Pyridine was evaporated and the residue diluted with DCM and water. The phases were separated and the water phase was extracted four times with DCM. The combined organics were washed with aqueous HCl solution, saturated $NaHCO_3$, water and brine. The organic phase was dried, filtered and evaporated. The crude product was purified by flash chromatography. 0.285 g of the title compound was obtained. $^1$H-NMR (400 MHz, MeOH-$d_4$): δ 1.43 (t, 3H), 2.30 (s, 3H), 4.23 (s, 3H), 4.49 (q, 2H), 6.96 (s, 1H).

b) 5-(1,5-Dimethyl-1H-pyrazol-3-yl)-1,2,4-oxadiazole-3-carboxylic acid

Ethyl 5-(1,5-dimethyl-1H-pyrazol-3-yl)-1,2,4-oxadiazole-3-carboxylate (1.206 mmol, 0.285 g) was dissolved in ethanol (7 ml) and cooled to 0° C. with an ice bath. NaOH 1 M solution (3 ml) was added, the ice bath was removed and the mixture was heated to 60° C. for 1.5 h. Ethanol was evaporated and the residue was diluted with MTBE. The mixture was again cooled with an ice bath and acidified with 2 M HCl. The mixture was warmed to RT and stirred overnight. Water, MTBE and DCM were added, but the precipitate did not dissolve. The organic phase and the water phase were combined and evaporated. 0.336 g of the title compound was obtained. $^1$H-NMR (400 MHz, DMSO-$d_6$): δ 2.27 (s, 3H), 4.16 (s, 3H), 7.01 (s, 1H).

c) (S)—N-(1-(3-(3-Chloro-4-cyano-5-fluorophenyl)-1H-pyrazol-1-yl)propan-2-yl)-5-(1,5-dimethyl-1H-pyrazol-3-yl)-1,2,4-oxadiazole-3-carboxamide The title compound was prepared using the procedure described in Example 3(h) starting from 5-(1,5-dimethyl-1H-pyrazol-3-yl)-1,2,4-oxadiazole-3-carboxylic acid (1.614 mmol, 0.336 g) and (S)-4-(1-(2-aminopropyl)-1H-pyrazol-3-yl)-2-chloro-6-fluoro-benzonitrile (1.345 mmol, 0.375 g) using DMF (10 ml) as the solvent. The reaction mixture was diluted with water and EtOAc, the phases were separated and the organic phase was washed with 2 M $Na_2CO_3$, water and brine. The organic phase was dried, filtered and evaporated. The crude product was purified by flash chromatography and preparative HPLC, respectively. 0.003 g of the title compound was obtained. $^1$H-NMR (400 MHz, $CDCl_3$): δ 1.29 (d, 3H), 2.34 (s, 3H), 4.24 (s, 3H), 4.30 (dd, 1H), 4.49 (dd, 1H), 4.61-4.72 (m, 1H), 6.65 (d, 1H), 6.88 (s, 1H), 7.53 (d, 1H), 7.61 (dd, 1H), 7.78-7.82 (m, 1H), 8.01 (d, 1H).

Example 25

(S)—N-(1-(3-(3-Chloro-4-cyano-5-fluorophenyl)-1H-pyrazol-1-yl)propan-2-yl)-5-(isoxazol-3-yl)-1,2,4-oxadiazole-3-carboxamide a) Ethyl 5-(isoxazol-3-yl)-1,2,4-oxadiazole-3-carboxylate

Ethyl aminohydroxyiminoacetate (3.78 mmol, 0.5 g), 3-isoxazolecarboxylic acid (3.78 mmol, 0.428 g) and 1,3-diisopropylcarbodiimide (4.16 mmol, 0.525 g) were dissolved in DCM (70 ml) under nitrogen atmosphere. The mixture was stirred at RT for a day. The solvent was evaporated to dryness and the residue was dissolved in pyridine and refluxed for 6 h and overnight at RT. Pyridine was evaporated and the residue was diluted with DCM and water. The aqueous phase was extracted four times with DCM. The combined organics were washed with aqueous HCl solution, saturated $NaHCO_3$, water and brine. The organic phase was dried, filtered and evaporated. The crude product was purified by flash chromatography. 0.396 g of the title compound was obtained. Rotamers were obtained in $^1$H-NMR and analysis was repeated at elevated temperature. $^1$H-NMR (400 MHz, DMSO-$d_6$, +60° C.): δ 1.38 (t, 3H), 4.49 (q, 2H), 7.21 (d, 1H), 9.05 (d, 1H).

b) 5-(Isoxazol-3-yl)-1,2,4-oxadiazole-3-carboxylic acid

Ethyl 5-(isoxazol-3-yl)-1,2,4-oxadiazole-3-carboxylate (1.893 mmol, 0.396 g) was dissolved in ethanol (5 ml) and cooled to 0° C. with an ice bath. NaOH 1 M solution (4 ml) was slowly added and the mixture was heated to 60° C. for 3 h. Ethanol was evaporated and the residue was diluted with MTBE. The mixture was cooled to 0° C. and acidified by adding 2 M HCl. The mixture was stirred at RT overnight. Water was added and the phases were separated and the water phase was evaporated. 0.533 g of the title compound was obtained. $^1$H-NMR (400 MHz, D$_2$O): δ 6.68 (d, 1H), 8.65 (d, 1H).

c) (S)—N-(1-(3-(3-Chloro-4-cyano-5-fluorophenyl)-1H-pyrazol-1-yl)propan-2-yl)-5-(isoxazol-3-yl)-1,2,4-oxadiazole-3-carboxamide The title compound was prepared using the procedure described in Example 3(h) starting from 5-(isoxazol-3-yl)-1,2,4-oxadiazole-3-carboxylic acid (1.933 mmol, 0.35 g) and (S)-4-(1-(2-amino-propyl)-1H-pyrazol-3-yl)-2-chloro-6-fluorobenzo-nitrile (1.610 mmol, 0.449 g) using DMF (10 ml) as the solvent. The reaction mixture was diluted with water and EtOAc, the phases were separated and the organic phase was washed with 2M Na$_2$CO$_3$, water and brine. The organic phase was dried, filtered and evaporated. The crude product was purified by flash chromatography and preparative HPLC, respectively. 0.0065 g of the title compound was obtained. $^1$H-NMR (400 MHz, CDCl$_3$): δ 1.26 (d, 3H), 4.28 (dd, 1H), 4.46 (dd, 1H), 4.56-4.66 (m, 1H), 6.63 (d, 1H), 6.82 (d, 1H), 7.51 (d, 1H), 7.64 (dd, 1H), 7.84-7.86 (m, 1H), 7.88 (d, 1H), 8.51 (d, 1H).

Example 26

(S)—N-(1-(3-(3-Chloro-4-cyano-5-fluorophenyl)-1H-pyrazol-1-yl)-propan-2-yl)-3-(1H-imidazol-4-yl)-1H-pyrazole-5-carboxamide a) Lithium (Z)-4-(1-benzyl-1H-imidazol-4-yl)-1-ethoxy-1,4-dioxobut-2-en-2-olate 5-Acetyl-1-benzylimidazole (24.97 mmol, 5 g) was dissolved in dry diethyl ether (100 ml) under nitrogen atmosphere. The mixture was cooled to −75° C. and lithium bis(trimethylsilyl)amide (27.5 mmol, 27.5 ml) was added dropwise. The resulting mixture was stirred at −75° C. for an hour. Diethyl oxalate (32.5 mmol, 4.74 g) was added and the mixture was allowed to warm to ambient temperature after which the mixture was stirred for a day at RT. The formed precipitate was removed by filtration and the precipitate was washed with diethyl ether. The precipitate was dried under vacuum. 7.38 g of the title compound was obtained. $^1$H-NMR (400 MHz, DMSO-d$_6$): δ 1.22 (t, 3H), 4.11 (q, 2H), 5.61 (s, 2H), 6.17 (s, 1H), 7.15-7.31 (m, 5H), 7.48 (d, 1H), 7.88 (d, 1H).

b) Ethyl 3-(1-benzyl-1H-imidazol-4-yl)-1H-pyrazole-5-carboxylate

Lithium (Z)-4-(1-benzyl-1H-imidazol-4-yl)-1-ethoxy-1,4-dioxobut-2-en-2-olate (9.80 mmol, 3.0 g) was suspended in dry ethanol (20 ml). Hydrazine dihydro-chloride (12.74 mmol, 1.337 g) was added and the resulting mixture was refluxed for 2 h. The mixture was cooled to ambient temperature and evaporated. The sticky oil was purified by trituration from ethanol. The precipitate was separated by filtration and flushed with cold ethanol. 2.614 g of the title compound was obtained. $^1$H-NMR (400 MHz, DMSO-d$_6$): δ 1.31 (t, 3H), 4.33 (q, 2H), 5.81 (bs, 2H), 7.11-7.39 (m, 6H), 8.16 (bs, 1H), 9.31 (bs, 1H), 14.50 (bs, 1H).

c) Ethyl 3-(1H-imidazol-4-yl)-1H-pyrazole-5-carboxylate

Ethyl 3-(1-benzyl-1H-imidazol-4-yl)-1H-pyrazole-5-carboxylate (8.77 mmol, 2.6 g) was dissolved in a mixture of acetic acid (10 ml) and ethanol (190 ml). The mixture was run through H-Cube (10% Pd/C CatCart (8.77 mmol) flow 1.5 ml/min, +80° C., Full hydrogen mode). The collected fractions were combined and evaporated. The acquired solid was stirred in toluene and evaporated. This was repeated once more. 1.837 g of the title compound was obtained. $^1$H-NMR (400 MHz, DMSO-d$_6$): δ 1.33 (t, 3H), 4.35 (q, 2H), 7.38 (s, 1H), 8.07 (d, 1H), 9.14 (bs, 1H), 14.44 (bs, 1H). LC-MS: [M−1]=205.0.

d) Ethyl 3-(1-trityl-1H-imidazol-4-yl)-1H-pyrazole-5-carboxylate

Ethyl 3-(1H-imidazol-4-yl)-1H-pyrazole-5-carboxylate (6.79 mmol, 1.4 g) was suspended in DCM (20 ml) under nitrogen atmosphere. Triphenylmethyl chloride (8.15 mmol, 2.271 g) was added and stirred for 10 min at RT. Triethylamine (8.15 mmol, 1.136 ml) was added and the resulting mixture was stirred for 20 h at RT after which DCM (10 ml) and triphenylmethyl chloride (1 g) was added. The stirring was continued for another 4.5 days. More triphenylmethyl chloride (1.14 g) and triethylamine (0.6 ml) was added and the mixture was stirred for another day. The mixture was diluted with DCM and washed with NaHCO$_3$. The organic phase was dried, filtered and evaporated. The residue was purified by trituration from ACN. 1.837 g of the title compound was obtained. $^1$H-NMR (400 MHz, DMSO-d$_6$): δ 1.28 (t, 3H), 4.25 (q, 2H), 6.89 (s, 1H), 7.09-7.18 (m, 6H), 7.18-7.33 (m, 6H), 7.36-7.47 (m, 3H), 7.50 (s, 1H), 7.55 (s, 1H), 13.63 (bs, 1H).

e) 3-(1-Trityl-1H-imidazol-4-yl)-1H-pyrazole-5-carboxylic acid

Ethyl 3-(1-trityl-1H-imidazol-4-yl)-1H-pyrazole-5-carboxylate (4.01 mmol, 1.8 g) was dissolved in ethanol (20 ml) and cooled to 0° C. NaOH 2 M solution (8.03 mmol, 4.01 ml) was added and the mixture was stirred at RT for an hour. The mixture was heated to 60° C. and stirred for 10 h. Ethanol was evaporated and the residue was diluted with water. The pH was adjusted to 4 with 1 M HCl solution which precipitated the product. The precipitate was removed by filtration and washed with water. The solid was dried under vacuum. 1.5 g of the title compound was obtained. $^1$H-NMR (400 MHz, DMSO-d$_6$): δ 6.75 (bs, 1H), 7.08-7.17 (m, 6H), 7.18-7.34 (m, 5H), 7.36-7.49 (m, 8H). LC-MS: [M−1]=419.1.

f) (S)—N-(1-(3-(3-Chloro-4-cyano-5-fluorophenyl)-1H-pyrazol-1-yl)propan-2-yl)-3-(1-trityl-1H-imidazol-4-yl)-1H-pyrazole-5-carboxamide The title compound was prepared using the procedure described in Example 3(h) starting from 3-(1-trityl-1H-imidazol-4-yl)-1H-pyrazole-5-carboxylic acid (0.875 mmol, 0.368 g) and (S)-4-(1-(2-aminopropyl)-1H-pyrazol-3-yl)-2-chloro-6-fluorobenzonitrile (0.673 mmol, 0.250 g) using HBTU (0.067 mmol, 0.026 g) instead of HOBt. DCM (4 ml) was used as the solvent. The reaction mixture was diluted with DCM and washed with 1 M Na$_2$CO$_3$ and water. The separated organic phase was dried, filtered and evaporated to give 0.511 g of crude product. Another crude batch (931 mg) was combined here and purified first by trituration in ACN and then by flash chromatography to give 0.095 g of the product. $^1$H-NMR (400 MHz, DMSO-d$_6$): δ 1.18 (d, 3H), 4.13-4.53 (m, 3H), 6.64 (s, 1H), 6.98 (d, 1H), 7.09-7.19 (m, 4H), 7.35-7.51 (m, 9H), 7.52-7.57 (m, 1H), 7.70-7.76 (m, 1H), 7.79-7.86 (m, 2H), 7.92 (s, 1H), 7.95 (s, 1H), 8.06-8.10 (m, 1H), 8.14-8.18 (m, 1H), 13.35 (bs, 1H).

g) (S)—N-(1-(3-(3-Chloro-4-cyano-5-fluorophenyl)-1H-pyrazol-1-yl)propan-2-yl)-3-(1H-imidazol-4-yl)-1H-pyrazole-5-carboxamide Into (S)—N-(1-(3-(3-chloro-4-cyano-5-fluorophenyl)-1H-pyrazol-1-yl)propan-2-yl)-3-(1-trityl-1H-imidazol-4-yl)-1H-pyrazole-5-carboxamide (0.139 mmol, 0.095 g) was added 4 ml of a solution containing formic acid (41.8 mmol, 1.926 g), THF (20 ml) and water (1 ml). The resulting mixture was stirred first at RT after which the temperature was raised to 50° C. for 2 h. The solvent was evaporated, ACN was added and evaporated again. This was repeated once more. The crude product was purified by preparative HPLC. 0.0169 g of the title compound was obtained. $^1$H-NMR (400 MHz, CDCl$_3$): δ 1.27 (d, 3H), 4.14 (dd, 1H), 4.45 (dd, 1H), 4-57-4.64 (m, 1H), 6.29 (bs), 6.63 (d, 1H), 6.90 (s, 1H), 7.32 (d, 1H), 7.51 (d, 1H), 7.52 (s, 1H), 7.63 (dd, 1H), 7.73 (d, 1H), 7.84-7.86 (m, 1H) LC-MS: [M+1]=439.0.

Example 27

(S)—N-(1-(3-(3-Chloro-4-cyano-5-fluorophenyl)-1H-pyrazol-1-yl)propan-2-yl)-2-(chloropropan-2-yl)oxazole-4-carboxamide a) (S)—N-(1-(3-(3-Chloro-4-cyano-5-fluorophenyl)-1H-pyrazol-1-yl)propan-2-yl)-2-(2-hydroxypropan-2-yl)oxazole-4-carboxamide The title compound was prepared using the procedure described in Example 3(h) starting from 2-(2-hydroxypropan-2-yl)oxazole-4-carboxylic acid (2.153 mmol, 0.368 g) and (S)-4-(1-(2-aminopropyl)-1H-pyrazol-3-yl)-2-chloro-6-fluorobenzo-nitrile (2.153 mmol, 0.6 g) and using HBTU (0.215 mmol, 0.082 g) instead of HOBt. DCM (15 ml) was used as the solvent. During the reaction a new batch of starting materials was added to the reaction mixture. The batch contained half the amount of starting materials used in the beginning of the reaction with the exception that (S)-4-(1-(2-aminopropyl)-1H-pyrazol-3-yl)-2-chloro-6-fluorobenzonitrile was not added at all. The resulting mixture was stirred for 2 days. The mixture was diluted with DCM and washed with Na$_2$CO$_3$ solution and water. The organic phase was dried, filtered and evaporated. The crude product was purified by flash chromatography. 0.669 g of the title compound was obtained. $^1$H-NMR (400 MHz, DMSO-d$_6$): δ 1.13 (d, 3H), 1.52 (s, 6H), 4.27-4.54 (m, 3H), 5.63 (s, 1H), 7.02 (d, 1H), 7.83-7.89 (m, 2H), 7.98 (s, 1H), 8.10 (d, 1H), 8.48 (s, 1H).

b) (S)—N-(1-(3-(3-Chloro-4-cyano-5-fluorophenyl)-1H-pyrazol-1-yl)propan-2-yl)-2-(chloropropan-2-yl)oxazole-4-carboxamide (S)—N-(1-(3-(3-Chloro-4-cyano-5-fluorophenyl)-1H-pyrazol-1-yl)propan-2-yl)-2-(2-hydroxypropan-2-yl)oxazole-4-carboxamide (0.116 mmol, 0.05 g) was dissolved in DMF (5 ml) and triethylamine (0.255 mmol, 0.026 g) was added. Diethyl chlorophosphate (0.232 mmol, 0.040 g) was carefully added with a syringe. The resulting mixture was stirred at RT overnight. A mixture of ice and water was added and the mixture was neutralized with 1 M NaOH. The mixture was extracted twice with DCM. The combined organics were washed with water, dried, filtered and evaporated. The crude product was purified by preparative HPLC. 0.0047 g of the title compound was obtained. $^1$H-NMR (400 MHz, CDCl$_3$): δ 1.26 (d, 3H), 2.04 (d, 6H), 4.29-4.36 (m, 1H), 4.38-4.46 (m, 1H), 4.54-4.66 (m, 1H), 6.64 (d, 1H), 7.39 (d, 1H), 7.51 (d, 1H), 7.61 (dd, 1H), 7.72-7.75 (m, 1H), 8.17 (s, 1H).

Example 28

(S)—N-(1-(3-(3-Chloro-4-cyano-5-fluorophenyl)-1H-pyrazol-1-yl)-propan-2-yl)-2-(2-propen-2-yl)oxazole-4-carboxamide The title product was a by-product from the reaction in which (S)—N-(1-(3-(3-chloro-4-cyano-5-fluorophenyl)-1H-pyrazol-1-yl)propan-2-yl)-2-(chloro-propan-2-yl)oxazole-4-carboxamide was synthesized. This compound was separated from the main product during preparative HPLC purification. 0.008 g of the title compound was obtained. $^1$H-NMR (400 MHz, CDCl$_3$): δ 1.27 (d, 3H), 2.13-2.18 (m, 3H), 4.31 dd, 1H), 4.42 (dd, 1H), 4.54-4.65 (m, 1H), 5.45-5.50 (m, 1H), 5.98-6.02 (m, 1H), 6.62 (d, 1H), 7.45 (d, 1H), 7.51 (d, 1H), 7.61 (dd, 1H), 7.71-7.74 (m, 1H), 8.11 (s, 1H).

Example 29

(S)—N-(1-(3-(3-Chloro-4-cyano-5-fluorophenyl)-1H-pyrazol-1-yl)propan-2-yl)-N-5-cyclopropylisoxazole-3,5-dicarboxamide a) 3-(Ethoxycarbonyl)isoxazole-5-carboxylic acid

Ethyl chlorooximidoacetate (3.30 mmol, 0.5 g) and propiolic acid (33.0 mmol, 2.311 g) were dissolved in diethyl ether (10 ml) with stirring. Triethylamine (3.30 mmol, 0.334 g) dissolved in diethyl ether (5 ml) was added dropwise to the previous mixture. The reaction mixture was stirred for three days at RT during which more triethylamine (2×0.668 g dissolved in 5 ml diethyl ether) was added dropwise. The pH of the reaction mixture was adjusted to 2. The organic phase was washed twice with water. The organic phase was dried, filtered and evaporated. The residue was dried under vacuum. 369 mg of the title compound was obtained. $^1$H-NMR (400 MHz, CDCl$_3$): δ 1.44 (t, 3H), 4.49 (q, 2H), 7.41 (s, 1H), 10.59 (bs, 1H).

b) Ethyl 5-(cyclopropylcarbamoyl)isoxazole-3-carboxylate

The title compound was prepared starting from 3-(ethoxycarbonyl)isoxazole-5-carboxylic acid (3.78 mmol, 0.7 g) and cyclopropyl-amine (2.91 mmol, 0.166 g) using DCM (10 ml) as the solvent. The mixture was diluted with DCM and washed with 1 M Na$_2$CO$_3$ and water. The organic phase was dried, filtered and evaporated. The crude product was purified by flash chromatography. 0.284 g of the title compound was obtained. $^1$H-NMR (400 MHz, DMSO-d$_6$) δ 0.58-0.64 (m, 2H), 0.70-0.77 (m, 2H), 1.33 (t, 3H), 2.80-2.90 (m, 1H), 4.38 (q, 2H), 7.39 (s, 1H), 9.04 (bs, 1H).

c) 5-(Cyclopropylcarbamoyl)isoxazole-3-carboxylic acid

Ethyl 5-(cyclopropylcarbamoyl)isoxazole-3-carboxylate (1.267 mmol, 0.284 g) was dissolved in ethanol (10 ml). The mixture was cooled in an ice bath and NaOH 2 M solution (2.53 mmol, 1.267 ml) was added. The resulting mixture was stirred in cold until the reaction was complete. Ethanol was evaporated and water was added. The pH of the mixture was adjusted to 4 with HCl. The precipitate was removed by filtration. The filtrate was evaporated and purified by trituration from ⅑ MeOH/DCM. 0.058 g of the title compound was obtained. $^1$H-NMR (400 MHz, DMSO-d$_6$): δ 0.57-0.66 (m, 2H), 0.67-0.75 (m, 2H), 2.77-2.88 (m, 1H), 6.97 (s, 1H), 8.85 (m, 1H).

d) (S)—N-3-(1-(3-(3-Chloro-4-cyano-5-fluorophenyl)-1H-pyrazol-1-yl)propan-2-yl)-N-5-cyclopropyl-isoxazole-3,5-dicarboxamide The title compound was prepared using the procedure described in Example 3(h) starting from 5-(cyclopropyl-carbamoyl)isoxazole-3-carboxylic acid (0.377 mmol, 0.074 g) and (S)-4-(1-(2-amino-propyl)-1H-pyrazol-3-yl)-2-chloro-6-fluoro-benzonitrile (0.377 mmol, 0.14 g) using DMF (4 ml) as the solvent. HBTU (0.038 mmol, 0.014 g) was used instead of HOBt. The crude product was purified by preparative HPLC. 0.0011 g of the title compound was obtained. $^1$H-NMR (400 MHz, CDCl$_3$): δ 0.69-0.75 (m, 2H), 0.91-0.98 (m, 2H), 1.26 (d, 3H), 2.87-2.96 (m, 1H), 4.26 (dd, 1H), 4.46 (dd, 1H), 4.55-4.65 (m, 1H), 6.58-6.63 (m, 1H), 6.64 (d, 1H), 7.30 (s, 1H), 7.51 (d, 1H), 7.63-7.69 (m, 1H), 7.82 (s, 1H), 7.93 (d, 1H).

Example 30

(S)-2-Bromo-N-(1-(3-(3-chloro-4-cyano-5-fluorophenyl)-1H-pyrazol-1-yl)-propan-2-yl)-1H-imidazole-4-carboxamide The title compound was prepared using the procedure described in Example 3(h) starting from 2-bromo-1H-imidazole-4-carboxylic acid (4.31 mmol, 0.822 g) and (S)-4-(1-(2-aminopropyl)-1H-pyrazol-3-yl)-2-chloro-6-fluorobenzonitrile (3.59 mmol, 1 g) using DMF (10 ml) as the solvent. DCM and water was added to the mixture, the layers were separated and the water phase was extracted with DCM. The combined organics were washed three times with water. The DCM phase was dried, filtered and evaporated. The crude product was purified by flash chromatography and preparative HPLC, respectively. 30.5 mg of the title compound was obtained. $^1$H-NMR (400 MHz, DMSO-d$_6$): δ 1.10 (d, 3H), 4.24-4.49 (m, 3H), 7.00 (d, 1H), 7.62 (s, 1H), 7.83 (d, 1H), 7.87 (d, 1H), 7.96 (s, 1H), 8.11 (d, 1H), 13.23 (bs, 1H).

Example 31

(S)—N-(1-(3-(3-Chloro-4-cyano-5-fluorophenyl)-1H-pyrazol-1-yl)propan-2-yl)-1-(2-methylprop-1-enyl)-1H-pyrazole-3-carboxamide a) Methyl 1-(2-methylprop-1-enyl)-1H-pyrazole-3-carboxylate The title compound was prepared using the procedure described in Example 17(a) starting from methyl 1H-pyrazole-3-carboxylate (8 g, 63.4 mmol) and 1-bromo-2-methyl propene (12.7 g, 95.2 mmol). The product was purified with flash chromatography. Yield 2.4 g. $^1$H-NMR (400 MHz; CDCl$_3$): δ 1.81 (d, 3H), 1.87 (d, 3H), 3.93 (s, 3H), 6.70 (d, 1H), 6.87 (d, 1H), 7.47 (d, 1H).

b) 1-(2-Methylprop-1-enyl)-1H-pyrazole-3-carboxylic acid

The title compound was prepared using the procedure described in Example 32(d) starting from methyl 1-(2-methylprop-1-enyl)-1H-pyrazole-3-carboxylate (2.4 g, 13.3 mmol). Yield 1.6 g. $^1$H-NMR (400 MHz; DMSO-d6): δ 1.84 (s, 6H), 6.77 (d, 1H), 6.82 (s, 1H), 7.87 (d, 1H), 12.7 (bs, 1H).

c) (S)—N-(1-(3-(3-Chloro-4-cyano-5-fluorophenyl)-1H-pyrazol-1-yl)propan-2-yl)-1-(2-methylprop-1-enyl)-1H-pyrazole-3-carboxamide The title compound was prepared using the procedure described in Example 3(h) starting from 1-(2-methyl-prop-1-en-1-yl)-1H-pyrazole-3-carboxylic acid (1.076 mmol, 179 mg) and (S)-4-(1-(2-aminopropyl)-1H-pyrazol-3-yl)-2-chloro-6-fluoro-benzonitrile (0.897 mmol, 250 mg) using DCM (5 ml) as the solvent. The mixture was diluted with DCM, washed with 1M Na$_2$CO$_3$ and water. The organic phase was dried, filtered and evaporated. The product was purified by flash chromatography. 298 mg of the title compound was obtained. $^1$H-NMR (400 MHz, DMSO-d$_6$): δ 1.12 (d, 3H), 1.80 (d, 3H), 1.84 (d, 3H), 4.27-4.50 (m, 3H), 6.66 (d, 1H), 6.77-6.80 (m, 1H), 7.01 (d, 1H), 7.83 (d, 1H), 7.85-7.89 (m, 2H), 7.95-7.98 (m, 1H), 8.15 (d, 1H).

Example 32

(S)—N-(1-(3-(3-Chloro-4-cyano-5-fluorophenyl)-1H-pyrazol-1-yl)propan-2-yl)-1-cyclopropyl-1H-pyrazole-3-carboxamide a) 1H-Pyrazole-3-carboxylic acid 3-Methylpyrazole (20 g, 243.5 mmol) was dissolved in water (500 ml). Into the solution, aqueous KMnO$_4$ (96.2 g, 608.9 mmol in 900 ml of water) was added and the resulting mixture was refluxed for 12 h. The reaction mixture was filtered through a celite bed and concentrated. The white residue was dissolved in water and made to pH 2 using concentrated HCl. The precipitated solids were filtered under vacuum. Yield 15 g. LC-MS: [M+1]=112.98.

b) Methyl 1H-pyrazole-3-carboxylate

1H-Pyrazole-3-carboxylic acid (15 g, 133.8 mmol) was dissolved in MeOH (250 ml). Concentrated H$_2$SO$_4$ (30 ml) was added to the solution. The resulting mixture was refluxed for 12 h and concentrated. The residue obtained was quenched by saturated aqueous solution of NaHCO$_3$ and extracted with EtOAc. The organic layer was concentrated. Yield 12.05 g. $^1$H-NMR (400 MHz; CDCl$_3$): δ 3.98 (s, 3H), 6.86 (d, 1H), 7.85 (d, 1H), 11.9 (bs, 1H).

c) Methyl 1-cyclopropyl-1H-pyrazole-3-carboxylate

Methyl 1H-pyrazole-3-carboxylate (4 g, 31.7 mmol) was dissolved in dichloroethane (160 ml). Na$_2$CO$_3$ (6.72 g, 63.4 mmol) and cyclopropylboronic acid (5.44 g, 63.4 mmol) were added to the solution. The resulting mixture was heated to 70° C. and a hot solution of bipyridine (4.92 g, 31.6 mmol) and Cu(OAc)$_2$ (5.72 g, 31.6 mmol) in dichloroethane (40 ml) was added. The mixture was stirred at 70° C. under an oxygen atmosphere overnight. Saturated aqueous solution of NaHCO$_3$ was added to the reaction mixture and extracted with EtOAc. The organic layer was evaporated and the residue was purified by flash chromatography. Yield 2.5 g. $^1$H-NMR (400 MHz; DMSO-d6): δ 1.04-1.09 (m, 2H), 1.17-1.23 (m, 2H), 3.64-3.69 (m, 1H), 3.91 (s, 3H), 6.78 (d, 1H), 7.46 (d, 1H).

d) 1-Cyclopropyl-1H-pyrazole-3-carboxylic acid

Methyl 1-cyclopropyl-1H-pyrazole-3-carboxylate (2.5 g, 15 mmol) was dissolved in THF (40 ml) and $H_2O$ (10 ml). $LiOH.H_2O$ (1.50 g, 22.5 mmol) was added and the mixture was stirred at RT overnight. The reaction mixture was concentrated and acidified to pH 2 using 1 N HCl. The mixture was extracted with EtOAc and the organic layer was concentrated. Yield 1.6 g. $^1$H-NMR (400 MHz; DMSO-d6): δ 0.96-1.02 (m, 2H), 1.04-1.09 (m, 2H), 3.79-3.84 (m, 1H), 6.66 (d, 1H), 7.88 (d, 1H), 12.6 (bs, 1H).

e) (S)—N-(1-(3-(3-Chloro-4-cyano-5-fluorophenyl)-1H-pyrazol-1-yl)propan-2-yl)-1-cyclopropyl-1H-pyrazole-3-carboxamide 1-Cyclopropyl-1H-pyrazole-3-carboxylic acid (0.30 g, 1.29 mmol) was dissolved in DCM (20 ml). EDCI (0.692 g, 3.61 mmol), HOBt (0.487 g, 3.61 mmol) and DIPEA (0.932 g, 7.22 mmol) were added at 0° C. to the solution. The resulting mixture was stirred at 0° C. for 15 min. (S)-4-(1-(2-Aminopropyl)-1H-pyrazol-3-yl)-2-chloro-6-fluorobenzonitrile (0.502 g, 1.8 mmol) dissolved in DCM (2 ml) was added and the mixture was stirred overnight. The reaction mixture was quenched by the addition of water and extracted with DCM. The organic layer was evaporated and the residue was purified by flash chromatography. Yield: 400 mg. $^1$H-NMR (400 MHz; DMSO-d6): δ 0.97-1.17 (m, 7H), 3.74-3.80 (m, 1H), 4.26-4.41 (m, 3H), 6.53 (d, 1H), 7.01 (d, 1H), 7.82-7.87 (m, 3H), 7.96 (s, 1H), 8.14 (d, 1H).

Example 33

N—((S)-1-(3-(3-Chloro-4-cyano-5-fluorophenyl)-1H-pyrazol-1-yl)propan-2-yl)-2-(1-hydroxyethyl)-1H-imidazole-4-carboxamide a) Methyl 2-(1-ethoxyvinyl)-1-((2-(trimethylsilyl)ethoxy)methyl)-1H-imidazole-4-carboxylate Methyl-2-bromo-1-((2-(trimethylsilyl)ethoxy)methyl)-1H-imidazole-4-carboxylate (10 g, 29.9 mmol) was dissolved in dioxane (200 ml). Tributyl(1-ethoxy-vinyl)stannane (16.2 g, 44.8 mmol) was added to the solution. The resulting mixture was degassed and purged with argon for 20 min. Then $Pd(PPh_3)_4$ (3.45 g, 2.99 mmol) was added and the mixture was refluxed overnight. The reaction mixture was cooled to RT and diluted with cold water. The mixture was extracted with EtOAc and washed with aqueous KF solution. The organic layer was concentrated to give the desired product. Yield 12.1 g. LC-MS: [M+1]=327.78.

b) Methyl 2-acetyl-1-((2-(trimethylsilyl)ethoxy)methyl)-1H-imidazole-4-carboxylate Into a flask containing a solution of methyl-2-(1-ethoxyvinyl)-1-((2-(tri-methylsilyl)-ethoxy)methyl)-1H-imidazole-4-carboxylate (3.5 g, 10.7 mmol) in THF (25 ml), 2 N HCl (25 ml) was added at RT and stirred for 3 h. The reaction mixture was concentrated and extracted with DCM. The organic layer was evaporated and the residue was purified by flash chromatography. Yield 2.6 g. $^1$H-NMR (400 MHz; CDCl$_3$): δ −0.016 (s, 9H), 0.94 (t, 2H), 2.73 (s, 3H), 3.58 (t, 2H), 3.94 (s, 3H), 5.76 (s, 2H), 7.93 (s, 1H).

c) 2-Acetyl-1-((2-(trimethylsilyl)ethoxy)methyl)-1H-imidazole-4-carboxylic acid The title compound was prepared using the procedure described in Example 32(d) starting from methyl-2-acetyl-1-((2-(trimethylsilyl)ethoxy)methyl)-1H-imidazole-4-carboxylate (2.5 g, 8.3 mmol). Yield 2 g. $^1$H-NMR (400 MHz; DMSO-d$_6$): δ −0.06 (s, 9H), 0.83 (t, 2H), 2.57 (s, 3H), 3.53 (t, 2H), 5.68 (s, 2H), 8.23 (s, 1H), 12.76 (s, 1H).

d) (S)-2-Acetyl-N-(1-(3-(3-chloro-4-cyano-5-fluorophenyl)-1H-pyrazol-1-yl)-propan-2-yl)-1-((2-(trimethylsilyl)ethoxy)methyl)-1H-imidazole-4-carboxamide The title compound was prepared using the procedure described in Example 32(e) starting from 2-acetyl-1-((2-(tri-methylsilyl)ethoxy)methyl)-1H-imidazole-4-carboxylic acid (400 mg, 1.4 mmol) and (S)-4-(1-(2-aminopropyl)-1H-pyrazol-3-yl)-2-chloro-6-fluoro-benzonitrile (389 mg, 1.4 mmol). The product was purified with flash chromatography. Yield 260 mg. $^1$H-NMR (400 MHz; DMSO-d$_6$): δ −0.09 (s, 9H), 0.81 (t, 2H), 1.15 (d, 3H), 2.61 (s, 3H), 3.48 (t, 2H), 4.33-4.48 (m, 3H), 5.66 (s, 2H), 7.02 (d, 1H), 7.84-7.87 (m, 2H), 7.95 (s, 1H), 8.06 (s, 1H), 8.15 (d, 1H).

e) N—((S)-1-(3-(3-Chloro-4-cyano-5-fluorophenyl)-1H-pyrazol-1-yl)propan-2-yl)-2-(1-hydroxyethyl)-1-((2-(trimethylsilyl)ethoxy)methyl)-1H-imidazole-4-carboxamide (S)-2-Acetyl-N-(1-(3-(3-chloro-4-cyano-5-fluorophenyl)-1H-pyrazol-1-yl)-propan-2-yl)-1-((2-(trimethylsilyl)ethoxy)methyl)-1H-imidazole-4-carboxamide (290 mg, 0.53 mmol) was dissolved in MeOH (20 ml). $NaBH_4$ (30 mg, 0.79 mmol) was added to the solution in portions at 0° C. and the mixture was stirred at RT for 3 h. The reaction mixture was concentrated and dluted with water. The mixture was extracted with DCM and the organic layer was concentrated. The product was purified by column chromatography. Yield 245 mg. $^1$H-NMR (400 MHz; DMSO-d$_6$): δ −0.05 (s, 9H), 0.81-0.86 (m, 2H), 1.07-1.1 (m, 3H), 1.49 (d, 3H), 3.47-3.51 (m, 2H), 4.29-4.43 (m, 3H), 4.88-4.91 (m, 1H), 5.4-5.45 (m, 3H), 7.03 (d, 1H), 7.68 (d, 1H), 7.86-8.00 (m, 4H).

f) N—((S)-1-(3-(3-Chloro-4-cyano-5-fluorophenyl)-1H-pyrazol-1-yl)propan-2-yl)-2-(1-hydroxyethyl)-1H-imidazole-4-carboxamide The title compound was prepared using the procedure described in Example 52(h) starting from N—((S)-1-(3-(3-chloro-4-cyano-5-fluorophenyl)-1H-pyrazol-1-yl)propan-2-yl)-2-(1-hydroxyethyl)-1-((2-(trimethylsilyl)ethoxy)methyl)-1H-imidazole-4-carboxamide (0.65 g, 1.2 mmol). Yield 124 mg. $^1$H-NMR (400 MHz; DMSO-d$_6$): δ 1.07 (d, 3H), 1.41 (d, 3H), 4.27-4.41 (m, 3H), 4.73-4.78 (m, 1H), 5.51 (d, 1H), 7.03 (d, 1H), 7.41 (s, 1H), 7.86 (d, 1H), 7.92 (d, 1H), 8.01 (d, 2H), 12.28 (s, 1H).

Example 34

(S)-2-acetyl-N-(1-(3-(3-chloro-4-cyano-5-fluorophenyl)-1H-pyrazol-1-yl)-propan-2-yl)-1H-imidazole-4-carboxamide a) (S)-2-Acetyl-N-(1-(3-(3-chloro-4-cyano-5-fluorophenyl)-1H-pyrazol-1-yl)-propan-2-yl)-1-((2-(trimethylsilyl)ethoxy)methyl)-1H-imidazole-4-carboxamide The title compound was prepared using the procedure described in Example 32(e) starting from starting from 2-acetyl-1-((2-(trimethylsilyl)ethoxy)methyl)-1H-imidazole-4-carboxylic acid (400 mg, 1.4 mmol) and (S)-4-(1-(2-aminopropyl)-1H-pyrazol-3-yl)-2-chloro-6-fluorobenzonitrile (389 mg, 1.4 mmol). The product was purified with flash-chromatography. Yield: 260 mg. $^1$H-NMR (400 MHz; DMSO-$d_6$): δ −0.09 (s, 9H), 0.81 (t, 2H), 1.15 (d, 3H), 2.61 (s, 3H), 3.48 (t, 2H), 4.33-4.48 (m, 3H), 5.66 (s, 2H), 7.02 (d, 1H), 7.84-7.87 (m, 2H), 7.95 (s, 1H), 8.06 (s, 1H), 8.15 (d, 1H).

b) (S)-2-Acetyl-N-(1-(3-(3-chloro-4-cyano-5-fluorophenyl)-1H-pyrazol-1-yl)propan-2-yl)-1H-imidazole-4-carboxamide The title compound was prepared using the procedure described in Example 52(h) starting from (S)-2-acetyl-N-(1-(3-(3-chloro-4-cyano-5-fluorophenyl)-1H-pyrazol-1-yl)propan-2-yl)-1-((2-(trimethylsilyl)ethoxy)methyl)-1H-imidazole-4-carboxamide (250 mg, 0.45 mmol). Yield 124 mg. $^1$H-NMR (400 MHz; DMSO-$d_6$): δ 1.14 (d, 3H), 2.57 (s, 3H), 4.31-4.5 (m, 3H), 7.02 (d, 1H), 7.78 (d, 1H), 7.84-7.87 (m, 2H), 7.94 (s, 1H), 8.11 (d, 1H), 13.62 (s, 1H).

Example 35

(S)—N-(1-(3-(3-Chloro-4-cyano-5-fluorophenyl)-1H-pyrazol-1-yl)propan-2-yl)-2-(2-hydroxypropan-2-yl)-1H-imidazole-4-carboxamide a) Methyl 2-(2-hydroxypropan-2-yl)-1-((2-(trimethylsilyl)ethoxy)methyl)-1H-imidazole-4-carboxylate The title compound was prepared using the procedure described in Example 2(d) starting from methyl 2-acetyl-1-((2-(trimethylsilyl)-ethoxy)methyl)-1H-imidazole-4-carboxylate (3 g, 10 mmol). The product was purified by flash-chromatography. Yield 1.5 g. $^1$H-NMR (400 MHz; DMSO-$d_6$): δ −0.03 (s, 9H), 0.86 (t, 2H), 1.52 (s, 6H), 3.56 (t, 2H), 3.73 (s, 3H), 5.64 (s, 2H), 7.94 (s, 1H).

b) 2-(2-Hydroxypropan-2-yl)-1-((2-(trimethylsilyl)ethoxy)methyl)-1H-imidazole-4-carboxylic acid The title compound was prepared using the procedure described in Example 32(d) starting from methyl 2-(2-hydroxypropan-2-yl)-1-((2-(trimethylsilyl)ethoxy)-methyl)-1H-imidazole-4-carboxylate (1.5 g, 4.7 mmol). Yield 1 g. $^1$H-NMR (400 MHz; DMSO-$d_6$): δ −0.02 (s, 9H), 0.86 (t, 2H), 1.52 (s, 6H), 3.56 (t, 2H), 5.44 (s, 1H), 5.62 (s, 2H), 7.83 (s, 1H).

c) (S)—N-(1-(3-(3-Chloro-4-cyano-5-fluorophenyl)-1H-pyrazol-1-yl)propan-2-yl)-2-(2-hydroxypropan-2-yl)-1-((2-(trimethylsilyl)ethoxy)methyl)-1H-imidazole-4-carboxamide The title compound was prepared using the procedure described in Example 32(e) starting from 2-(2-hydroxypropan-2-yl)-1-((2-(trimethylsilyl)ethoxy)-methyl)-1H-imidazole-4-carboxylic acid (400 mg, 1.33 mmol) and (S)-4-(1-(2-amino-propyl)-1H-pyrazol-3-yl)-2-chloro-6-fluorobenzonitrile (370 mg, 1.33 mmol). The product was purified with flash-chromatography. Yield 305 mg. LC-MS: [M+1]=561.17.

d) (S)—N-(1-(3-(3-Chloro-4-cyano-5-fluorophenyl)-1H-pyrazol-1-yl)propan-2-yl)-2-(2-hydroxypropan-2-yl)-1H-imidazole-4-carboxamide The title compound was prepared using the procedure described in Example 52(h) starting from (S)—N-(1-(3-(3-chloro-4-cyano-5-fluorophenyl)-1H-pyrazol-1-yl)propan-2-yl)-2-(2-hydroxy-propan-2-yl)-1-((2-(trimethylsilyl)ethoxy)methyl)-1H-imidazole-4-carboxamide (370 mg, 0.66 mmol). Yield 136 mg. $^1$H-NMR (400 MHz; DMSO-$d_6$): δ 1.09 (d, 3H), 1.46 (s, 6H), 4.28-4.42 (m, 3H), 5.35 (s, 1H), 7.04 (d, 1H), 7.38 (d, 1H), 7.75-7.99 (m, 4H), 12.15 (s, 1H).

Example 36

(S)—N-(1-(3-(3-Chloro-4-cyano-5-fluorophenyl)-1H-pyrazol-1-yl)-propan-2-yl)-2-cyclopropyl-1-methyl-1H-imidazole-4-carboxamide The title compound was prepared using the procedure described in Example 32(e) starting from 2-cyclopropyl-1-methyl-1H-imidazole-4-carboxylic acid (260 mg, 1.56 mmol) and (S)-4-(1-(2-aminopropyl)-1H-pyrazol-3-yl)-2-chloro-6-fluorobenzo-nitrile (435 mg, 1.56 mmol). Yield 123 mg. $^1$H-NMR (400 MHz; DMSO-$d_6$): δ 0.81-0.91 (m, 4H), 1.08 (d, 3H), 1.95 (m, 1H), 3.65 (s, 3H), 4.27-4.38 (m, 3H), 7.01 (s, 1H), 7.46 (s, 1H), 7.69 (d, 1H), 7.87 (d, 2H), 7.96 (s, 1H).

Example 37

(S)—N$^4$-(1-(3-(3-Chloro-4-cyano-5-fluorophenyl)-1H-pyrazol-1-yl)propan-2-yl)-1H-imidazole-2,4-dicarboxamide a) Methyl 2-cyano-1-((2-(trimethylsilyl)ethoxy)methyl)-1H-imidazole-4-carboxylate Into a flask containing a solution of methyl 2-formyl-1-((2-(trimethylsilyl)-ethoxy)-methyl)-1H-imidazole-4-carboxylate (9 g, 31.6 mmol) in MeOH (200 ml), 50% aqueous NH$_2$OH.HCl solution (2.5 ml) was added and stirred at RT for 3 h. The reaction mixture was concentrated and extracted with EtOAc. The organic layer was concentrated and the resulting residue was dissolved in DCM (200 ml). Pyridine (12 ml) and trifluoroacetic anhydride (18 ml) were added to the above mixture and stirred for 12 h. The reaction mixture was quenched with aqueous NaHCO$_3$ solution and extracted with DCM. The organic layer was concentrated and purified with flash chromatography. Yield 4.1 g. $^1$H-NMR (400 MHz; DMSO-$d_6$): δ −0.04 (s, 9H), 0.87 (t, 2H), 3.56 (t, 2H), 3.81 (s, 3H), 5.29 (s, 2H), 8.28 (s, 1H).

b) 2-Carbamoyl-1-((2-(trimethylsilyl)ethoxy)methyl)-1H-imidazole-4-carboxylic acid Methyl 2-cyano-1-((2-(trimethylsilyl)ethoxy)methyl)-1H-imidazole-4-carboxylate (3 g, 10.7 mmol) was dissolved in THF (30 ml) and H$_2$O (8 ml). LiOH.H$_2$O (1.1 g, 16.1 mmol) was added to the solution and the mixture was stirred at RT overnight. The reaction mixture was concentrated and acidified to pH 2 using 1 N HCl. The mixture was extracted with EtOAc and the organic layer was concentrated. Yield 2.2 g. $^1$H-NMR (400 MHz; DMSO-$d_6$): δ −0.06 (s, 9H), 0.85 (t, 2H), 2.57 (s, 3H), 3.52 (t, 2H), 5.79 (s, 2H), 7.66 (s, 1H), 7.96 (s, 1H), 8.09 (s, 1H), 12.68 (s, 1H).

c) (S)—N⁴-(1-(3-(3-Chloro-4-cyano-5-fluorophenyl)-1H-pyrazol-1-yl)propan-2-yl)-1-((2-(trimethylsilyl)ethoxy)methyl)-1H-imidazole-2,4-dicarboxamide The title compound was prepared using the procedure described in Example 32(e) starting from 2-carbamoyl-1-((2-(trimethylsilyl)ethoxy)methyl)-1H-imidazole-4-carboxylic acid (500 mg, 1.7 mmol) and (S)-4-(1-(2-aminopropyl)-1H-pyrazol-3-yl)-2-chloro-6-fluorobenzonitrile (472 mg, 1.7 mmol). The product was purified with flash-chromatography. Yield 420 mg. LC-MS: [M+1]=546.19.

d) (S)—N⁴-(1-(3-(3-Chloro-4-cyano-5-fluorophenyl)-1H-pyrazol-1-yl)propan-2-yl)-1H-imidazole-2,4-dicarboxamide The title compound was prepared using the procedure described in Example 52(h) starting from (S)—N⁴-(1-(3-(3-chloro-4-cyano-5-fluorophenyl)-1H-pyrazol-1-yl)propan-2-yl)-1-((2-(trimethylsilyl)ethoxy)-methyl)-1H-imidazole-2,4-dicarboxamide (0.45 g, 0.82 mmol) Yield 310 mg. $^1$H-NMR (400 MHz; DMSO-$d_6$): δ 1.14 (d, 3H), 4.28-4.24 (m, 3H), 7.01 (s, 1H), 7.63-7.67 (m, 3H), 7.84-7.94 (m, 4H), 13.39 (s, 1H).

Example 38

4-(1-(3-((S)-1-(3-(3-Chloro-4-cyanophenyl)-1H-pyrazol-1-yl)propan-2-yl-carbamoyl)-1H-pyrazol-5-yl)ethoxy)-4-oxobutanoic acid a) 2-Chloro-4-(1-(tetrahydro-2H-pyran-2-yl)-1H-pyrazol-5-yl)benzonitrile 4-Bromo-2-chlorobenzonitrile (30 g, 139 mmol), 90 ml of THF and 360 ml of toluene were placed in reaction vessel under nitrogen atmosphere. Bis(triphenylphosphine)-palladium(II) chloride (4.57 g, 6.51 mmol), $Na_2CO_3$ (33.1 g, 312 mmol), 180 ml of water and tetrabutylammonium bromide (0.894 g, 2.77 mmol) were added. The reaction mixture was heated up to 42° C. 1-(Tetrahydro-2H-pyran-2-yl)-1H-pyrazole-5-boronic acid pinacol ester (42.4 g; 152 mmol) was added in three portions within one hour. The reaction was agitated at 42° C. for one hour followed with addition of 180 ml of water and cool down. The reaction mixture was filtered and layers separated. Organic phase was washed with 400 ml of water. The layers were separated and the toluene phase was distilled close to dryness. 180 ml of ethanol was added to the warm residue and the mixture was cooled down to 5° C. for three hours. The precipitate was filtered and washed with cold ethanol. 36.4 g of the title compound was obtained after vacuum drying. $^1$H-NMR (400 MHz, DMSO-$d_6$): δ 1.48-1.70 (m, 3H), 1.78-1.86 (m, 1H), 1.90-2.00 (m, 1H), 2.29-2.46 (m, 1H), 3.55-3.68 (m, 1H), 3.93-4.04 (m, 1H), 5.29 (dd, 1H), 6.72 (d, 1H), 7.65 (d, 1H), 7.72 (dd, 1H), 7.92 (d, 1H), 8.13 (d, 1H).

b) 2-Chloro-4-(1H-pyrazol-3-yl)benzonitrile hydrochloride

HCl/EtOH ~10% (35.1 ml, 115 mmol) was set into the reaction flask under nitrogen atmosphere. 2-Chloro-4-(1-(tetrahydro-2H-pyran-2-yl)-1H-pyrazol-5-yl)-benzonitrile (12 g, 46.2 mmol) was added. The mixture was cooled to 10° C. and agitated for 2 h. Temperature was set to 0° C. and the mixture was stirred additional 2 hours. The precipitation was filtered, washed with ethanol and dried under vacuum overnight to obtain 9.24 g of the title compound. $^1$H-NMR (400 MHz, DMSO-$d_6$): δ 6.99 (d, 3H), 7.86 (d, 1H), 7.96-8.02 (m, 2H), 8.14-8.17 (m, 1H).

c) 2-Chloro-4-(1H-pyrazol-3-yl)benzonitrile

2-Chloro-4-(1H-pyrazol-5-yl)benzonitrile hydrochloride (8 g, 33.3 mmol) was charged to the reaction flask and methanol (74 ml), activated charcoal (0.36 g) and celite (0.46 g) were added. The reaction mixture was refluxed for 1 h, filtered, and the solid was washed with warm methanol. A half of the methanol was distilled out and water (40 ml) was added at 55° C. slowly. 50% NaOH solution (1.916 ml, 36.7 mmol) was added slowly, the mixture was stirred for 10 min and cooled to RT. MeOH was evaporated and residue cooled to RT. Water (49 ml) was added and the precipitate was filtered and washed with water and dried under vacuum overnight at 60° C. to obtain 6.21 g of the title compound. $^1$H-NMR (400 MHz, DMSO-$d_6$): δ 6.99 (d, 1H), 7.86 (d, 1H), 7.96-8.01 (m, 2H), 8.24-8.16 (m, 1H).

d) (S)-4-(1-(2-Aminopropyl)-1H-pyrazol-3-yl)-2-chlorobenzonitrile

2-Chloro-4-(1H-pyrazol-3-yl)benzonitrile (30 g, 145 mmol), (S)-tert-butyl-1-hydroxypropan-2-ylcarbamate (51.4 g, 291 mmol), triphenylphosphine (77 g, 291 mmol) and 210 ml of EtOAc were place in to the reaction vessel under nitrogen atmosphere and stirred for 15 min. DIAD (57.8 ml, 291 mmol) was added slowly in 1.5 h at RT keeping the temperature stable and the reaction was stirred overnight at RT. Concentrated HCl (134 ml, 1453 mmol) was added and the mixture was stirred at RT overnight. Water (165 ml) and DCM (240 ml) were added, the mixture was stirred for 30 min and layers were separated. Organic phase was washed with 2×270 ml of acidic water (pH~1). Water phases were combined and washed with 2×120 ml of dichloromethane. Dichloromethane (150 ml) was added, pH set to 11.5 by 50% NaOH and the mixture was stirred for 75 min. The solution was filtered through the celite, layers were separated and organic phase was washed with 171 ml of water. DCM was distilled out at 33° C. under reduced pressure and 60 ml of heptanes was added. Precipitation was started, 60 ml of heptane added and the mixture was stirred overnight. Some DCM was evaporated, 60 ml heptanes was added and the mixture was cooled to 10° C. The precipitate was filtered, washed with 20 ml of IPA:heptane (10:90) and dried under vacuum to obtain 24.55 g of the title compound. $^1$H-NMR (400 MHz, DMSO-$d_6$): δ 1.03 (d, 3H), 3.34-3.43 (d, 2H), 4.14 (d, 2H), 6.99 (d, 1H), 7.89 (d, 1H), 7.96 (dd, 1H), 7.99 (dd, 1H), 8.12-8.14 (m, 1H).

e) (S)-5-Acetyl-N-(1-(3-(3-Chloro-4-cyanophenyl)-1H-pyrazol-1-yl)propan-2-yl)-1H-pyrazole-3-carboxamide 3-Acetyl-1H-pyrazole-5-carboxylic acid (10.20 g, 66.2 mmol), DCM (195 ml) and DIPEA (11.52 ml, 66.2 mmol) were placed in to the reaction flask under nitrogen atmosphere. HBTU (3.27 g, 8.63 mmol), EDCI (12.68 g, 66.2 mmol) and (S)-4-(1-(2-aminopropyl)-1H-pyrazol-3-yl)-2-chlorobenzonitrile (15 g, 57.5 mmol) were added in this order and the mixture was stirred overnight at RT. The solvent was distilled close to dryness under vacuum, 2-propanol (25 ml) was added and the mixture was distilled to dryness. 2-Propanol (127 ml) was added, heated to reflux, water (23 ml) was added and the mixture was stirred for 15 min. The mixture was cooled to RT, stirred overnight and cooled to 5° C. The precipitate was filtered, washed with 2×10 ml of cold 2-propanol:water (70:30) and dried under vacuum to obtain 18.7 g of the title compound. $^1$H-NMR (400 MHz, DMSO-d$_6$): δ 1.17 (d, 3H), 2.50 (s, 3H), 4.21-4.53 (m, 3H), 6.93 (d, 1H), 7.31 (s, 1H), 7.81 (d, 1H), 7.86-8.07 (m, 3H), 8.40-8.54 (bs, 1H), 14.14 (bs., 1H).

f) N—((S)-1-(3-(3-Chloro-4-cyanophenyl)-1H-pyrazol-1-yl)propan-2-yl)-5-(1-hydroxyethyl)-1H-pyrazole-3-carboxamide Sodium borohydride (0.930 g, 24.57 mmol) and EtOH (105 ml) were placed in to the reaction flask under nitrogen atmosphere. (S)-3-acetyl-N-(1-(3-(3-chloro-4-cyano-phenyl)-1H-pyrazol-1-yl)propan-2-yl)-1H-pyrazole-5-carboxamide (15 g, 37.8 mmol) was added in small portions to keep temperature below 25° C. After 3.5 h sodium borohydride (0.07 g, 1.85 mmol) was added and the mixture was stirred for additional 60 min to complete the reaction. 16 ml of ~10% HCl in EtOH was added carefully to set pH to 3.5 and the mixture was stirred overnight at RT. Water (30 ml) was added and the stirring was continued for 3 h. The precipitate was filtered, washed with 2×10 ml of cold water:EtOH (1:1) and dried under vacuum to obtain 12.2 g of the title compound. $^1$H-NMR (400 MHz, DMSO-d$_6$): δ 1.12 (d, 3H), 1.39 (d, 3H), 4.24-4.52 (m, 3H), 4.76-4.86 (m, 1H), 5.42 (d, 1H), 6.42 (bs., 1H), 6.94 (d, 1H), 7.82 (d, 1H), 8.00 (bs, 2H), 8.09 (bs, 1H), 8.20 (d, 1H), 13.05 (bs, 1H).

g) 4-(1-(3-((S)-1-(3-(3-Chloro-4-cyanophenyl)-1H-pyrazol-1-yl)propan-2-ylcarbamoyl)-1H-pyrazol-5-yl)ethoxy)-4-oxobutanoic acid N—((S)-1-(3-(3-Chloro-4-cyanophenyl)-1H-pyrazol-1-yl)propan-2-yl)-5-(1-hydroxy-ethyl)-1H-pyrazole-3-carboxamide (1.254 mmol, 0.5 g), dihydrofuran-2,5-dione (1.504 mmol, 0.151 g) and 4-dimethylaminopyridine (0.1254 mmol, 0.015 g) were dissolved in THF (10 ml) and DMF (1 ml). The resulting mixture was stirred at RT for one day after which the temperature was raised to 50° C. for one day. The mixture was stirred at RT over the weekend. During the reaction more dihydrofuran-2,5-dione (50 mg) was added. The solvents were evaporated and the residue was dissolved in EtOAc. The organic phase was washed with 1 M HCl, separated, dried, filtered and evaporated. The crude product was purified by flash chromatography. 352 mg of the title compound was obtained. $^1$H-NMR (400 MHz, CDCl$_3$): δ 1.22-1.28 (m, 3H), 1.61-1.69 (m, 3H), 2.54-2.79 (m, 4H), 4.29-4.45 (m, 2H), 4.52-4.64 (m, 1H), 5.97-6.06 (m, 1H), 6.58-6.62 (m, 1H), 6.76-6.80 (m, 1H), 7.50-7.53 (m, 1H), 7.62-7.68 (m, 1H), 7.70-7.77 (m, 1H), 7.90-8.04 (m, 2H).

Example 39

(S)-5-Chloro-N-(1-(3-(3-chloro-4-cyanophenyl)-1H-pyrazol-1-yl)-propan-2-yl)pyrazine-2-carboxamide a) 5-Chloropyrazine-2-carbonyl chloride 5-Chloropyrazine-2-carboxylic acid (3.15 mmol, 500 mg) was dissolved in DCM (55 ml). Oxalyl dichloride (6.62 mmol, 841 mg) was added slowly and the resulting mixture was refluxed for 2 h. After, the reaction had stopped the mixture was concentrated. 580 mg of the title compound was obtained. $^1$H-NMR (400 MHz, CDCl$_3$) δ 8.78 (d, 1H), 9.09 (d, 1H).

b) (S)-5-Chloro-N-(1-(3-(3-chloro-4-cyanophenyl)-1H-pyrazol-1-yl)propan-2-yl)pyrazine-2-carboxamide 5-Chloropyrazine-2-carbonyl chloride (3.28 mmol, 580 mg) was dissolved in dry THF (40 ml). Triethylamine (9.83 mmol, 995 mg) and (S)-4-(1-(2-aminopropyl)-1H-pyrazol-3-yl)-2-chlorobenzonitrile (3.28 mmol, 854 mg) were added and the resulting mixture was stirred for one day at RT. The crude product was purified by recrystallization from DCM. 900 mg of the title compound was obtained. $^1$H-NMR (400 MHz, CDCl$_3$): δ 1.25 (d, 3H), 4.29 (dd, 1H), 4.47 (dd, 1H), 4.59-4.71 (m, 1H), 6.66 (d, 1H), 7.51 (d, 1H), 7.68-7.73 (m, 1H), 7.75-7.80 (m, 1H), 8.12 (d, 1H), 8.64 (d, 1H), 8.77 (d, 1H), 9.17 (d, 1H).

Example 40

N—((S)-1-(3-(3-Chloro-4-cyanophenyl)-1H-pyrazol-1-yl)propan-2-yl)-1-((S)-2-hydroxypropyl)-2-methyl-1H-imidazole-4-carboxamide a) (S)—N-(1-(3-(3-chloro-4-cyanophenyl)-1H-pyrazol-1-yl)propan-2-yl)-2-methyl-1H-imidazole-4-carboxamide 2-Methyl-1H-imidazole-4-carboxylic acid (29.0 g, 230 mmol), 335 ml of DMF and 165 ml of DCM were placed in to the reaction vessel under nitrogen. HBTU (7.27 g, 19.18 mmol), EDCI (44.1 g, 230 mmol) and 66.8 ml of DIPEA were added. (S)-4-(1-(2-aminopropyl)-1H-pyrazol-3-yl)-2-chlorobenzonitrile (50 g, 192 mmol) was added and the reaction stirred overnight at RT. 600 ml of water was slowly added and water phase was washed with 335 ml and 500 ml of DCM. DCM phases were combined, washed with 3×600 ml of water and distilled to dryness. Acetonitrile (300 ml) was added and the mixture was heated up to 75° C. Water (300 ml) was added at >60° C., solution was allowed to cool to RT for precipitation and the mixture was stirred overnight at RT. Stirring was continued for additional 2 h at <10° C. The precipitate was filtered, washed with cold ACN:water and dried under vacuum to obtain 47 g of crude product. The title compound was recrystallized from EtOH with 75% yield. $^1$H-NMR (400 MHz, DMSO-d$_6$): δ 1.08 (d, 3H), 2.30 (s, 3H), 4.23-4.48 (m, 3H), 6.95 (d, 1H), 7.41 (s, 1H), 7.82 (d, 1H), 7.95-8.07 (m, 3H), 8.09-8.12 (m, 1H), 12.12 (bs, 1H).

b) N—((S)-1-(3-(3-Chloro-4-cyanophenyl)-1H-pyrazol-1-yl)propan-2-yl)-1-((S)-2-hydroxypropyl)-2-methyl-1H-imidazole-4-carboxamide (S)—N-(1-(3-(3-Chloro-4-cyanophenyl)-1H-pyrazol-1-yl)propan-2-yl)-2-methyl-1H-imidazole-4-carboxamide (0.271 mmol, 100 mg) and potassium carbonate (2.71 mmol, 375 mg) were dissolved in dry DMF (3 ml) under nitrogen atmosphere. (S)-2-methyl-oxirane (0.298 mmol, 0.021 ml) was added and the resulting mixture was stirred for 2.5 h at RT. The mixture was heated to 60° C. for two days during which more (S)-2-methyloxirane (0.252 ml) was added. The solvent was evaporated and the residue was purified by flash chromatography. 63 mg of the title compound was obtained. $^1$H-NMR (400 MHz, DMSO-d$_6$): δ 1.05 (d, 3H), 1.07 (d, 3H), 2.34 (s, 3H), 3.67-3.93 (m, 3H), 4.20-4.50 (m, 3H), 4.92 (bs, 1H), 6.95 (d, 1H), 7.47 (s, 1H), 7.83 (d, 1H), 7.98-8.00 (m, 2H), 8.04 (d, 1H), 8.11-8.12 (m, 1H).

Example 41

(S)-1-Butyl-N-(1-(3-(3-chloro-4-cyanophenyl)-1H-pyrazol-1-yl)propan-2-yl)-2-methyl-1H-imidazole-4-carboxamide (S)—N-(1-(3-(3-Chloro-4-cyanophenyl)-1H-pyrazol-1-yl)propan-2-yl)-2-methyl-1H-imidazole-4-carboxamide (0.407 mmol, 150 mg), triphenylphosphine (0.610 mmol, 160 mg) and 1-butanol (0.610 mmol, 45.2 mg) were dissolved in dry THF (5 ml) under nitrogen atmosphere. DIAD (0.610 mmol, 123 mg) was slowly added. The resulting mixture was stirred overnight at RT. At this point the amounts of 1-butanol, triphenylphosphine and DIAD were doubled and the stirring continued for another day. The solvent was evaporated and the residue was purified by flash chromatography and preparative HPLC, respectively. 22.8 mg of the title compound was obtained. $^1$H-NMR (400 MHz, DMSO-d$_6$): δ 0.88 (t, 3H), 1.07 (d, 3H), 1.18-1.29 (m, 2H), 1.57-1.67 (m, 2H), 2.33 (s, 3H), 3.88 (t, 2H), 4.17-4.48 (m, 3H), 6.95 (d, 1H), 7.50 (s, 1H), 7.82 (d, 1H), 7.95-8.00 (m, 2H), 8.02 (d, 1H), 8.10 (s, 1H).

Example 42

(S)—N-(1-(3-(3-Chloro-4-cyanophenyl)-1H-pyrazol-1-yl)propan-2-yl)-5-(2-hydroxypropan-2-yl)-1H-pyrazole-3-carboxamide The title compound was prepared using the procedure described in Example 3(h) starting from 5-(2-hydroxypropan-2-yl)-1H-pyrazole-3-carboxylic acid (0.646 mmol, 110 mg) and (S)-4-(1-(2-amino-propyl)-1H-pyrazol-3-yl)-2-chlorobenzonitrile (0.539 mmol, 140 mg) using DMF (2 ml) as the solvent. Water was added and the mixture was extracted three times with DCM. The combined organics were washed twice with water. The separated organic phase was evaporated and the residue was purified by flash chromatography and preparative HPLC, respectively. 44.6 mg of the title compound was obtained. $^1$H-NMR (400 MHz; DMSO-d$_6$): δ 1.11 (d, 3H), 1.45 (s, 6H), 4.22-4.52 (m, 3H), 5.31 (s, 1H), 6.37 (s, 1H), 6.94 (d, 1H), 7.81 (d, 1H), 7.88-8.03 (m, 2H), 8.09 (s, 1H), 8.16 (d, 1H), 12.96 (s, 1H).

Example 43

(S)—N-(1-(3-(3-Chloro-4-cyanophenyl)-1H-pyrazol-1-yl)propan-2-yl)-1'-methyl-1'H-1,4'-bipyrazole-3-carboxamide The title compound was prepared using the procedure described in Example 3(h) starting from 1'-methyl-1'H-[1,4'-bipyrazole]-3-carboxylic acid (0.921 mmol, 177 mg) and (S)-4-(1-(2-aminopropyl)-1H-pyrazol-3-yl)-2-chlorobenzonitrile (0.767 mmol, 200 mg) using DMF (2 ml) as the solvent. DCM was added and evaporated. The residue was purified by flash chromatography. The product was further purified by dissolving it in DCM and washing three times with 1 M NaHCO$_3$ and evaporating the separated DCM phase. 220 mg of the title compound was obtained. $^1$H-NMR (400 MHz, DMSO-d$_6$): δ 1.14 (d, 3H), 3.89 (s, 3H), 4.27-4.42 (m, 2H), 4.42-4.53 (m, 1H), 6.76 (d, 1H), 6.95 (d, 1H), 7.83-7.87 (m, 3H), 7.94 (dd, 1H), 8.06 (d, 1H), 8.16 (d, 1H), 8.18 (s, 1H), 8.21 (d, 1H).

Example 44

N—((S)-1-(3-(3-Chloro-4-cyanophenyl)-1H-pyrazol-1-yl)propan-2-yl)-1-((R)-2-hydroxypropyl)-2-methyl-1H-imidazole-4-carboxamide The title compound was prepared using the procedure described in Example 3(h) starting from (R)-1-(2-hydroxypropyl)-2-methyl-1H-imidazole-4-carboxylic acid (1.059 mmol, 195 mg) and (S)-4-(1-(2-aminopropyl)-1H-pyrazol-3-yl)-2-chloro-benzonitrile (0.882 mmol, 230 mg) using DMF (2 ml) as the solvent. DCM was added and evaporated. The residue was purified by flash chromatography. The product was further purified by dissolving it in MeOH/DCM and washing twice with 1 M NaHCO$_3$. The separated organic phase was dried, purified and evaporated. 289 mg of the title compound was obtained. $^1$H-NMR (400 MHz, DMSO-d$_6$): δ 1.02-1.10 (m, 6H), 2.34 (s, 3H), 3.70-3.91 (m, 3H), 4.22-4.48 (m, 3H), 4.92 (d, 1H), 6.95 (d, 1H), 7.47 (s, 1H), 7.83 (d, 1H), 7.97-8.00 (m, 2H), 8.04 (d, 1H), 8.09-8.13 (m, 1H).

Example 45

(S)-2-Bromo-N-(1-(3-(3-chloro-4-cyanophenyl)-1H-pyrazol-1-yl)-propan-2-yl)-1H-imidazole-4-carboxamide The title compound was prepared using the procedure described in Example 3(h) starting from 2-bromo-1H-imidazole-4-carboxylic acid (5.75 mmol, 1.099 g) and (S)-4-(1-(2-aminopropyl)-1H-pyrazol-3-yl)-2-chlorobenzonitrile (3.84 mmol, 1 g) using DMF (10 ml) as the solvent. DCM and water were added, the phases were separated and the water phase was extracted with DCM. The combined organics were washed three times with water. The DCM phase was dried, filtered and evaporated. The crude product was purified by flash chromatography and preparative HPLC, respectively. 37.8 mg of the title compound was obtained. $^1$H-NMR (400 MHz, DMSO-d$_6$): δ 1.09 (d, 3H), 4.23-4.48 (m, 3H), 6.95 (d, 1H), 7.64 (s, 1H), 7.82 (d, 1H), 7.94-8.05 (m, 2H), 8.08 (s, 1H), 8.21 (d, 1H), 13.22 (bs, 1H).

Example 46

N—((S)-1-(3-(3-Chloro-4-cyanophenyl)-1H-pyrazol-1-yl)propan-2-yl)-5-(1-hydroxy-2-methylpropyl)isoxazole-3-carboxamide The title compound was prepared using the procedure described in Example 3(h) starting from 5-(1-hydroxy-2-methyl-propyl)isoxazole-3-carboxylic acid (1.566 mmol, 290 mg) and (S)-4-(1-(2-amino-propyl)-1H-pyrazol-3-yl)-2-chlorobenzonitrile (1.044 mmol, 272 mg) using a mixture of DCM (5 ml) and DMF (1 ml) as the solvent. DCM and water were added, the phases were separated and the water phase was extracted with DCM. The combined organics were washed twice with water. The DCM phase was dried, filtered and evaporated. The crude product was purified by flash chromatography and preparative HPLC, respectively. 23.4 mg of the title compound was obtained. $^1$H-NMR (400 MHz, CDCl$_3$): δ 0.94 (d, 3H), 0.98 (d, 3H), 1.23 (d, 3H), 2.06-2.21 (m, 1H), 4.21-4.30 (m, 1H), 4.37-4.46 (m, 1H), 4.51-4.67 (m, 2H), 6.57-6.65 (m, 2H), 7.50 (d, 1H), 7.68 (d, 1H), 7.78-7.86 (m, 1H), 7.97 (d, 1H), 8.04 (s, 1H).

Example 47

(S)—N-(1-(3-(3-Chloro-4-cyanophenyl)-1H-pyrazol-1-yl)propan-2-yl)-1-(2-cyanoethyl)-2-methyl-1H-imidazole-4-carboxamide Sodium hydroxide, 5 M (1.085 mmol, 0.217 ml) and (S)—N-(1-(3-(3-chloro-4-cyano-phenyl)-1H-pyrazol-1-yl)propan-2-yl)-2-methyl-1H-imidazole-4-carboxamide (0.542 mmol, 200 mg) were dissolved in DMF (2 ml). The mixture was cooled to ~10° C. with an ice bath and 3-bromopropionitrile (0.813 mmol, 109 mg) was slowly added. The reaction mixture was allowed to warm to RT and it was stirred overnight. The liquids were, evaporated. DCM was added and washed twice with water. The separated organic phase was dried, filtered and evaporated. The crude product was purified by flash chromatography and preparative HPLC, respectively. 73.1 mg of the title compound was obtained. $^1$H-NMR (400 MHz, DMSO-$d_6$): δ 1.07 (d, 3H), 2.38 (s, 3H), 3.02 (t, 2H), 4.22 (t, 2H), 4.24-4.47 (m, 3H), 6.95 (d, 1H), 7.61 (s, 1H), 7.83 (d, 1H), 7.96-8.02 (m, 2H), 8.07-8.13 (m, 2H).

Example 48

N—((S)-1-(3-(3-Chloro-4-cyanophenyl)-1H-pyrazol-1-yl)propan-2-yl)-1-(1-cyanoethyl)-2-methyl-1H-imidazole-4-carboxamide Sodium hydroxide, 5 M (1.085 mmol, 0.217 ml) and (S)—N-(1-(3-(3-chloro-4-cyano-phenyl)-1H-pyrazol-1-yl)propan-2-yl)-2-methyl-1H-imidazole-4-carboxamide (0.542 mmol, 200 mg) were dissolved in DMF (2 ml). The mixture was cooled to ~10° C. with an ice bath and 2-bromopropanenitrile (0.813 mmol, 109 mg) was slowly added. The mixture was allowed to warm to RT and it was stirred for 2 h. Solvent was evaporated, DCM was added and the mixture was washed twice with water. The organic phase was dried, filtered and evaporated. The crude product was purified by flash chromatography and trituration from diethyl ether. 63 mg of the title compound was obtained. $^1$H-NMR (400 MHz, DMSO-$d_6$): δ 1.04-1.12 (m, 3H), 1.77 (d, 3H), 2.42 (s, 3H), 4.23-4.49 (m, 3H), 5.72 (q, 1H), 6.92-6.97 (m, 1H), 7.79-7.85 (m, 2H), 7.95-8.01 (m, 2H), 8.08-8.11 (m, 1H), 8.15 (d, 1H).

Example 49

(S)—N-(1-(3-(3-Chloro-4-cyanophenyl)-1H-pyrazol-1-yl)propan-2-yl)-1-(2-methylprop-1-enyl)-1H-pyrazole-3-carboxamide The title compound was prepared using the procedure described in Example 3(h) starting from 1-(2-methylprop-1-en-1-yl)-1H-pyrazole-3-carboxylic acid (1.151 mmol, 191 mg) and (S)-4-(1-(2-amino-propyl)-1H-pyrazol-3-yl)-2-chlorobenzonitrile (0.959 mmol, 250 mg) using DCM (5 ml) as the solvent. The mixture was diluted with DCM and washed with 1 M $Na_2CO_3$. The organic phase was dried, filtered and evaporated. The crude product was purified flash chromatography. 297 mg of the title compound was obtained. $^1$H-NMR (400 MHz, DMSO-$d_6$): δ 1.12 (d, 3H), 1.80 (d, 3H), 1.85 (d, 3H), 4.25-4.52 (m, 3H), 6.66 (d, 1H), 6.77-6.81 (m, 1H), 6.95 (d, 1H), 7.83 (t, 2H), 7.94-7.97 (m, 2H), 8.06-8.10 (m, 1H), 8.18 (d, 1H).

Example 50

(S)—N-(1-(3-(3-Chloro-4-cyanophenyl)-1H-pyrazol-1-yl)propan-2-yl)-3-(1H-imidazol-4-yl)-1H-pyrazole-5-carboxamide a) (S)—N-(1-(3-(3-Chloro-4-cyanophenyl)-1H-pyrazol-1-yl)propan-2-yl)-3-(1-trityl-1H-imidazol-4-yl)-1H-pyrazole-5-carboxamide The title compound was prepared using the procedure described in Example 3(h) starting from 3-(1-trityl-1H-imidazol-4-yl)-1H-pyrazole-5-carboxylic acid (2.493 mmol, 1048 mg) and (S)-4-(1-(2-aminopropyl)-1H-pyrazol-3-yl)-2-chloro-benzonitrile (1.918 mmol, 500 mg) using a mixture of DCM (10 ml) and DMF (1 ml) as the solvent. HBTU (0.384 mmol, 145 mg) was used instead of HOBt. The reaction mixture was diluted with DCM and washed with 1 M $Na_2CO_3$ and water. The separated organic phase was dried, filtered and evaporated. 1.637 g of the title compound was obtained. $^1$H-NMR (400 MHz, DMSO-$d_6$): δ 1.12 (d, 3H), 4.17-4.52 (m, 3H), 6.75 (bs., 1H), 6.92 (d, 1H), 7.12-7.19 (m, 7H), 7.35-7.53 (m, 12H), 7.80 (d, 1H), 7.97 (bs, 1H), 8.04 (s, 1H), 8.21 (d, 1H), 13.38 (bs., 1H).

b) (S)—N-(1-(3-(3-Chloro-4-cyanophenyl)-1H-pyrazol-1-yl)propan-2-yl)-3-(1H-imidazol-4-yl)-1H-pyrazole-5-carboxamide Formic acid (452 mmol, 20.82 g) was dissolved in a mixture of water (2 ml) and THF (40 ml). (S)—N-(1-(3-(3-chloro-4-cyanophenyl)-1H-pyrazol-1-yl)propan-2-yl)-3-(1-trityl-1H-imidazol-4-yl)-1H-pyrazole-5-carboxamide (1.508 mmol, 1 g) was added and the resulting mixture was heated to 50° C. for 3 h. The stirring continued for 2 days at RT. The mixture was concentrated. ACN was added and evaporated. This was repeated once more. The crude product was purified by flash chromatography. 0.371 g of the title compound was obtained. $^1$H-NMR (400 MHz, DMSO-$d_6$): δ 1.14 (d, 3H), 4.23-4.56 (m, 3H), 6.76 (bs, 1H), 6.94 (d, 1H), 7.53 (bs, 1H), 7.76 (s, 1H), 7.83 (d, 1H), 7.95-8.04 (m, 2H), 8.07-8.10 (m, 1H), 8.27 (d, 1H), 12.30 (bs, 1H), 13.40 (bs, 1H).

Example 51

(S)—N-(1-(3-(3-Chloro-4-cyanophenyl)-1H-pyrazol-1-yl)propan-2-yl)-1-cyclopropyl-1H-pyrazole-3-carboxamide The title compound was prepared using the procedure described in Example 32(e) starting from 1-cyclopropyl-1H-pyrazole-3-carboxylic acid (0.300 g, 1.8 mmol) and (S)-4-(1-(2-aminopropyl)-1H-pyrazol-3-yl)-2-chloro-benzonitrile (0.471 g, 1.8 mmol). The product was purified by flash-chromatography. Yield: 400 mg. $^1$H-NMR (400 MHz; DMSO-$d_6$): δ 0.98-1.11 (m, 7H), 3.75-3.80 (m, 1H), 4.25-4.48 (m, 3H), 6.54 (d, 1H), 6.96 (d, 1H), 7.82 (d, 2H), 7.93-7.99 (m, 2H), 8.07 (s, 1H), 8.16 (d, 1H), LC-MS: [M+1]=395.15.

Example 52

(S)—N-(1-(3-(3-Chloro-4-cyanophenyl)-1H-pyrazol-1-yl)propan-2-yl)-1-(6-(dimethylamino)pyridin-3-yl)-1H-pyrazole-3-carboxamide a) Methyl 1H-imidazole-4-carboxylate 1H-Imidazole-4-carboxylic acid (5 g, 44.6 mmol) was dissolved in MeOH (100 ml). Into the solution, $H_2SO_4$ (10 ml)

was added at 0° C. The resulting mixture was stirred at 80° C. for overnight. The solvent was concentrated under reduced pressure. The pH was adjusted to 9 with aqueous NaHCO$_3$ solution and extracted with EtOAc. The organic layer was concentrated to give the product. Yield 5.2 g. $^1$H-NMR (400 MHz; DMSO-d$_6$): δ 3.74 (s, 3H), 7.79 (bs, 2H), 12.75 (bs, 1H). LC-MS: [M+1]=127.23.

b) Methyl 1-((2-(trimethylsilyl)ethoxy)methyl)-1H-imidazole-4-carboxylate

Into a flask containing methyl 1H-imidazole-4-carboxylate (5 g, 39.7 mmol) in DMF (70 ml), K$_2$CO$_3$ (13.7 g, 99.1 mmol), SEM-Cl (9.3 ml, 51.6 mmol) were added and stirred at 80° C. overnight. The reaction mixture was quenched by the addition of H$_2$O and extracted with EtOAc. The organic layer was concentrated and purified by column chromatography. Yield 3.8 g. $^1$H-NMR (400 MHz; DMSO-d$_6$): δ 0.05 (s, 9H), 0.80 (t, 2H), 3.47 (t, 2H), 3.74 (s, 3H), 5.30 (s, 2H), 7.91 (s, 1H), 8.01 (s, 1H). LC-MS: [M+1]=257.27.

c) Methyl 2-bromo-1-((2-(trimethylsilyl)methyl)-1H-imidazole-4-carboxylate

Into a flask containing methyl 1-((2-(trimethylsilyl)ethoxy)methyl)-1H-imidazole-4-carboxylate (4.0 g; 15.6 mmol) in CCl$_4$ (100 ml), catalytic AIBN, NBS (3.1 g, 17.1 mmol) were added and stirred at 65° C. for 3 h. The reaction mixture was quenched with aqueous solution of NaHCO$_3$ and extracted with EtOAc. The organic layer was concentrated and purified by column chromatography. Yield 3.5 g. $^1$H-NMR (400 MHz; DMSO-d$_6$): δ 0.04 (s, 9H), 0.84 (t, 2H), 3.53 (t, 2H), 3.75 (s, 3H), 5.30 (s, 2H), 8.25 (s, 1H). LC-MS: [M+1]=335.01.

d) Methyl 2-formyl-1-((2-(trimethylsilyl)ethoxy)methyl)-1H-imidazole-4-carboxylate Into a flask containing methyl 2-bromo-1-((2-(trimethylsilyl)ethoxy)methyl)-1H-imidazole-4-carboxylate (5 g, 14.9 mmol) in THF (20 ml), 2 M solution of i-PrMgCl in THF (22.4 ml, 44.9 mmol) was added at −40° C. under nitrogen atmosphere. The resulting mixture was allowed to stir for 10 min at −40° C. and cooled to −78° C. The reaction mixture was treated with DMF (7.29 ml, 89.8 mmol) and slowly warmed to RT. The mixture was stirred for 1 h at RT and quenched with saturated aqueous solution of NaHCO$_3$. The crude was extracted with EtOAc. The organic layer was concentrated under reduced pressure. Yield 3 g. LC-MS: [M+1]=285.15.

e) Methyl 2-(hydroxymethyl)-1-((2-(trimethylsilyl)ethoxy)methyl)-1H-imidazole-4-carboxylate Into a flask containing a solution of methyl 2-formyl-1-((2-(trimethylsilyl)-ethoxy)-methyl)-1H-imidazole-4-carboxylate (3 g, 10.5 mmol) in MeOH (20 ml), NaBH$_4$ (0.401 g, 10.5 mmol) was added in portions at 0° C. The resulting mixture was allowed to stir at 0° C. for 30 min followed by RT for 1 hour. The reaction mixture was concentrated and the crude was diluted with water and extracted with EtOAc. The organic layer was concentrated under reduced pressure. Yield 1.5 g. LC-MS: [M+1]=287.17.

f) Methyl 2-((tert-butyldimethylsilyloxy)methyl)-1-((2-(trimethylsilyl)ethoxy)methyl)-1H-imidazole-4-carboxylate Into a flask containing a solution of methyl 2-(hydroxymethyl)-1-((2-(tri-methylsilyl)-ethoxy)methyl)-1H-imidazole-4-carboxylate (1 g, 3.49 mmol) in DMF (25 ml), imidazole (0.490 g, 6.91 mmol), catalytic DMAP and TBDMSCl (0.790 g, 5.27 mmol) were added. The resulting mixture was stirred at RT for 12 h. The reaction mixture was quenched with saturated aqueous solution of NaHCO$_3$ and extracted with EtOAc. The organic layer was concentrated and purified by flash column chromatography. Yield 800 mg. $^1$H-NMR (400 MHz; DMSO-d$_6$): δ −0.04 (s, 9H), 0.05 (s, 6H), 0.80 (t, 2H), 0.86 (s, 9H), 3.49 (t, 2H), 3.74 (s, 3H), 4.71 (s, 2H), 5.41 (s, 2H), 8.02 (s, 1H). LC-MS: [M+1]=401.10.

g) (S)-2-((tert-Butyl dimethylsilyloxy)methyl)-N-(1-(3-(3-chloro-4-cyano phenyl)-1H-pyrazol-1-yl)propan-2-yl)-1-((2-(trimethylsilyl)ethoxy)methyl)-1H-imidazole-4-carboxamide Into a flask containing a solution of (S)-4-(1-(2-aminopropyl)-1H-pyrazol-3-yl)-2-chlorobenzonitrile (0.4 g, 17.5 mmol) in toluene (20 ml), 2 M solution of trimethyl aluminium in heptane (2.62 ml, 52.6 mmol) was added at 0° C. The resulting mixture was stirred at 0° C. for 10 min and a solution of methyl 2-((tert-butyldimethyl-silyloxy)methyl)-1-((2-(trimethylsilyl)ethoxy)methyl)-1H-imidazole-4-carboxylate (0.7 g, 17.5 mmol) in toluene (20 ml) was added at 0° C. The reaction mixture was heated at 110° C. for 4 h and diluted with water. The mixture was filtered through a celite bed and the filtrate was extracted with EtOAc. The organic layer was concentrated under reduced pressure. The product was purified by flash column chromatography. Yield 400 mg. $^1$H-NMR (400 MHz; DMSO-d$_6$): δ −0.05 (s, 9H), 0.05 (s, 6H), 0.82-0.84 (s, 11H), 1.14 (d, 3H), 3.47 (t, 2H), 4.26-4.40 (m, 3H), 4.74 (s, 2H), 5.38 (s, 2H), 6.94 (d, 1H), 7.73 (s, 1H), 7.83 (d, 1H), 7.99 (d, 2H), 8.10 (d, 2H). LC-MS: [M+1]=629.38.

h) (S)—N-(1-(3-(3-Chloro-4-cyanophenyl)-1H-pyrazol-1-yl)propan-2-yl)-2-(hydroxymethyl)-1H-imidazole-4-carboxamide hydrochloride (S)-2-((tert-Butyldimethylsilyloxy)methyl)-N-(1-(3-(3-chloro-4-cyanophenyl)-1H-pyrazol-1-yl)propan-2-yl)-1-((2-(trimethylsilyl)ethoxy)methyl)-1H-imidazole-4-carboxamide (0.4 g, 15.9 mmol) in 6 N HCl (25 ml) was stirred at 45° C. for 24 h. The resulting mixture was evaporated completely and triturated twice from diethyl ether. In the end all precipitates were combined. Yield 200 mg. $^1$H-NMR (400 MHz; DMSO-d$_6$): δ 1.19 (d, 3H), 4.31-4.34 (m, 3H), 4.68 (s, 2H), 6.93 (s, 1H), 7.89-7.95 (m, 3H), 8.05 (s, 1H), 8.30 (s, 1H), 9.15 (d, 1H), 14.8 (bs, 1H).

Example 53

(S)—N-(1-(3-(3-Chloro-4-cyanophenyl)-1H-pyrazol-1-yl)propan-2-yl)-4,5,6,7-tetrahydropyrazolo[1,5-a]pyridine-2-carboxamide)

a) (S)-2-Acetyl-N-(1-(3-(3-chloro-4-cyanophenyl)-1H-pyrazol-1-yl)propan-2-yl)-1-((2-(trimethylsilyl)ethoxy)methyl)-1H-imidazole-4-carboxamide The title compound was prepared using the procedure described in Example 32(e) starting from 2-acetyl-1-((2-(trimethylsilyl)ethoxy)methyl)-1H-imidazole-4-carboxylic acid (300 mg, 1.05 mmol) and (S)-4-(1-(2-aminopropyl)-1H-pyrazol-3-yl)-2-chlorobenzo-nitrile (273 mg, 1.05 mmol). The product was purified with flash-chromatography. Yield 366 mg. $^1$H-NMR (400 MHz; DMSO-d$_6$): δ −0.09 (s, 9H), 0.81 (t, 2H), 1.15 (d, 3H), 2.6 (s, 3H), 3.49 (t, 2H), 4.31-4.47 (m, 3H), 5.66 (s, 2H), 6.95 (s, 1H), 7.85 (d, 1H), 7.92-7.97 (m, 2H), 8.06 (s, 2H), 8.17 (d, 1H).

b) (S)-2-Acetyl-N-(1-(3-(3-chloro-4-cyanophenyl)-1H-pyrazol-1-yl)propan-2-yl)-1H-imidazole-4-carboxamide The title compound was prepared using the procedure described in Example 52(h) starting from (S)-2-acetyl-N-(1-(3-(3-chloro-4-cyanophenyl)-1H-pyrazol-1-yl)propan-2-yl)-1-((2-(trimethylsilyl)ethoxy)-methyl)-1H-imidazole-4-carboxamide (350 mg, 0.66 mmol). Yield 135 mg. $^1$H-NMR (400 MHz; DMSO-$d_6$): δ 1.13 (d, 3H), 2.56 (s, 3H), 4.3-4.5 (m, 3H), 6.96 (s, 1H), 7.78 (d, 1H), 7.85 (d, 1H), 7.96 (s, 2H), 8.06 (s, 1H), 8.13 (d, 1H), 13.61 (s, 1H).

Example 54

N—((S)-1-(3-(3-Chloro-4-cyanophenyl)-1H-pyrazol-1-yl)propan-2-yl)-2-(1-hydroxyethyl)-1H-imidazole-4-carboxamide a) N—((S)-1-(3-(3-Chloro-4-cyanophenyl)-1H-pyrazol-1-yl)propan-2-yl)-2-(1-hydroxyethyl)-1-((2-(trimethylsilyl)ethoxy)methyl)-1H-imidazole-4-carboxamide The title compound was prepared using the procedure described in Example 33(e) starting from (S)-2-acetyl-N-(1-(3-(3-chloro-4-cyanophenyl)-1H-pyrazol-1-yl)propan-2-yl)-1-((2-(trimethylsilyl)ethoxy)-methyl)-1H-imidazole-4-carboxamide (300 mg, 0.57 mmol). The product was purified with flash chromatography. Yield 270 mg. $^1$H-NMR (400 MHz; DMSO-$d_6$): δ −0.05 (s, 9H), 0.84 (t, 2H), 1.08 (d, 3H), 1.49 (d, 3H), 3.45-3.5 (m, 2H), 4.27-4.31 (m, 1H), 4.37-4.46 (m, 2H), 4.87-4.93 (m, 1H), 5.4-5.5 (m, 3H), 6.96 (s, 1H), 7.68 (s, 1H), 7.84 (d, 1H), 7.95-8.03 (m, 3H), 8.11 (d, 1H).

b) N—((S)-1-(3-(3-Chloro-4-cyanophenyl)-1H-pyrazol-1-yl)propan-2-yl)-2-(1-hydroxyethyl)-1H-imidazole-4-carboxamide The title compound was prepared using the procedure described in Example 52(h) starting from N—((S)-1-(3-(3-chloro-4-cyanophenyl)-1H-pyrazol-1-yl)propan-2-yl)-2-(1-hydroxyethyl)-1-((2-(trimethylsilyl)ethoxy)methyl)-1H-imidazole-4-carboxamide (260 mg, 0.49 mmol). The product was purified by flash chromategraphy. Yield 166 mg. $^1$H-NMR (400 MHz; DMSO-$d_6$): δ 1.07 (d, 3H), 1.41 (d, 3H), 4.27-4.46 (m, 3H), 4.78 (s, 1H), 5.51 (d, 1H), 6.96 (d, 1H), 7.42 (d, 1H), 7.84 (d, 1H), 7.90-8.01 (m, 3H), 8.11 (s, 1H), 12.27 (s, 1H).

Example 55

(S)—N-(1-(3-(3-Chloro-4-cyanophenyl)-1H-pyrazol-1-yl)propan-2-yl)-2-isopropyl-1H-imidazole-4-carboxamide a) Methyl 2-isopropyl-1H-imidazole-4-carboxylate

A solution of methyl 1H-imidazole-4-carboxylate (5.0 g, 39.68 mmol), AgNO$_3$ (4.0 g, 23.81 mmol), isobutyric acid (10.4 g, 119.1 mmol) in 10% H$_2$SO$_4$ (150 ml) was heated at 80° C. for 15 min. An aqueous solution of (NH$_4$)$_2$S$_2$O$_8$ (28.0 g, 119.1 mmol) was added to the mixture dropwise in 15 min at 80° C. The reaction mixture was cooled to RT and poured into ice. The mixture was basified with aqueous ammonia (pH 9) and extracted with EtOAc (500 ml). The organic layer was concentrated and the residue was purified by flash chromatography. Yield 1.5 g. $^1$H-NMR (400 MHz; CDCl$_3$): δ 1.36 (d, 6H), 3.05-3.14 (m, 1H), 3.87 (s, 3H), 7.62 (s, 1H).

b) Methyl 2-isopropyl-1-((2-(trimethylsilyl)ethoxy)methyl)-1H-imidazole-4-carboxylate Into a flask containing a solution of methyl 2-isopropyl-1H-imidazole-4-carboxylate (2.7 g, 16.1 mmol) in DMF (20 ml), K$_2$CO$_3$ (5.5 g, 40.2 mmol) and SEM-Cl (3.5 g, 21.0 mmol) were added. The resulting mixture was heated at 80° C. for 18 h. The reaction mixture was diluted with H$_2$O and extracted with EtOAc. The product was purified with flash chromatography. Yield 830 mg. $^1$H-NMR (400 MHz; CDCl$_3$): δ 0.04 (s, 9H), 0.85-0.89 (m, 2H), 1.28 (d, 6H), 3.15-3.20 (m, 1H), 3.57 (t, 2H), 3.83 (s, 3H), 5.74 (s, 2H), 7.69 (s, 1H).

c) 2-Isopropyl-1-((2-(trimethylsilyl)ethoxy)methyl)-1H-imidazole-4-carboxylic acid The title compound was prepared using the procedure described in Example 32(d) starting from methyl 2-isopropyl-1-((2-(trimethylsilyl)ethoxy)methyl)-1H-imidazole-4-carboxylate (830 mg, 27.8 mmol). The product was triturated from ether and pentane. Yield 430 mg. $^1$H-NMR (400 MHz; DMSO-$d_6$): δ 0.04 (s, 9H), 0.83 (t, 2H), 1.21 (s, 6H), 3.10-3.16 (m, 1H), 3.41-3.50 (m, 2H), 5.34 (s, 2H), 5.35 (s, 1H), 7.85 (s, 1H).

d) (S)—N-(1-(3-(3-Chloro-4-cyanophenyl)-1H-pyrazol-1-yl)propan-2-yl)-2-isopropyl-1-((2-(trimethylsilyl)ethoxy)methyl)-1H-imidazole-4-carboxamide The title compound was prepared using the procedure described in Example 32(e) starting from 2-isopropyl-1-((2-(trimethylsilyl)ethoxy)methyl)-1H-imidazole-4-carboxylic acid (0.430 g, 1.5 mmol) and (S)-4-(1-(2-aminopropyl)-1H-pyrazol-3-yl)-2-chlorobenzonitrile (0.395 g, 1.5 mmol). Yield 360 mg. $^1$H-NMR (400 MHz; DMSO-$d_6$): δ 0.06 (s, 9H), 0.80-0.85 (m, 2H), 1.10 (d, 3H), 1.21-1.24 (m, 6H), 3.08-3.15 (m, 1H), 3.43-3.47 (m, 2H), 4.30-4.44 (m, 3H), 5.32 (s, 2H), 6.96 (d, 1H), 7.63 (s, 1H), 7.85-7.87 (m, 2H), 7.93-7.95 (m, 2H), 8.09 (s, 1H).

e) (S)—N-(1-(3-(3-Chloro-4-cyanophenyl)-1H-pyrazol-1-yl)propan-2-yl)-2-isopropyl-1H-imidazole-4-carboxamide The title compound was prepared using the procedure described in Example 52(h) starting from (S)—N-(1-(3-(3-chloro-4-cyanophenyl)-1H-pyrazol-1-yl)propan-2-yl)-2-isopropyl-1-((2-(trimethylsilyl)-ethoxy)methyl)-1H-imidazole-4-carboxamide (0.36 g, 0.6 mmol). Yield 127 mg. $^1$H-NMR (400 MHz; DMSO-$d_6$): δ 1.08 (t, 3H), 1.23 (d, 6H), 2.94-3.01 (m, 1H), 4.27-4.44 (m, 3H), 6.96 (bs, 1H), 7.44 (s, 1H), 7.84 (s, 1H), 7.90-8.02 (m, 3H), 8.10 (s, 1H).

Example 56

(S)-2-Butyl-N-(1-(3-(3-chloro-4-cyanophenyl)-1H-pyrazol-1-yl)propan-2-yl)-1-methyl-1H-imidazole-4-carboxamide a) Methyl 2-butyl-1H-imidazole-4-carboxylate

The title compound was prepared using the procedure described in Example 55(a) starting from methyl 1H-imidazole-4-carboxylate (5 g, 39.7 mmol) and n-valeric acid (13 ml, 119 mmol). Yield: 1.2 g. $^1$H-NMR (400 MHz; CDCl$_3$): δ 0.92 (t, 3H), 1.24-1.29 (m, 2H), 1.68-1.76 (m, 2H), 2.76 (t, 2H), 3.87 (s, 3H), 7.62 (s, 1H), 9.92 (bs, 1H).

b) Methyl 2-butyl-1-methyl-1H-imidazole-4-carboxylate

Into flask containing a solution of methyl 2-butyl-1H-imidazole-4-carboxylate (1.2 g, 6.6 mmol) in acetone (40 ml), Cs$_2$CO$_3$ (6.5 g, 19.8 mmol) and methyl iodide (0.5 ml, 6.6 mmol) were added. The reaction mixture was stirred at RT for 4 h and the solvent was evaporated. The residue was diluted with water and extracted with EtOAc. The organic layer was concentrated and purified with flash chromatography. Yield 500 mg. $^1$H-NMR (400 MHz; CDCl$_3$): δ 0.937 (t, 3H), 1.35-1.44 (m, 2H), 1.68-1.75 (m, 2H), 2.69 (t, 2H), 3.62 (s, 3H), 3.86 (s, 3H), 7.50 (s, 1H).

c) (S)-2-Butyl-N-(1-(3-(3-chloro-4-cyanophenyl)-1H-pyrazol-1-yl)propan-2-yl)-1-methyl-1H-imidazole-4-carboxamide The title compound was prepared using the procedure described in Example 52(g) starting from (S)-4-(1-(2-aminopropyl)-1H-pyrazol-3-yl)-2-chlorobenzo-nitrile (664 mg, 2.55 mmol) and methyl 2-butyl-1-methyl-1H-imidazole-4-carboxylate (500 mg, 2.55 mmol). The product was purified with flash chromatography. Yield 291 mg. $^1$H-NMR (400 MHz; DMSO-d$_6$): δ 0.88 (t, 3H), 1.09 (t, 3H), 1.28-1.36 (m, 2H), 1.54-1.61 (m, 2H), 2.62 (t, 2H), 3.57 (s, 3H), 4.26-4.39 (m, 3H), 6.95 (bs, 1H), 7.47 (s, 1H), 7.82 (d, 1H), 7.90 (d, 1H), 7.96 (s, 2H), 8.09 (s, 1H).

Example 57

(S)—N-(1-(3-(3-Chloro-4-cyanophenyl)-1H-pyrazol-1-yl)propan-2-yl)-2-(2-hydroxypropan-2-yl)-1-methyl-1H-imidazole-4-carboxamide a) Methyl 2-(2-hydroxypropan-2-yl)-1-methyl-1H-imidazole-4-carboxylate The title compound was prepared using the procedure described in Example 2(d) starting from methyl 2-acetyl-1-methyl-1H-imidazole-4-carboxylate (400 mg, 2.19 mmol). The product was purified with flash-chromatography. Yield 255 mg. $^1$H-NMR (400 MHz; DMSO-d$_6$): δ 1.51 (s, 6H), 3.70 (s, 3H), 3.83 (s, 3H), 5.40 (s, 1H), 7.81 (s, 1H).

b) (S)—N-(1-(3-(3-Chloro-4-cyanophenyl)-1H-pyrazol-1-yl)propan-2-yl)-2-(2-hydroxypropan-2-yl)-1-methyl-1H-imidazole-4-carboxamide The title compound was prepared using the procedure described in Example 52(g) starting from methyl 2-(2-hydroxypropan-2-yl)-1-methyl-1H-imidazole-4-carboxylate (200 mg, 1 mmol) and (S)-4-(1-(2-aminopropyl)-1H-pyrazol-3-yl)-2-(trifluoromethyl)benzonitrile (264 mg, 1 mmol). Yield 140 mg. $^1$H-NMR (400 MHz; DMSO-d$_6$): δ 1.08 (d, 3H), 1.50 (s, 6H), 3.80 (s, 3H), 4.28-4.41 (m, 3H), 5.36 (s, 1H), 6.97 (d, 1H), 7.51 (s, 1H), 7.73 (d, 1H), 7.84 (d, 1H), 7.96 (s, 2H), 8.10 (d, 1H).

Example 58

(S)—N-(1-(3-(3-Chloro-4-cyanophenyl)-1H-pyrazol-1-yl)propan-2-yl)-1-methyl-2-(1-methyl-1H-pyrazol-4-yl)-1H-imidazole-4-carboxamide a) Benzyl-2-bromo-1-((2-(trimethylsilyl)ethoxy)methyl)-1H-imidazole-4-carboxylate Silver oxide (12.7 g, 54.8 mmol) was added to a solution of 2-bromo-1-((2-(trimethyl-silyl)ethoxy)methyl)-1H-imidazole-4-carboxylic acid (11.7 g, 36.5 mmol) in ACN (200 ml) and stirred at RT for 10 min. Benzyl bromide (4.2 ml, 36.5 mmol) was added to the mixture and stirred at RT for 12 h. The reaction mixture was filtered through a celite bed and the filtrate was concentrated under reduced pressure. The product was purified by flash chromatography. Yield 10 g. $^1$H-NMR (400 MHz; CDCl$_3$): δ −0.04 (s, 9H), 0.92 (t, 2H), 3.54 (t, 2H), 5.29 (s, 2H), 5.35 (s, 2H), 7.30-7.44 (m, 5H), 7.76 (s, 1H).

b) Benzyl 2-bromo-1H-imidazole-4-carboxylate hydrochloride

The title compound was prepared using the procedure described in Example 52(h) starting from benzyl-2-bromo-1-((2-(trimethylsilyl)ethoxy)methyl)-1H-imidazole-4-carboxylate (16.2 g, 39.5 mmol). Yield 9.0 g. LC-MS: [M+1]= 281.

c) Benzyl 2-bromo-1-methyl-1H-imidazole-4-carboxylate

The title compound was prepared using the procedure described in Example 56(b) starting from benzyl 2-bromo-1H-imidazole-4-carboxylate hydrochloride (8.3 g, 29.4 mmol). The product was purified by flash chromatography. Yield 1.6 g. $^1$H-NMR (400 MHz; CDCl$_3$): δ 3.66 (s, 3H), 5.33 (s, 2H), 7.26-7.43 (m, 5H), 7.63 (s, 1H).

d) Benzyl 1-methyl-2-(1-methyl-1H-pyrazol-4-yl)-1H-imidazole-4-carboxylate

Into a flask containing a solution of benzyl 2-bromo-1-methyl-1H-imidazole-4-carboxylate (2 g, 6.77 mmol) in 1,2-dimethoxyethane (40 ml), potassium phosphate (2.3 g, 20.3 mmol) and 1-methyl-4-(4,4,5,5-tetramethyl-1,3,2-dioxaborolan-2-yl)-1H-pyrazole (1.41 g, 6.77 mmol) were added at RT under argon atmosphere. The resulting mixture was degassed and purged with argon for 10 minutes. Then Pd(PPh$_3$)$_4$ (0.310 g, 0.2 mmol) was added to the reaction mixture and heated at 90° C. for 12 h. The reaction mixture was filtered through a celite bed and the filtrate was diluted with water and extracted with EtOAc. The organic layer was concentrated and purified by flash chromatography. Yield 1.1 g. $^1$H-NMR (400 MHz; CDCl$_3$): δ 3.77 (s, 3H), 3.95 (s, 3H), 5.36 (s, 2H), 7.30-7.37 (m, 3H), 7.45 (d, 2H), 7.59 (s, 1H), 7.79 (s, 1H), 7.89 (s, 1H).

e) 1-Methyl-2-(1-methyl-1H-pyrazol-4-yl)-1H-imidazole-4-carboxylic acid

Into a flask containing a solution of benzyl 1-methyl-2-(1-methyl-1H-pyrazol-4-yl)-1H-imidazole-4-carboxylate (1 g, 3.4 mmol) in EtOH (25 ml), 10% Pd/C (100 mg) was added at RT. The resulting mixture was stirred at RT under H$_2$ atmosphere for 3 h. The reaction mixture was filtered through a f) (S)—N-(1-(3-(3-Chloro-4-cyanophenyl)-1H-pyrazol-1-yl)propan-2-yl)-1-methyl-2-(1-methyl-1H-pyrazol-4-yl)-1H-imidazole-4-carboxamide The title compound was prepared using the procedure described in Example 32(e) starting from 1-methyl-2-(1-methyl-1H-pyrazol-4-yl)-1H-imidazole-4-carboxylic acid (0.3 g, 1.44 mmol) and (S)-4-(1-(2-aminopropyl)-1H-pyrazol-3-yl)-2-chlorobenzonitrile (0.377 g, 1.44 mmol). The product was purified by flash chromatography. Yield 200 mg. $^1$H-NMR (400 MHz; DMSO-d$_6$): δ 1.10 (d, 3H), 3.72 (s, 3H), 3.91 (s, 3H), 4.23-4.45 (m, 3H), 6.95 (d, 1H), 7.63 (d, 1H), 7.83 (t, 2H), 7.99 (d, 1H), 8.03 (d, 1H), 8.07 (s, 1H), 8.17 (s, 1H).

Example 59

(S)—N-(1-(3-(3-Chloro-4-cyanophenyl)-1H-pyrazol-1-yl)propan-2-yl)-2-cyclopropyl-1-methyl-1H-imidazole-4-carboxamide a) Benzyl 2-cyclopropyl-1-methyl-1H-imidazole-4-carboxylate Into a solution of benzyl 2-bromo-1-methyl-1H-imidazole-4-carboxylate (2.8 g, 9.49 mmol) in THF (40 ml) and water (20 ml), cesium carbonate (7.71 g, 23.7 mmol) and cyclopropyl boronic acid (1.22 g, 14.2 mmol) were added under argon atmosphere at RT. The resulting mixture was degassed and purged with argon for 10 min. Pd(PPh$_3$)$_2$Cl$_2$ (0.332 g, 0.04 mmol) was added to the mixture and heated at 100° C. for 12 h. The reaction mixture was filtered through a celite bed and the filtrate was diluted with water and extracted with EtOAc. The organic layer was concentrated and purified by flash chromatography. Yield 1.1 g. $^1$H-NMR (400 MHz; CDCl$_3$): δ 0.95-1.02 (m, 2H), 1.07-1.11 (m, 2H), 1.72-1.78 (m, 1H), 3.70 (s, 3H), 5.32 (s, 2H), 7.29 (s, 1H), 7.42-7.62 (m, 5H), LC-MS: [M+1]=257.

b) 2-Cyclopropyl-1-methyl-1H-imidazole-4-carboxylic acid

The title compound was prepared using the procedure described in Example 58(e) starting from benzyl 2-cyclopropyl-1-methyl-1H-imidazole-4-carboxylate (1.1 g, 1.95 mmol). Yield 400 mg. LC-MS: [M+1]=167.06.

c) (S)—N-(1-(3-(3-Chloro-4-cyanophenyl)-1H-pyrazol-1-yl)propan-2-yl)-2-cyclopropyl-1-methyl-1H-imidazole-4-carboxamide The title compound was prepared using the procedure described in Example 32(e) starting from 2-cyclopropyl-1-methyl-1H-imidazole-4-carboxylic acid (0.160 g, 0.96 mmol) and (S)-4-(1-(2-aminopropyl)-1H-pyrazol-3-yl)-2-chloro benzonitrile (0.251 g, 0.96 mmol). The product was purified with flash chromatography. Yield 166 mg. $^1$H-NMR (400 MHz; DMSO-d$_6$): δ 0.80-0.92 (m, 4H), 1.07 (d, 3H), 1.94-1.98 (m, 1H), 3.65 (s, 3H), 4.26-4.38 (m, 3H), 6.95 (s, 1H), 7.47 (s, 1H), 7.75 (d, 1H), 7.81 (s, 1H); 7.96 (s, 2H), 8.08 (s, 1H). LC-MS: [M+1]=409.28.

Example 60

(S)—N$^4$-(1-(3-(3-Chloro-4-cyanophenyl)-1H-pyrazol-1-yl)propan-2-yl)-1H-imidazole-2,4-dicarboxamide a) (S)—N$^4$-(1-(3-(3-Chloro-4-cyanophenyl)-1H-pyrazol-1-yl)propan-2-yl)-1-((2-(trimethylsilyl)ethoxy)methyl)-1H-imidazole-2,4-dicarboxamide The title compound was prepared using the procedure described in Example 32(e) starting from 2-carbamoyl-1-((2-(trimethylsilyl)ethoxy)methyl)-1H-imidazole-4-carboxylic acid (400 mg, 1.4 mmol) and (S)-4-(1-(2-aminopropyl)-1H-pyrazol-3-yl)-2-chlorobenzonitrile (366 mg, 1.4 mmol). The product was purified with flash-chromatography. Yield 410 mg. LC-MS: [M+1]=528.24.

b) (S)—N$^4$-(1-(3-(3-Chloro-4-cyanophenyl)-1H-pyrazol-1-yl)propan-2-yl)-1H-imidazole-2,4-dicarboxamide The title compound was prepared using the procedure described in Example 52(g) starting from (S)—N$^4$-(1-(3-(3-chloro-4-cyano-phenyl)-1H-pyrazol-1-yl)propan-2-yl)-1-((2-(trimethylsilyl)ethoxy)methyl)-1H-imidazole-2,4-dicarboxamide (0.41 g, 0.77 mmol). Yield 310 mg. $^1$H-NMR (400 MHz; DMSO-d$_6$): δ 1.13 (d, 3H), 4.32-4.50 (m, 3H), 6.96 (s, 1H), 7.64 (s, 2H), 7.72 (s, 1H), 7.85 (s, 1H), 7.93-7.98 (m, 3H), 8.06 (s, 1H), 13.40 (s, 1H).

Example 61

(S)—N-(1-(3-(4-Cyano-3-(trifluoromethyl)phenyl)-1H-pyrazol-1-yl)propan-2-yl)-2-(2-hydroxypropan-2-yl)oxazole-4-carboxamide The title compound was prepared using the procedure described in Example 32(e) starting from 2-(2-hydroxypropan-2-yl)-oxazole-4-carboxylic acid (0.3 g, 1.75 mmol) and (S)-4-(1-(2-aminopropyl)-1H-pyrazol-3-yl)-2-(trifluoromethyl)benzonitrile (0.516 mg, 1.75 mmol). The product was purified by column chromatography. Yield 270 mg. $^1$H-NMR (400 MHz; DMSO-d6): δ 1.13 (d, 3H), 1.51 (s, 6H), 4.30-4.52 (m, 3H), 5.67 (s, 1H), 7.05 (s, 1H), 7.86 (d, 1H), 8.17 (d, 2H), 8.28 (d, 2H), 8.47 (s, 1H).

Example 62

(S)—N-(2-(3-(3-Chloro-4-cyano-5-fluorophenyl)-1H-pyrazol-1-yl)propyl)-2-(2-hydroxypropan-2-yl)oxazole-4-carboxamide a) (S)-4-(1-(1-Aminopropan-2-yl)-1H-pyrazol-3-yl)-2-chloro-6-fluoro-benzonitrile The title compound was prepared using the procedure described in Example 3(g) starting from 2-chloro-6-fluoro-4-(1H-pyrazol-3-yl)benzonitrile (13.5 mmol, 3 g) and (R)-tert-butyl (2-hydroxypropyl)carbamate (27 mmol, 4.72 g). Yield 1.3 g. $^1$H-NMR (400 MHz; CDCl$_3$): δ 1.47 (d, 3H), 3.02-3.19 (m, 2H), 4.30-4.38 (m, 1H), 6.60 (d, 1H), 7.52-7.59 (m, 2H), 7.75 (s, 1H). LC-MS: [M+1]=279.17.

b) (S)—N-(2-(3-(3-Chloro-4-cyano-5-fluorophenyl)-1H-pyrazol-1-yl)propyl)-2-(2-hydroxypropan-2-yl)oxazole-4-carboxamide The title compound was prepared using the procedure described in Example 52(g) starting from ethyl 2-(2-hydroxypropan-2-yl)oxazole-4-carboxylate (0.75 mmol, 150 mg) and (S)-4-(1-(1-aminopropan-2-yl)-1H-pyrazol-3-yl)-2-chloro-6-fluorobenzonitrile (0.75 mmol, 209 mg). Yield 87 mg. $^1$H-NMR (400 MHz; DMSO-d$_6$): δ 1.45 (d, 3H), 1.49 (s, 6H), 3.55-3.61 (m, 1H), 3.66-3.73 (m, 1H), 4.69-4.74 (m, 1H), 5.66 (s, 1H), 7.03 (d, 1H), 7.88-7.93 (m, 2H), 8.0 (s, 1H), 8.19 (t, 1H), 8.51 (s, 1H). LC-MS: [M+1]=432.31.

Example 63

(R)—N-(2-(3-(3-Chloro-4-cyano-5-fluorophenyl)-1H-pyrazol-1-yl)propyl)-2-(2-hydroxypropan-2-yl) oxazole-4-carboxamide a) (R)-4-(1-(1-Aminopropan-2-yl)-1H-pyrazol-3-yl)-2-chloro-6-fluoro-benzonitrile The title compound was prepared using the procedure described in Example 3(g) starting from 2-chloro-6-fluoro-4-(1H-pyrazol-3-yl)benzonitrile (14.9 mmol, 3.3 g) and (S)-tert-butyl (2-hydroxypropyl)carbamate (29.8 mmol, 5.23 g). Yield 2.2 g. $^1$H-NMR (400 MHz; CDCl$_3$): δ 1.53 (d, 3H), 3.44-3.61 (m, 2H), 4.48-4.54 (m, 1H), 6.59 (d, 1H), 7.48 (d, 1H), 7.55 (d, 1H), 7.75 (s, 1H). LC-MS: [M+1]=279.12.

b) (R)—N-(2-(3-(3-Chloro-4-cyano-5-fluorophenyl)-1H-pyrazol-1-yl)propyl)-2-(2-hydroxypropan-2-yl) oxazole-4-carboxamide The title compound was prepared using the procedure described in Example 52(g) starting from ethyl 2-(2-hydroxypropan-2-yl)oxazole-4-carboxylate (0.5 mmol, 139 mg) and (R)-4-(1-(1-aminopropan-2-yl)-1H-pyrazol-3-yl)-2-chloro-6-fluoro-benzonitrile (0.5 mmol, 100 mg). Yield 27 mg. $^1$H-NMR (400 MHz; DMSO-d$_6$): δ 1.45 (d, 3H), 1.49 (s, 6H), 3.55-3.61 (m, 1H), 3.66-3.73 (m, 1H), 4.67-4.76 (m, 1H), 5.65 (s, 1H), 7.03 (d, 1H), 7.88 (d, 1H), 7.91 (d, 1H), 8.0 (s, 1H), 8.19 (t, 1H), 8.51 (s, 1H). LC-MS: [M+1]=432.02.

Example 64

(R)—N-(2-(3-(3-Chloro-4-cyano-5-fluorophenyl)-1H-pyrazol-1-yl)propyl)-2-(2-hydroxypropan-2-yl)-1H-imidazole-4-carboxamide a) (R)—N-(2-(3-(3-Chloro-4-cyano-5-fluorophenyl)-1H-pyrazol-1-yl)propyl)-2-(2-hydroxypropan-2-yl)-1-((2-(trimethylsilyl)ethoxy)methyl)-1H-imidazole-4-carboxamide The title compound was prepared using the procedure described in Example 32(e) starting from 2-(2-hydroxypropan-2-yl)-1-((2-(trimethylsilyl)ethoxy)methyl)-1H-imidazole-4-carboxylic acid (1.43 mmol, 430 mg) and (R)-4-(1-(1-aminopropan-2-yl)-1H-pyrazol-3-yl)-2-chloro-6-fluorobenzonitrile (1.43 mmol, 400 mg). The product was purified by flash-chromatography. Yield 410 mg. LC-MS: [M+1]=561.21.

b) (R)—N-(2-(3-(3-Chloro-4-cyano-5-fluorophenyl)-1H-pyrazol-1-yl)propyl)-2-(2-hydroxypropan-2-yl)-1H-imidazole-4-carboxamide The title compound was prepared using the procedure described in Example 52(h) starting from (R)—N-(2-(3-(3-chloro-4-cyano-5-fluorophenyl)-1H-pyrazol-1-yl)propyl)-2-(2-hydroxypropan-2-yl)-1-((2-(trimethylsilyl)ethoxy)methyl)-1H-imidazole-4-carboxamide (0.73 mmol, 410 mg). Yield 130 mg. $^1$H-NMR (400 MHz; DMSO-d$_6$): δ 1.42 (s, 6H), 1.44 (d, 3H), 3.56-3.69 (m, 2H), 4.67-4.71 (m, 1H), 5.31 (s, 1H), 7.04 (bs, 1H), 7.40 (bs, 1H), 7.76 (bs, 1H), 7.90 (d, 1H), 7.94 (s, 1H), 8.01 (s, 1H), 12.17 (s, 1H). LC-MS: [M+1]= 431.22.

Example 65

(S)—N-(1-(3-(3-Chloro-4-cyano-5-fluorophenyl)-1H-pyrazol-1-yl)propan-2-yl)-2-(2,2,2-trifluoroethyl)-1H-imidazole-4-carboxamide a) 3,3,3-Trifluoro-N'-hydroxypropanimidamide Into a flask containing sodium (45.87 mmol, 2.5 g) in MeOH (10 ml), a suspension of NH$_2$OH.HCl (45.87 mmol, 3.2 g) in MeOH (11 ml) was added using a dropping funnel. After addition, the mixture was stirred for 15 min. The suspension was filtered to remove the precipitated NaCl. The filtrate was cooled to 0° C. and 3,3,3-trifluoropropionitrile (45.87 mmol, 5 g) was added. The reaction mixture was stirred for 1 h. The solvent was evaporated under reduced pressure. The crude product was proceeded to the next step without purification. Yield 3.0 g.

b) Ethyl 3-(((1-amino-3,3,3-trifluoropropylidene) amino)oxy)acrylate

Into a flask containing 3,3,3-trifluoro-N'-hydroxypropanimidamide (21 mmol, 3 g) in ACN (50 ml), Et$_3$N (21 mmol, 3.5 ml) was added at RT. The resulting mixture was heated at 80° C. and a solution of ethyl propiolate (25.1 mmol, 2.5 g) in ACN (20 ml) was added. The reaction mixture was heated at 80° C. for overnight. The solvent was evaporated and the crude was purified by flash-chromatography. Yield 3.8 g. $^1$H-NMR (400 MHz; DMSO-d$_6$): δ 1.17 (t, 3H), 3.18 (q, 2H), 4.09 (q, 2H), 5.44 (d, 1H), 6.78 (bs, 2H), 7.70 (d, 1H). LC-MS: [M−1]=239.17.

c) Ethyl 2-(2,2,2-trifluoroethyl)-1H-imidazole-4-carboxylate

Ethyl 3-(((1-amino-3,3,3-trifluoropropylidene)amino) oxy)acrylate (4.17 mmol, 1 g) was dissolved in diphenyl ether (2 ml) and heated at 180° C. for 30 min. The reaction mixture was adsorbed on silica gel and purified by column-chromatography. Yield 120 mg. $^1$H-NMR (400 MHz; DMSO-d$_6$+ D$_2$O): δ 1.23 (t, 3H), 3.73 (q, 2H), 4.19 (q, 2H), 7.80 (s, 1H). LC-MS: [M+1]=223.14.

d) Ethyl 2-(2,2,2-trifluoroethyl)-1-((2-(trimethylsilyl)ethoxy)methyl)-1H-imidazole-4-carboxylate The title compound was prepared using the procedure described in Example 52(b) starting from ethyl 2-(2,2,2-trifluoroethyl)-1H-imidazole-4-carboxylate (3.6 mmol, 0.8 g) and SEM-Cl (4.3 mmol, 0.8 ml). Yield 602 mg. $^1$H-NMR (400 MHz; CDCl$_3$): δ 0.01 (s, 9H), 0.91 (t, 2H), 1.39 (t, 3H), 3.48 (t, 2H), 3.75 (q, 2H), 4.39 (q, 2H), 5.33 (s, 2H), 7.69 (s, 1H).

e) 2-(2,2,2-Trifluoroethyl)-1-((2-(trimethylsilyl) ethoxy)methyl)-1H-imidazole-4-carboxylic acid Ethyl 2-(2,2,2-trifluoroethyl)-1-((2-(trimethylsilyl) ethoxy)methyl)-1H-imidazole-4-carboxylate (2.41 mmol, 850 mg) was dissolved in THF (30 ml) and H$_2$O (20 ml).

NaOH (4.82 mmol, 200 mg) was added and the mixture was stirred at RT for 48 h. The reaction mixture was concentrated and acidified to pH 2 using 1 N HCl. The mixture was extracted with DCM and the organic layer was concentrated. Yield 310 mg. LC-MS: [M+1]=325.01.

f) (S)—N-(1-(3-(3-Chloro-4-cyano-5-fluorophenyl)-1H-pyrazol-1-yl)propan-2-yl)-2-(2,2,2-trifluoroethyl)-1-((2-(trimethylsilyl)ethoxy)methyl)-1H-imidazole-4-carboxamide The title compound was prepared using the procedure described in Example 32(e) starting from 2-(2,2,2-trifluoroethyl)-1-((2-(trimethylsilyl)ethoxy)methyl)-1H-imidazole-4-carboxylic acid (0.98 mmol, 320 mg) and (S)-4-(1-(2-aminopropyl)-1H-pyrazol-3-yl)-2-chloro-6-fluorobenzonitrile (0.98 mmol, 273 mg). The product was purified by flash-chromatography. Yield 310 mg. LC-MS: [M+1]=585.25.

g) (S)—N-(1-(3-(3-Chloro-4-cyano-5-fluorophenyl)-1H-pyrazol-1-yl)propan-2-yl)-2-(2,2,2-trifluoroethyl)-1H-imidazole-4-carboxamide The title compound was prepared using the procedure described in Example 52(h) starting from (S)—N-(1-(3-(3-chloro-4-cyano-5-fluorophenyl)-1H-pyrazol-1-yl)propan-2-yl)-2-(2,2,2-trifluoroethyl)-1-((2-(trimethylsilyl)ethoxy)methyl)-1H-imidazole-4-carboxamide (0.74 mmol, 430 mg). Yield 220 mg. $^1$H-NMR (400 MHz; DMSO-$d_6$): δ 1.07 (d, 3H), 3.73 (q, 2H), 4.24-4.47 (m, 3H), 7.03 (s, 1H), 7.61 (s, 1H), 7.80-7.98 (m, 2H), 8.0 (s, 1H), 8.10 (d, 1H), 12.64 (s, 1H). LC-MS: [M+1]=455.12.

Example 66

(S)—N-(1-(3-(3-Chloro-4-cyano-5-fluorophenyl)-1H-pyrazol-1-yl)propan-2-yl)-2-(trifluoromethyl)-1H-imidazole-4-carboxamide a) 2,2,2-Trifluoro-N'-hydroxyacetimidamide The title compound was prepared using the procedure described in Example 65(a) starting from 2,2,2-trifluoroacetonitrile (558 mmol, 53 g) and NH$_2$OH.HCl (558 mmol, 39 g). The crude product was used directly for the next step. Yield 70 g.

b) Ethyl 3-(((1-amino-2,2,2-trifluoroethylidene)amino)oxy)acrylate

The title compound was prepared using the procedure described in Example 65(b) starting from 2,2,2-trifluoro-N'-hydroxyacetimidamide (218.7 mmol, 28 g) and ethyl propiolate (262.5 mmol, 25.7 g). Yield 45.2 g. $^1$H-NMR (400 MHz; DMSO-$d_6$): δ 1.32 (t, 3H), 4.31 (q, 2H), 7.03 (d, 1H), 7.60 (bs, 2H), 8.29 (d, 1H). LC-MS: [M−1]=225.34.

c) Ethyl 2-(trifluoromethyl)-1H-imidazole-4-carboxylate

The title compound was prepared using the procedure described in Example 65(c) starting from ethyl 3-(((1-amino-2,2,2-trifluoroethylidene)amino)oxy)acrylate (4.42 mmol, 1 g). Yield 177 mg. $^1$H-NMR (400 MHz; DMSO-$d_6$): δ 1.28 (t, 3H), 4.27 (q, 2H), 8.16 (s, 1H), 14.27 (bs, 1H). LC-MS: [M+1]=209.32.

d) Ethyl 2-(trifluoromethyl)-1-((2-(trimethylsilyl)ethoxy)methyl)-1H-imidazole-4-carboxylate The title compound was prepared using the procedure described in Example 52(b) starting from ethyl 2-(trifluoromethyl)-1H-imidazole-4-carboxylate (9.5 mmol, 2 g) and SEM-Cl (11.5 mmol, 2.1 ml). Yield 1.9 g. $^1$H-NMR (400 MHz; CDCl$_3$): δ −0.01 (s, 9H), 0.91 (t, 2H), 1.40 (t, 3H), 3.54 (t, 2H), 4.40 (q, 2H), 5.43 (s, 2H), 7.85 (s, 1H).

e) 2-(Trifluoromethyl)-1-((2-(trimethylsilyl)ethoxy)methyl)-1H-imidazole-4-carboxylic acid The title compound was prepared using the procedure described in Example 32(d) starting from ethyl 2-(trifluoromethyl)-1-((2-(trimethylsilyl)ethoxy)methyl)-1H-imidazole-4-carboxylate (2.06 mmol, 700 mg). Yield 601 mg. $^1$H-NMR (400 MHz; DMSO-$d_6$): δ −0.07 (s, 9H), 0.82 (t, 2H), 3.54 (t, 2H), 5.85 (s, 2H), 7.78 (s, 1H). LC-MS: [M+1]=311.07.

f) (S)—N-(1-(3-(3-Chloro-4-cyano-5-fluorophenyl)-1H-pyrazol-1-yl)propan-2-yl)-2-(trifluoromethyl)-1-((2-(trimethylsilyl)ethoxy)methyl)-1H-imidazole-4-carboxamide The title compound was prepared using the procedure described in Example 32(e) starting from 2-(trifluoromethyl)-1-((2-(trimethylsilyl)ethoxy)methyl)-1H-imidazole-4-carboxylic acid (0.97 mmol, 300 mg) and (S)-4-(1-(2-aminopropyl)-1H-pyrazol-3-yl)-2-chloro-6-fluorobenzonitrile (0.97 mmol, 269 mg). The product was purified by flash-chromatography. Yield 230 mg. $^1$H-NMR (400 MHz; DMSO-$d_6$): δ −0.13 (s, 9H), 0.65-0.77 (m, 2H), 1.17 (d, 3H), 3.36-3.43 (m, 2H), 4.21-4.42 (m, 3H), 5.75 (q, 2H), 7.01 (s, 1H), 7.64 (s, 1H), 7.83-7.88 (m, 2H), 7.95 (s, 1H), 8.65 (d, 1H). LC-MS: [M+1]=571.01.

g) (S)—N-(1-(3-(3-Chloro-4-cyano-5-fluorophenyl)-1H-pyrazol-1-yl)propan-2-yl)-2-(trifluoromethyl)-1H-imidazole-4-carboxamide The title compound was prepared using the procedure described in Example 52(h) starting from (S)—N-(1-(3-(3-chloro-4-cyano-5-fluorophenyl)-1H-pyrazol-1-yl)propan-2-yl)-2-(trifluoromethyl)-1-((2-(trimethylsilyl)ethoxy)methyl)-1H-imidazole-4-carboxamide (0.39 mmol, 220 mg). Yield 153 mg. $^1$H-NMR (400 MHz; DMSO-$d_6$): δ 1.12 (d, 3H), 4.28-4.49 (m, 3H), 7.01 (d, 1H), 7.82-7.87 (m, 3H), 7.95 (s, 1H), 8.23 (d, 1H), 14.08 (s, 1H). LC-MS: [M+1]=441.17.

Example 67

N—((S)-1-(3-(3-Chloro-4-cyano-5-fluorophenyl)-1H-pyrazol-1-yl)propan-2-yl)-3-((S)-1-hydroxyethyl)-1,2,4-oxadiazole-5-carboxamide and N—((S)-1-(3-(3-chloro-4-cyano-5-fluorophenyl)-1H-pyrazol-1-yl)propan-2-yl)-3-((R)-1-hydroxyethyl)-1,2,4-oxadiazole-5-carboxamide a) 2-((tert-Butyldiphenylsilyl)oxy)propanenitrile Into a flask containing DL-lactonitrile (36.3 mmol, 2.8 g) in DCM (25 ml), Et$_3$N (54.7 mmol, 8.1 ml) and tert-butyldiphenylsilyl chloride (36.3 mmol, 10 g) were added. The resulting solution was stirred at RT for 24 h. The reaction mixture was quenched with H$_2$O and extracted with DCM.

The organic layer was washed with brine, dried, filtered and evaporated. The crude product was purified by flash-chromatography. Yield 4.52 g. $^1$H-NMR (400 MHz; CDCl$_3$): δ 1.10 (s, 9H), 1.50 (d, 3H), 4.43 (q, 1H), 7.39-7.51 (m, 6H), 7.65 (d, 2H), 7.71 (d, 2H).

b) 2-((tert-Butyldiphenylsilyl)oxy)-N'-hydroxypropanimidamide

Into a flask containing 2-((tert-butyldiphenylsilyl)oxy)propanenitrile (14.6 mmol, 4.5 g) in MeOH (50 ml), NH$_2$OH.HCl (29.1 mmol, 2 g) and NaHCO$_3$ (43.7 mmol, 3.6 g) were added. The resulting mixture was stirred at 70° C. for overnight. The mixture was quenched with H$_2$O and extracted with EtOAc. The organic layer was washed with H$_2$O, dried, filtered and evaporated. Yield 4.02 g. $^1$H-NMR (400 MHz; DMSO-d$_6$): δ 1.01 (s, 9H), 1.20 (d, 3H), 4.12 (q, 1H), 7.38-7.46 (m, 6H), 7.60-7.64 (m, 4H). LC-MS: [M+1]=343.12.

c) Ethyl 3-(1-((tert-butyldiphenylsilyl)oxy)ethyl)-1,2,4-oxadiazole-5-carboxylate The title compound was prepared using the procedure described in Example 5(a) starting from 2-((tert-butyldiphenylsilyl)oxy)-N'-hydroxypropanimidamide (3.24 mmol, 1 g). Yield 618 mg. $^1$H-NMR (400 MHz; CDCl$_3$): δ 1.07 (s, 9H), 1.46 (t, 3H), 1.52 (d, 3H), 4.53 (q, 2H), 5.09 (q, 1H), 7.30-7.47 (m, 6H), 7.61 (d, 2H), 7.69 (d, 2H).

d) Ethyl 3-(1-hydroxyethyl)-1,2,4-oxadiazole-5-carboxylate

Ethyl 3-(1-((tert-butyldiphenylsilyl)oxy)ethyl)-1,2,4-oxadiazole-5-carboxylate (5.90 mmol, 2.5 g) was dissolved in THF and cooled to 0° C. with an ice bath. 70% Hydrogen fluoride in pyridine (1.5 ml) was added slowly. After addition, the reaction mixture was stirred at ambient temperature for overnight. The reaction mixture was basified by aqueous NaHCO$_3$ solution and extracted with DCM. The organic layers were washed with water, dried, filtered and evaporated. The product was purified by flash-chromatography. Yield 897 mg. $^1$H-NMR (400 MHz; CDCl$_3$): δ 1.46 (t, 3H), 1.66 (d, 3H), 4.53 (q, 2H), 5.11 (q, 1H).

e) N—((S)-1-(3-(3-Chloro-4-cyano-5-fluorophenyl)-1H-pyrazol-1-yl)propan-2-yl)-3-((S)-1-hydroxyethyl)-1,2,4-oxadiazole-5-carboxamide (Diastereomer 1) and N—((S)-1-(3-(3-chloro-4-cyano-5-fluorophenyl)-1H-pyrazol-1-yl)propan-2-yl)-3-((R)-1-hydroxyethyl)-1,2,4-oxadiazole-5-carboxamide (Diastereomer 2)

The title compounds were prepared using the procedure described in Example 52(g) starting from ethyl 3-(1-hydroxyethyl)-1,2,4-oxadiazole-5-carboxylate (9.67 mmol, 1.8 g) and (S)-4-(1-(2-aminopropyl)-1H-pyrazol-3-yl)-2-chloro-6-fluorobenzonitrile (9.67 mmol, 2.62 g). Yield 1.02 g (mixture of diastereomers). The reaction produced the diastereomeric mixture of N—((S)-1-(3-(3-chloro-4-cyano-5-fluorophenyl)-1H-pyrazol-1-yl)propan-2-yl)-3-((S)-1-hydroxyethyl)-1,2,4-oxadiazole-5-carboxamide and N—((S)-1-(3-(3-chloro-4-cyano-5-fluorophenyl)-1H-pyrazol-1-yl)propan-2-yl)-3-((R)-1-hydroxyethyl)-1,2,4-oxadiazole-5-carboxamide. Both diastereomers were separated by column-chromatography.

Diastereomer 1: $^1$H-NMR (400 MHz; DMSO-d$_6$): δ 1.19 (d, 3H), 1.44 (d, 3H), 4.34 (d, 2H), 4.43-4.51 (m, 1H), 4.91 (q, 1H), 5.84 (d, 1H), 7.02 (d, 1H), 7.84-7.87 (m, 2H), 7.96 (s, 1H), 9.46 (d, 1H). LC-MS: [M+1]=419.12.

Diastereomer 2: $^1$H-NMR (400 MHz; DMSO-d$_6$): δ 1.18 (d, 3H), 1.44 (d, 3H), 4.34 (d, 2H), 4.43-4.50 (m, 1H), 4.91 (q, 1H), 5.84 (d, 1H), 7.02 (d, 1H), 7.80-7.90 (m, 2H), 7.96 (s, 1H), 9.46 (d, 1H). LC-MS: [M+1]=419.07.

Example 68

(S)—N-(2-(3-(3-Chloro-4-cyano-5-fluorophenyl)-1H-pyrazol-1-yl)propyl)-3-(2-hydroxypropan-2-yl)-1,2,4-oxadiazole-5-carboxamide a) Ethyl 3-acetyl-1,2,4-oxadiazole-5-carboxylate Into a flask containing ethyl 3-(1-hydroxyethyl)-1,2,4-oxadiazole-5-carboxylate (53.7 mmol, 10 g) in DCM (100 ml), Dess-Martin periodinane (80 mmol, 34.2 g) was added at 0° C. in portions and the resulting mixture was stirred at RT for 16 h. The reaction mixture was quenched with aqueous NaHCO$_3$ solution and extracted with DCM. The organic layers were dried, filtered and evaporated. The product was purified by flash-chromatography. Yield 9.12 g. $^1$H-NMR (400 MHz; CDCl$_3$): δ 1.47 (t, 3H), 2.76 (s, 3H), 4.58 (q, 2H).

b) Ethyl 3-(2-hydroxypropan-2-yl)-1,2,4-oxadiazole-5-carboxylate

The title compound was prepared using the procedure described in Example 2(d) starting from ethyl 3-acetyl-1,2,4-oxadiazole-5-carboxylate (10.8 mmol, 2 g). Yield 304 mg. $^1$H-NMR (400 MHz; CDCl$_3$): δ 1.39 (t, 3H), 1.59 (s, 6H), 4.54 (q, 2H). LC-MS: [M+1]=201.04.

c) (S)—N-(2-(3-(3-Chloro-4-cyano-5-fluorophenyl)-1H-pyrazol-1-yl)propyl)-3-(2-hydroxypropan-2-yl)-1,2,4-oxadiazole-5-carboxamide The title compound was prepared using the procedure described in Example 52(g) starting from ethyl 3-(2-hydroxypropan-2-yl)-1,2,4-oxadiazole-5-carboxylate (1.5 mmol, 300 mg) and (S)-4-(1-(1-aminopropan-2-yl)-1H-pyrazol-3-yl)-2-chloro-6-fluorobenzonitrile (1.5 mmol, 417 mg). Yield 160 mg. $^1$H-NMR (400 MHz; DMSO-d$_6$): δ 1.49 (bs, 9H), 3.57-3.64 (m, 1H), 3.68-3.76 (m, 1H), 4.69-4.75 (m, 1H), 5.69 (s, 1H), 7.02 (d, 1H), 7.89 (d, 1H), 7.94 (d, 1H), 7.99 (s, 1H), 9.46 (t, 1H). LC-MS: [M+1]=433.17.

Example 69

(S)—N-(1-(3-(3-Chloro-4-cyano-5-fluorophenyl)-1H-pyrazol-1-yl)propan-2-yl)-3-(2-hydroxypropan-2-yl)-1,2,4-oxadiazole-5-carboxamide The title compound was prepared using the procedure described in Example 52(g) starting from ethyl 3-(2-hydroxypropan-2-yl)-1,2,4-oxadiazole-5-carboxylate (2 mmol, 400 mg) and (S)-4-(1-(2-aminopropyl)-1H-pyrazol-3-yl)-2-chloro-6-fluoro-benzonitrile (2 mmol, 556 mg). Yield 202 mg. $^1$H-NMR (400 MHz; DMSO-d$_6$): δ 1.12 (d, 3H), 1.51 (bs, 6H), 4.34-4.37 (m, 2H), 4.43-4.51 (m, 1H), 5.70 (s, 1H), 7.02 (d, 1H), 7.83-7.88 (m, 2H), 7.96 (s, 1H), 9.41 (d, 1H). LC-MS: [M+1]=433.20.

Example 70

(S)—N-(1-(3-(3-Chloro-4-cyano-5-fluorophenyl)-1H-pyrazol-1-yl)propan-2-yl)-2-cyclopropyl-1H-imidazole-4-carboxamide a) Benzyl 2-cyclopropyl-1-((2-(trimethylsilyl)ethoxy)methyl)-1H-imidazole-4-carboxylate The title compound was prepared using the procedure described in Example 59(a) starting from benzyl 2-bromo-1-((2-(trimethylsilyl)ethoxy)methyl)-1H-imidazole-4-carboxylate (7.31 mmol, 3 g) and cyclopropylboronic acid (14.63 mmol, 1.25 g). Yield 1.02 g. $^1$H-NMR (400 MHz; CDCl$_3$): δ −0.02 (s, 9H), 0.91 (t, 2H), 0.99 (bs, 2H), 1.15 (bs, 2H), 1.87-1.94 (m, 1H), 3.52 (t, 2H), 5.32 (s, 2H), 5.34 (s, 2H), 7.29-7.43 (m, 5H), 7.59 (s, 1H). LC-MS: [M+1]=373.31.

b) 2-Cyclopropyl-1-((2-(trimethylsilyl)ethoxy)methyl)-1H-imidazole-4-carboxylic acid The title compound was prepared using the procedure described in Example 58(e) starting from benzyl 2-cyclopropyl-1-((2-(trimethylsilyl)ethoxy)methyl)-1H-imidazole-4-carboxylate (2.68 mmol, 1 g). Yield 700 mg. $^1$H-NMR (400 MHz; DMSO-d$_6$): δ −0.01 (s, 9H), 0.83-0.94 (m, 6H), 2.01-2.08 (m, 1H), 3.52 (t, 2H), 5.43 (s, 2H), 7.82 (s, 1H), 12.26 (bs, 1H).

c) (S)—N-(1-(3-(3-Chloro-4-cyano-5-fluorophenyl)-1H-pyrazol-1-yl)propan-2-yl)-2-cyclopropyl-1-((2-(trimethylsilyl)ethoxy)methyl)-1H-imidazole-4-carboxamide The title compound was prepared using the procedure described in Example 32(e) starting from 2-cyclopropyl-1-((2-(trimethylsilyl)ethoxy)methyl)-1H-imidazole-4-carboxylic acid (1.41 mmol, 400 mg) and (S)-4-(1-(2-aminopropyl)-1H-pyrazol-3-yl)-2-chloro-6-fluorobenzonitrile (1.41 mmol, 395 mg). The product was purified by flash-chromatography. Yield 249 mg. $^1$H-NMR (400 MHz; CDCl$_3$): δ −0.01 (s, 9H), 0.93 (t, 2H), 0.99 (d, 4H), 1.23 (d, 3H), 1.88-1.95 (m, 1H), 3.52 (t, 2H), 4.29-4.40 (m, 2H), 4.47-4.54 (m, 1H), 5.33 (s, 2H), 6.59 (d, 1H), 7.35 (d, 1H), 7.49-7.51 (m, 2H), 7.58 (d, 1H), 7.72 (s, 1H).

d) (S)—N-(1-(3-(3-Chloro-4-cyano-5-fluorophenyl)-1H-pyrazol-1-yl)propan-2-yl)-2-cyclopropyl-1H-imidazole-4-carboxamide The title compound was prepared using the procedure described in Example 52(h) starting from (S)—N-(1-(3-(3-chloro-4-cyano-5-fluorophenyl)-1H-pyrazol-1-yl)propan-2-yl)-2-cyclopropyl-1-((2-(trimethylsilyl)ethoxy)methyl)-1H-imidazole-4-carboxamide (0.46 mmol, 250 mg). Yield 70 mg. $^1$H-NMR (400 MHz; DMSO-d$_6$): δ 0.81-0.91 (m, 4H), 1.08 (d, 3H), 1.92-1.97 (m, 1H), 4.27-4.40 (m, 3H), 7.02 (bs, 1H), 7.38 (bs, 1H), 7.85-7.90 (m, 3H), 7.98 (s, 1H), 12.08 (s, 1H). LC-MS: [M+1]=413.19.

Example 71

(S)—N$^4$-(1-(3-(3-Chloro-4-cyano-5-fluorophenyl)-1H-pyrazol-1-yl)propan-2-yl)-N$^2$,N$^2$-dimethyl-1H-imidazole-2,4-dicarboxamide a) 4-Benzyl 2-ethyl 1-((2-(trimethylsilyl)ethoxy)methyl)-1H-imidazole-2,4-dicarboxylate The title compound was prepared using the procedure described in Example 52(d) starting from benzyl 2-bromo-1-((2-(trimethylsilyl)ethoxy)methyl)-1H-imidazole-4-carboxylate (0.609 mmol, 250 mg) and ethyl cyanoformate (0.91 mmol, 90 mg). Yield 97 mg. $^1$H-NMR (400 MHz; CDCl$_3$): δ −0.08 (s, 9H), 0.91 (t, 2H), 1.42 (t, 3H), 3.57 (t, 2H), 4.43 (q, 2H), 5.38 (s, 2H), 5.78 (s, 2H), 7.30-7.39 (m, 3H), 7.43-7.46 (m, 2H), 7.90 (s, 1H). LC-MS: [M+1]=405.13.

b) 2-(Ethoxycarbonyl)-1-((2-(trimethylsilyl)ethoxy)methyl)-1H-imidazole-4-carboxylic acid The title compound was prepared using the procedure described in Example 58(e) starting from 4-benzyl 2-ethyl 1-((2-(trimethylsilyl)ethoxy)methyl)-1H-imidazole-2,4-dicarboxylate (4.94 mmol, 2 g). Yield 1.61 g. $^1$H-NMR (400 MHz; DMSO-d$_6$): δ −0.07 (s, 9H), 0.74 (t, 2H), 1.32 (t, 3H), 3.52 (t, 2H), 4.32 (q, 2H), 5.70 (s, 2H), 8.23 (s, 1H), 12.76 (bs, 1H). LC-MS: [M+1]=315.04.

c) (S)-Ethyl 4-((1-(3-(3-chloro-4-cyano-5-fluorophenyl)-1H-pyrazol-1-yl)propan-2-yl)carbamoyl)-1-((2-(trimethylsilyl)ethoxy)methyl)-1H-imidazole-2-carboxylate The title compound was prepared using the procedure described in Example 32(e) starting from 2-(ethoxycarbonyl)-1-((2-(trimethylsilyl)ethoxy)methyl)-1H-imidazole-4-carboxylic acid (3.18 mmol, 1 g) and (S)-4-(1-(2-aminopropyl)-1H-pyrazol-3-yl)-2-chloro-6-fluorobenzonitrile (3.18 mmol, 890 mg). The product was purified by flash-chromatography. Yield 1.6 g. $^1$H-NMR (400 MHz; DMSO-d$_6$): δ −0.01 (s, 9H), 0.80 (t, 2H), 1.15 (d, 3H), 1.30 (t, 3H), 3.48 (t, 2H), 4.34-4.49 (m, 5H), 5.69 (s, 2H), 6.98 (d, 1H), 7.78-7.82 (m, 2H), 7.87 (s, 1H), 8.03 (s, 1H), 8.21 (d, 1H). LC-MS: [M+1]=575.11.

d) (S)-4-((1-(3-(3-Chloro-4-cyano-5-fluorophenyl)-1H-pyrazol-1-yl)propan-2-yl)carbamoyl)-1-((2-(trimethylsilyl)ethoxy)methyl)-1H-imidazole-2-carboxylic acid The title compound was prepared using the procedure described in Example 32(d) starting from (S)-ethyl 4-((1-(3-(3-chloro-4-cyano-5-fluorophenyl)-1H-pyrazol-1-yl)propan-2-yl)carbamoyl)-1-((2-(trimethylsilyl)ethoxy)methyl)-1H-imidazole-2-carboxylate (5.22 mmol, 3 g) and sodium hydroxide (7.83 mmol, 313 mg). Yield 1.49 g. LC-MS: [M+1]=547.28.

e) (S)—N$^4$-(1-(3-(3-Chloro-4-cyano-5-fluorophenyl)-1H-pyrazol-1-yl)propan-2-yl)-N$^2$,N$^2$-dimethyl-1-((2-(trimethylsilyl)ethoxy)methyl)-1H-imidazole-2,4-dicarboxamide The title compound was prepared using the procedure described in Example 32(e) starting from (S)-4-((1-(3-(3-chloro-4-cyano-5-fluorophenyl)-1H-pyrazol-1-yl)propan-2-yl)carbamoyl)-1-((2-(trimethylsilyl)ethoxy)methyl)-1H-imidazole-2-carboxylic acid (0.549 mmol, 300 mg) and N,N-dimethylamine (0.824 mmol, 37 mg). The product was purified by flash-chromatography. Yield 207 mg. $^1$H-NMR (400 MHz; CDCl$_3$): δ −0.01 (s, 9H), 0.91 (t, 2H), 1.26 (d, 3H), 3.11 (s, 3H), 3.26 (s, 3H), 3.54 (t, 2H), 4.31-4.42 (m, 2H), 4.51-4.57 (m, 1H), 5.74 (s, 2H), 6.59 (d, 1H), 7.39 (d, 1H), 7.49 (d, 1H), 7.59 (d, 1H), 7.81 (s, 1H), 7.84 (s, 1H). LC-MS: [M+1]=574.32.

f) (S)—N⁴-(1-(3-(3-Chloro-4-cyano-5-fluorophenyl)-1H-pyrazol-1-yl)propan-2-yl)-N²,N²-dimethyl-1H-imidazole-2,4-dicarboxamide The title compound was prepared using the procedure described in Example 52(h) starting from (S)—N⁴-(1-(3-(3-chloro-4-cyano-5-fluorophenyl)-1H-pyrazol-1-yl)propan-2-yl)-N²,N²-dimethyl-1-((2-(trimethylsilyl)ethoxy)methyl)-1H-imidazole-2,4-dicarboxamide (0.301 mmol, 200 mg). The product was purified by flash-chromatography. Yield 87 mg. $^1$H-NMR (400 MHz; DMSO-d$_6$): δ 1.11 (d, 3H), 3.01 (s, 3H), 3.53 (s, 3H), 4.30-4.45 (m, 3H), 7.0 (d, 1H), 7.60 (d, 1H), 7.84-7.86 (m, 2H), 7.91-7.95 (m, 2H), 13.24 (s, 1H). LC-MS: [M+1]=444.12.

Example 72

(S)—N-(1-(3-(3-Chloro-4-cyano-5-fluorophenyl)-1H-pyrazol-1-yl)propan-2-yl)-2-(2-ethoxypropan-2-yl)-1H-imidazole-4-carboxamide a) Methyl 2-(2-ethoxypropan-2-yl)-1-((2-(trimethylsilyl)ethoxy)methyl)-1H-imidazole-4-carboxylate and ethyl 2-(2-ethoxypropan-2-yl)-1-((2-(trimethylsilyl)-ethoxy)methyl)-1H-imidazole-4-carboxylate Into a flask containing methyl 2-(2-hydroxypropan-2-yl)-1-((2-(trimethyl-silyl)ethoxy)methyl)-1H-imidazole-4-carboxylate (0.95 mmol, 300 mg) in DMF (3 ml), 60% sodium hydride (2.86 mmol, 68 mg) was added in portions at 0° C. The reaction mixture was stirred for 10 min. EtI (1.91 mmol, 298 mg) was added and stirred at ambient temperature for 6 h. After completion of the reaction, the mixture was quenched with H$_2$O, extracted with EtOAc. The organic layers were washed with water, dried, filtered and evaporated. The crude was purified by flash-chromatography. The LCMS showed the mixture of methyl 2-(2-ethoxypropan-2-yl)-1-((2-(trimethylsilyl)ethoxy)methyl)-1H-imidazole-4-carboxylate and ethyl 2-(2-ethoxypropan-2-yl)-1-((2-(trimethylsilyl)ethoxy)methyl)-1H-imidazole-4-carboxylate. The mixture was preceded to the next step without any further purification. Yield 90 mg (mixture). LC-MS: [M+1]=343.42, [M+15]: 357.16.

b) 2-(2-Ethoxypropan-2-yl)-1-((2-(trimethylsilyl)ethoxy)methyl)-1H-imidazole-4-carboxylic acid The title compound was prepared using the procedure described in Example 58(e) starting from the mixture of methyl 2-(2-ethoxypropan-2-yl)-1-((2-(trimethyl-silyl)ethoxy)methyl)-1H-imidazole-4-carboxylate and ethyl 2-(2-ethoxypropan-2-yl)-1-((2-(trimethylsilyl)ethoxy)methyl)-1H-imidazole-4-carboxylate (90 mg). Yield 70 mg. $^1$H-NMR (400 MHz; DMSO-d$_6$): δ −0.02 (s, 9H), 0.87 (t, 2H), 1.06 (t, 3H), 1.57 (s, 6H), 3.12 (q, 2H), 3.58 (t, 2H), 5.53 (s, 2H), 7.93 (s, 1H), 12.28 (bs, 1H).

c) (S)—N-(1-(3-(3-Chloro-4-cyano-5-fluorophenyl)-1H-pyrazol-1-yl)propan-2-yl)-2-(2-ethoxypropan-2-yl)-1-((2-(trimethylsilyl)ethoxy)methyl)-1H-imidazole-4-carboxamide The title compound was prepared using the procedure described in Example 32(e) starting from 2-(2-ethoxypropan-2-yl)-1-((2-(trimethylsilyl)ethoxy)methyl)-1H-imidazole-4-carboxylic acid (1.15 mmol, 380 g) and (S)-4-(1-(2-aminopropyl)-1H-pyrazol-3-yl)-2-chloro-6-fluorobenzonitrile (1.15 mmol, 320 mg). The product was purified by flash-chromatography. Yield 260 mg. $^1$H-NMR (400 MHz; DMSO-d$_6$): δ −0.01 (s, 9H), 0.80-0.91 (m, 5H), 0.94 (t, 3H), 1.23 (s, 6H), 3.21 (q, 2H), 3.58 (t, 2H), 4.33-4.42 (m, 2H), 4.53-4.59 (m, 1H), 5.53 (s, 2H), 6.61 (d, 1H), 7.41 (d, 1H), 7.52 (d, 1H), 7.59 (d, 1H), 7.64 (s, 1H), 7.74 (s, 1H). LC-MS: [M+1]=589.23.

d) (S)—N-(1-(3-(3-Chloro-4-cyano-5-fluorophenyl)-1H-pyrazol-1-yl)propan-2-yl)-2-(2-ethoxypropan-2-yl)-1H-imidazole-4-carboxamide The title compound was prepared using the procedure described in Example 52(h) starting from (S)—N-(1-(3-(3-chloro-4-cyano-5-fluorophenyl)-1H-pyrazol-1-yl)propan-2-yl)-2-(2-ethoxypropan-2-yl)-1-((2-(trimethylsilyl)ethoxy)methyl)-1H-imidazole-4-carboxamide (0.39 mmol, 230 mg). The product was purified with flash-chromatography. Yield 102 mg. $^1$H-NMR (400 MHz; DMSO-d$_6$): δ 0.96 (t, 3H), 1.10 (d, 3H), 1.49 (s, 6H), 3.08 (q, 2H), 4.30-4.45 (m, 3H), 7.03 (bs, 1H), 7.51 (bs, 1H), 7.77 (d, 1H), 7.83-7.89 (m, 2H), 7.99 (s, 1H), 12.33 (bs, 1H). LC-MS: [M+1]=459.34.

Example 73

N—((S)-1-(3-(3-Chloro-4-cyano-5-fluorophenyl)-1H-pyrazol-1-yl)propan-2-yl)-2-(1-ethoxyethyl)-1H-imidazole-4-carboxamide a) Methyl 2-(1-hydroxyethyl)-1-((2-(trimethylsilyl)ethoxy)methyl)-1H-imidazole-4-carboxylate The title compound was prepared using the procedure described in Example 33(e) starting from methyl 2-acetyl-1-((2-(trimethylsilyl)ethoxy)methyl)-1H-imidazole-4-carboxylate (3.33 mmol, 1 g). Yield 970 mg. $^1$H-NMR (400 MHz; CDCl$_3$): δ −0.01 (s, 9H), 0.86 (t, 2H), 1.66 (d, 3H), 2.92 (bs, 1H), 3.52 (t, 2H), 3.90 (s, 3H), 5.02 (m, 1H), 5.41 (q, 2H), 7.66 (s, 1H).

b) Methyl 2-(1-ethoxyethyl)-1-((2-(trimethylsilyl)ethoxy)methyl)-1H-imidazole-4-carboxylate and ethyl 2-(1-ethoxyethyl)-1-((2-(trimethylsilyl)ethoxy)-methyl)-1H-imidazole-4-carboxylate The mixture of the title compounds was prepared using the procedure described in Example 72(a) starting from methyl 2-(1-hydroxyethyl)-1-((2-(trimethyl-silyl)ethoxy)methyl)-1H-imidazole-4-carboxylate (1.66 mmol, 500 mg). Yield 230 mg (mixture). LC-MS: [M+1]=329.21 [M+15]: 343.30.

c) 2-(1-Ethoxyethyl)-1-((2-(trimethylsilyl)ethoxy)methyl)-1H-imidazole-4-carboxylic acid The title compound was prepared using the procedure described in Example 58(e) starting from the mixture of methyl 2-(1-ethoxyethyl)-1-((2-(trimethylsilyl)-ethoxy)methyl)-1H-imidazole-4-carboxylate and ethyl 2-(1-ethoxyethyl)-1-((2-(trimethylsilyl)ethoxy)methyl)-1H-imidazole-4-carboxylate (600 mg). Yield 370 mg. $^1$H-NMR (400 MHz; DMSO-d$_6$): δ −0.01 (s, 9H), 0.86 (t, 2H), 1.08 (d, 3H), 1.45 (t, 3H), 3.41 (q, 2H), 3.50 (t, 2H), 4.71 (q, 1H), 5.42 (s, 2H), 7.92 (s, 1H), 12.13 (bs, 1H). LC-MS: [M+1]=315.12.

d) N—((S)-1-(3-(3-Chloro-4-cyano-5-fluorophenyl)-1H-pyrazol-1-yl)propan-2-yl)-2-(1-ethoxyethyl)-1-((2-(trimethylsilyl)ethoxy)methyl)-1H-imidazole-4-carboxamide The title compound was prepared using the procedure described in Example 32(e) starting from 2-(1-ethoxyethyl)-

1-((2-(trimethylsilyl)ethoxy)methyl)-1H-imidazole-4-carboxylic acid (1.27 mmol, 400 mg) and (S)-4-(1-(2-aminopropyl)-1H-pyrazol-3-yl)-2-chloro-6-fluorobenzonitrile (1.27 mmol, 350 mg). The product was purified by flash-chromatography. Yield 230 mg. LC-MS: [M+1]=575.28.

e) N—((S)-1-(3-(3-Chloro-4-cyano-5-fluorophenyl)-1H-pyrazol-1-yl)propan-2-yl)-2-(1-ethoxyethyl)-1H-imidazole-4-carboxamide The title compound was prepared using the procedure described in Example 52(h) starting from N—((S)-1-(3-(3-chloro-4-cyano-5-fluorophenyl)-1H-pyrazol-1-yl)propan-2-yl)-2-(1-ethoxyethyl)-1-((2-(trimethylsilyl)ethoxy)methyl)-1H-imidazole-4-carboxamide (0.39 mmol, 230 mg). The product was purified by flash-chromatography. Yield 97 mg. $^1$H-NMR (400 MHz; DMSO-$d_6$): δ 1.01-1.09 (m, 6H), 1.40 (d, 3H), 3.22-3.40 (m, 2H), 4.27-4.45 (m, 3H), 4.51 (q, 1H), 7.0 (d, 1H), 7.51 (d, 1H), 7.83-8.04 (m, 4H), 12.47 (s, 1H). LC-MS: [M+1]=445.23.

Example 74

(S)—N-(1-(3-(3-Chloro-4-cyano-5-fluorophenyl)-1H-pyrazol-1-yl)propan-2-yl)-2-(2-ethoxypropan-2-yl)oxazole-4-carboxamide a) Ethyl 2-(2-ethoxypropan-2-yl)oxazole-4-carboxylate The title compound was prepared using the procedure described in Example 72(a) starting from ethyl 2-(2-hydroxypropan-2-yl)oxazole-4-carboxylate (2.50 mmol, 500 mg). The product was purified by flash-chromatography. Yield 260 mg. $^1$H-NMR (400 MHz; CDCl$_3$): δ 1.13 (t, 3H), 1.38 (t, 3H), 1.66 (s, 6H), 3.27 (q, 2H), 4.39 (q, 2H), 8.21 (s, 1H).

b) (S)—N-(1-(3-(3-Chloro-4-cyano-5-fluorophenyl)-1H-pyrazol-1-yl)propan-2-yl)-2-(2-ethoxypropan-2-yl)oxazole-4-carboxamide The title compound was prepared using the procedure described in Example 52(g) starting from ethyl 3-(2-hydroxypropan-2-yl)-1,2,4-oxadiazole-5-carboxylate (1.1 mmol, 250 mg) and (S)-4-(1-(2-aminopropyl)-1H-pyrazol-3-yl)-2-chloro-6-fluorobenzonitrile (1.1 mmol, 300 mg). Yield 86 mg. $^1$H-NMR (400 MHz; DMSO-$d_6$): δ 1.0 (t, 3H), 1.12 (d, 3H), 1.55 (s, 6H), 3.16 (q, 2H), 4.29-4.49 (m, 3H), 7.02 (d, 1H), 7.84-7.87 (m, 2H), 7.98 (s, 1H), 8.15 (d, 1H), 8.55 (s, 1H). LC-MS: [M+1]=460.05.

Example 75

(S)—N-(1-(3-(3-Chloro-4-cyano-5-fluorophenyl)-1H-pyrazol-1-yl)propan-2-yl)-5-(2-hydroxy-2-methylpropyl)-1H-pyrazole-3-carboxamide a) Ethyl 5-(2-hydroxypropyl)-1H-pyrazole-3-carboxylate Into a flask containing ethyl diazoacetate (52.63 mmol, 6 g) in toluene (100 ml), 3-butyn-2-ol (78.94 mmol, 6.6 g) was added at RT and stirred at 100° C. for 5 h. The solvent was evaporated and the crude was purified by flash-chromatography. Yield 697 mg. $^1$H-NMR (400 MHz; CDCl$_3$): δ 1.22-1.28 (m, 3H), 1.39 (t, 3H), 2.72-2.78 (m, 1H), 2.82-2.91 (m, 1H), 4.10-4.17 (m, 1H), 4.38 (q, 2H), 6.64 (s, 1H).

b) Ethyl 5-(2-hydroxypropyl)-1-((2-(trimethylsilyl)ethoxy)methyl)-1H-pyrazole-3-carboxylate Into a flask containing ethyl 5-(2-hydroxypropyl)-1H-pyrazole-3-carboxylate (15.65 mmol, 3.2 g) in acetone (60 ml), Cs$_2$CO$_3$ (13.7 g, 99.1 mmol), SEM-Cl (9.3 ml, 51.6 mmol) were added and stirred at RT overnight. The reaction mixture was quenched by the addition of H$_2$O and extracted with EtOAc. The organic layer was concentrated and purified by column-chromatography. Yield 3.8 g. $^1$H-NMR (400 MHz; CDCl$_3$): δ −0.05 (s, 9H), 0.89 (t, 2H), 1.25 (d, 3H), 1.40 (t, 3H), 2.71-2.83 (m, 3H), 3.57 (t, 2H), 4.34 (q, 2H), 5.79 (s, 2H), 6.74 (s, 1H). LC-MS: [M+1]=329.14.

c) Ethyl 5-(2-oxopropyl)-1-((2-(trimethylsilyl)ethoxy)methyl)-1H-pyrazole-3-carboxylate The title compound was prepared using the procedure described in Example 68(a) starting from ethyl 5-(2-hydroxypropyl)-1H-pyrazole-3-carboxylate (8.84 mmol, 2.9 g). Yield 3.8 g. $^1$H-NMR (400 MHz; CDCl$_3$): δ −0.05 (s, 9H), 0.89 (t, 2H), 1.36 (t, 3H), 2.18 (s, 3H), 3.57 (t, 2H), 3.76 (s, 2H), 4.34 (q, 2H), 5.80 (s, 2H), 6.82 (s, 1H). LC-MS: [M+1]=327.26.

d) Ethyl 5-(2-hydroxy-2-methylpropyl)-1-((2-(trimethylsilyl)ethoxy)methyl)-1H-pyrazole-3-carboxylate The title compound was prepared using the procedure described in Example 2(d) starting from ethyl 5-(2-oxopropyl)-1-((2-(trimethylsilyl)ethoxy)methyl)-1H-pyrazole-3-carboxylate (5.24 mmol, 1.7 g) and 3 M solution of MeMgI in ether (6.78 mmol, 2.2 ml). Yield 301 mg. $^1$H-NMR (400 MHz; CDCl$_3$): δ −0.05 (s, 9H), 0.89 (t, 2H), 1.24 (s, 6H), 1.38 (t, 3H), 2.76 (s, 2H), 3.57 (t, 2H), 4.34 (q, 2H), 5.81 (s, 2H), 6.76 (s, 1H).

e) 5-(2-Hydroxy-2-methylpropyl)-1-((2-(trimethylsilyl)ethoxy)methyl)-1H-pyrazole-3-carboxylic acid The title compound was prepared using the procedure described in Example 32(d) starting from ethyl 5-(2-hydroxy-2-methylpropyl)-1-((2-(trimethylsilyl)ethoxy)-methyl)-1H-pyrazole-3-carboxylate (1.9 mmol, 650 mg). Yield 1.49 g. $^1$H-NMR (400 MHz; DMSO-$d_6$): δ −0.01 (s, 9H), 0.77 (t, 2H), 1.07 (s, 6H), 2.64 (s, 2H), 3.57 (t, 2H), 4.42 (bs, 1H), 5.76 (s, 2H), 6.74 (s, 1H), 12.60 (bs, 1H). LC-MS: [M+1]=315.07.

f) (S)—N-(1-(3-(3-Chloro-4-cyano-5-fluorophenyl)-1H-pyrazol-1-yl)propan-2-yl)-5-(2-hydroxy-2-methylpropyl)-1-((2-(trimethylsilyl)ethoxy)methyl)-1H-pyrazole-3-carboxamide The title compound was prepared using the procedure described in Example 32(e) starting from 5-(2-hydroxy-2-methylpropyl)-1-((2-(trimethylsilyl)ethoxy)-methyl)-1H-pyrazole-3-carboxylic acid (1.59 mmol, 500 mg) and (S)-4-(1-(2-amino-propyl)-1H-pyrazol-3-yl)-2-chloro-6-fluorobenzonitrile (1.59 mmol, 442 mg). The product was purified by flash-chromatography. Yield 295 mg. $^1$H-NMR (400 MHz; DMSO-$d_6$): δ −0.13 (s, 9H), 0.68 (t, 2H), 1.06 (s, 3H), 1.08 (s, 3H), 1.20 (d, 3H), 2.61 (s, 2H), 3.40 (t, 2H), 4.23-4.42 (m, 3H), 4.51 (s, 1H), 5.54 (d, 1H), 5.68 (d, 1H), 6.72 (s, 1H), 7.01 (d, 1H), 7.84-7.87 (m, 2H), 7.96 (s, 1H), 8.40 (d, 1H). LC-MS: [M+1]=575.01.

g) (S)—N-(1-(3-(3-Chloro-4-cyano-5-fluorophenyl)-1H-pyrazol-1-yl)propan-2-yl)-5-(2-hydroxy-2-methylpropyl)-1H-pyrazole-3-carboxamide The title compound was prepared using the procedure described in Example 52(h) starting from (S)—N-(1-(3-(3-chloro-4-cyano-5-fluorophenyl)-1H-pyrazol-1-yl)propan-2-yl)-5-(2-hydroxy-2-methylpropyl)-1-((2-(trimethylsilyl)ethoxy)methyl)-1H-pyrazole-3-carboxamide (0.514 mmol, 295 mg). The product was purified by flash-chromatography. Yield 85 mg. $^1$H-NMR (400 MHz; DMSO-$d_6$): δ 1.06 (s, 6H), 1.13 (d, 3H), 2.67 (s, 2H), 4.25-4.48 (m, 3H), 4.51 (s, 1H), 6.34 (s, 1H), 7.0 (d, 1H), 7.83-7.88 (m, 2H), 7.96 (d, 1H), 8.28 (d, 1H), 12.78 (s, 1H). LC-MS: [M+1]=445.18.

ABBREVIATIONS

ACN—Acetonitrile
AIBN—Azobisisobutyronitrile
(Boc)$_2$O—Di-t-butyl dicarbonate
DCM—Dichloromethane
DIAD—Di-tert-butyl azodicarboxylate
DIPEA—N,N-diisopropylethylamine
DME—Ethylene glycol dimethyl ether
DMF—N,N-Dimethylformamide
DMSO—Dimethylsulfoxide
DMAP—4-Dimethylaminopyridine
Dppf—1,1'-bis(diphenylphosphanyl) ferrocene
EDCI—1-(3-Dimethylaminopropyl)-3-ethylcarbodi-imide hydrochloride
EtOAc—Ethyl acetate
EtOH—Ethanol
HBTU—O-(benzotriazol-1-yl)-N,N,N',N"-tetramethyluroniumhexafluorophosphate
HOBt—1-Hydroxybenzotriazole
MeOH—Methanol
MTBE—Methyl-tert-butyl ether
NBS—N-bromosuccinimide
NMP—N-methylpyrrolidone
RT—Room temperature
SEM-Cl—2-(Trimethylsilyl)ethoxymethyl chloride
TBME—tert-Butylmethyl ether
TBDMSCl—tert-Butyldimethylchlorosilane
THF—Tetrahydrofuran

The invention claimed is:
1. A compound of formula (I) or (II)

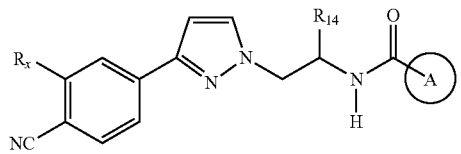
(I)

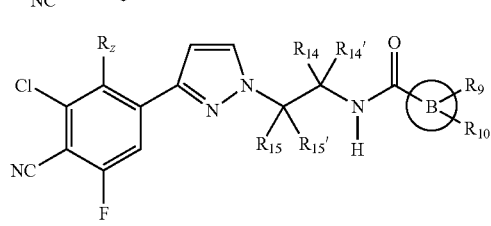
(II)

wherein ring A is any one of the following groups or tautomers thereof

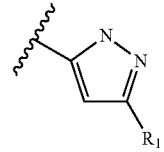
(1)

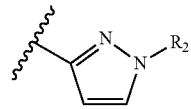
(2)

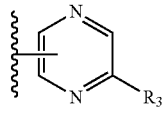
(3)

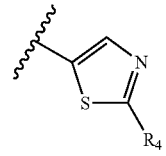
(4)

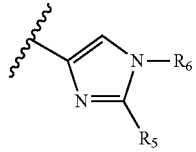
(5)

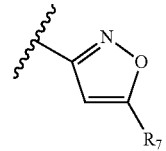
(6)

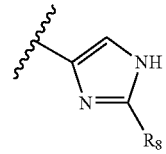
(7)

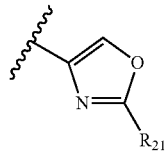
(8)

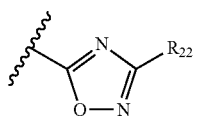
(9)

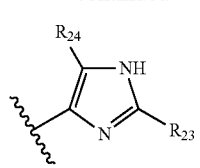

(10)

wherein
$R_X$ is halogen or $CF_3$;
$R_{X'}$ is hydrogen or halogen;
$R_1$ is hydroxy $C_{3-7}$ alkyl, imidazolyl or —$R_A$OC(O)—$R_B$;
$R_A$ is $C_{1-7}$ alkyl;
$R_B$ is $C_{1-7}$ alkyl, hydroxy $C_{1-7}$ alkyl or carboxy $C_{1-7}$ alkyl;
$R_2$ is $C_{1-7}$ alkyl, $C_{2-7}$ alkenyl, $C_{3-7}$ cycloalkyl, $C_{3-7}$ cycloalkyl $C_{1-7}$ alkyl, methylpyrazolyl or pyrimidinyl;
$R_3$ is halogen or pyridinyl;
$R_4$ is pyridinyl;
$R_5$ is $C_{1-7}$ alkyl, $C_{2-7}$ alkenyl, $C_{3-7}$ cycloalkyl, $C_{3-7}$ cycloalkyl $C_{1-7}$ alkyl, cyano, hydroxy $C_{1-7}$ alkyl, oxo $C_{1-7}$ alkyl, halogen or methylpyrazolyl;
$R_6$ is $C_{1-7}$ alkyl, $C_{2-7}$ alkenyl, $C_{3-7}$ cycloalkyl, $C_{3-7}$ cycloalkyl $C_{1-7}$ alkyl, hydroxy, hydroxy $C_{1-7}$ alkyl, cyano $C_{1-7}$ alkyl or $C_{1-7}$ alkoxycarbamoyl $C_{1-7}$ alkyl;
$R_7$ is hydroxy $C_4$ alkyl;
$R_8$ is halogen, $C_{2-7}$ alkyl, $C_{2-7}$ alkenyl, $C_{3-7}$ cycloalkyl, $C_{3-7}$ cycloalkyl $C_{1-7}$ alkyl, cyano, carboxy, oxo $C_{1-7}$ alkyl, halo $C_{1-7}$ alkyl, hydroxy $C_{1-7}$ alkyl, tetrahydro-2H-thiopyran or —C(O)—NHR$_{20}$;
$R_9$ is hydrogen, hydroxy, halogen, nitro, amino, cyano, oxo, $C_{1-7}$ alkyl, $C_{2-7}$ alkenyl, $C_{3-7}$ cycloalkyl, $C_{1-7}$ alkoxy, halo $C_{1-7}$ alkyl, hydroxy $C_{1-7}$ alkyl, cyano $C_{1-7}$ alkyl, amino $C_{1-7}$ alkyl, oxo $C_{1-7}$ alkyl, $C_{1-7}$ alkoxy $C_{1-7}$ alkyl, $C_{1-7}$ alkylamino, hydroxy $C_{1-7}$ alkylamino, $C_{1-7}$ alkoxy $C_{1-7}$ alkylamino, $C_{1-7}$ alkylamino $C_{1-7}$ alkyl, hydroxy $C_{1-7}$ alkylamino $C_{1-7}$ alkyl, hydroxyimino $C_{1-7}$ alkyl, $C_{1-7}$ alkoxycarbamoyl $C_{1-7}$ alkyl, —C(O)R$_{11}$, —OC(O)R$_{17}$, —NH—C(O)R$_{18}$—NH—SO$_2$—R$_{19}$ or an optionally substituted 5-12 membered carbocyclic or heterocyclic ring, each group linked to B-ring via a bond or via a $C_{1-7}$ alkylene linker;
$R_{10}$ is hydrogen, halogen, $C_{1-7}$ alkyl, $C_{2-7}$ alkenyl, $C_{3-7}$ cycloalkyl, $C_{3-7}$ cycloalkyl $C_{1-7}$ alkyl, oxo, hydroxy $C_{1-7}$ alkyl, oxo $C_{1-7}$ alkyl or an optionally substituted 5 or 6 membered carbocyclic or heterocyclic ring;
$R_{11}$ is hydrogen, hydroxy, $C_{1-7}$ alkyl, hydroxy $C_{1-7}$ alkyl, $C_{2-7}$ alkenyl, $C_{3-7}$ cycloalkyl, halo $C_{1-7}$ alkyl, $C_{1-7}$ alkoxy, NR$_{12}$R$_{13}$, or an optionally substituted 5-12 membered carbocyclic or heterocyclic ring;
$R_{12}$ is hydrogen, $C_{1-7}$ alkyl, $C_{2-7}$ alkenyl, $C_{3-7}$ cycloalkyl, $C_{3-7}$ cycloalkyl $C_{1-7}$ alkyl, $C_{1-7}$ alkoxy, hydroxy $C_{1-7}$ alkyl, amino $C_{1-7}$ alkyl or $C_{1-7}$ alkyl amino $C_{1-7}$ alkyl;
$R_{13}$ is hydrogen or $C_{1-7}$ alkyl;
$R_{14}$ and $R_{15}$ are, independently, hydrogen or $C_{1-7}$ alkyl;
$R_{14}'$ and $R_{15}'$ are, independently, hydrogen or $C_{1-7}$ alkyl, or $R_{14}'$ and $R_{15}'$ together form a bond;
$R_{17}$ is $C_{1-7}$ alkyl, $C_{2-7}$ alkenyl, $C_{3-7}$ cycloalkyl, $C_{3-7}$ cycloalkyl $C_{1-7}$ alkyl, $C_{1-7}$ alkoxy, amino $C_{1-7}$ alkyl, $C_{1-7}$ alkylamino or $C_{1-7}$ alkylamino $C_{1-7}$ alkyl;
$R_{18}$ is $C_{1-7}$ alkyl, $C_{2-7}$ alkenyl, $C_{3-7}$ cycloalkyl, $C_{3-7}$ cycloalkyl $C_{1-7}$ alkyl, amino $C_{1-7}$ alkyl, $C_{1-7}$ alkylamino or $C_{1-7}$ alkylamino $C_{1-7}$ alkyl;
$R_{19}$ is $C_{1-7}$ alkyl, $C_{2-7}$ alkenyl, $C_{3-7}$ cycloalkyl or $C_{3-7}$ cycloalkyl $C_{1-7}$ alkyl;
$R_{20}$ is hydrogen, $C_{1-7}$ alkyl, $C_{2-7}$ alkenyl, $C_{3-7}$ cycloalkyl, $C_{3-7}$ cycloalkyl $C_{1-7}$ alkyl or $C_{1-7}$ alkoxy;
$R_{21}$ is cyano $C_{1-7}$ alkyl or, in case $R_x$ is $CF_3$, $R_{21}$ can also be hydroxy $C_{1-7}$ alkyl;
$R_{22}$ is hydroxy $C_{1-7}$ alkyl;
$R_{23}$ is $C_{1-7}$ alkyl or hydroxy $C_{1-7}$ alkyl;
$R_{24}$ is hydroxy, halogen or $C_1$—, alkoxy;
ring B is chosen from any one of the following groups and tautomers thereof

(1')

(2')

(3')

(4')

(5')

(6')

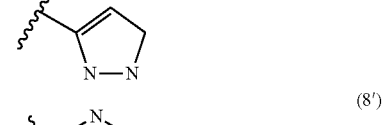

(7')

(8')

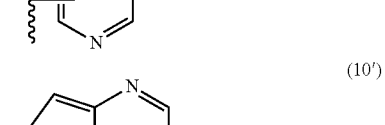

(9')

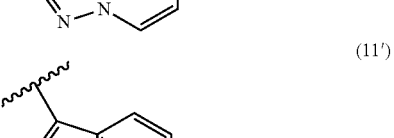

(10')

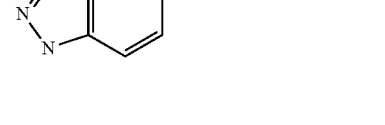

(11')

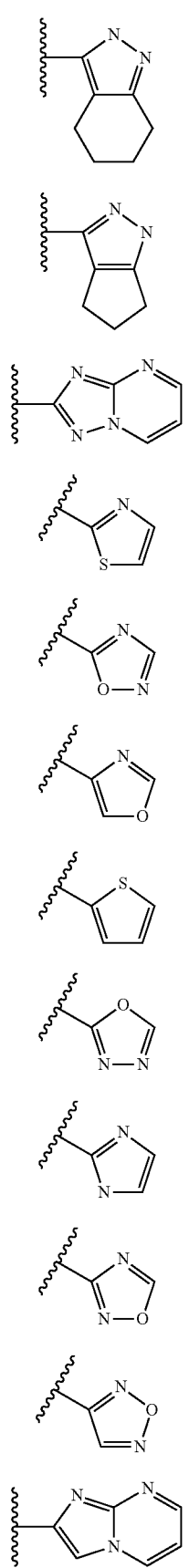
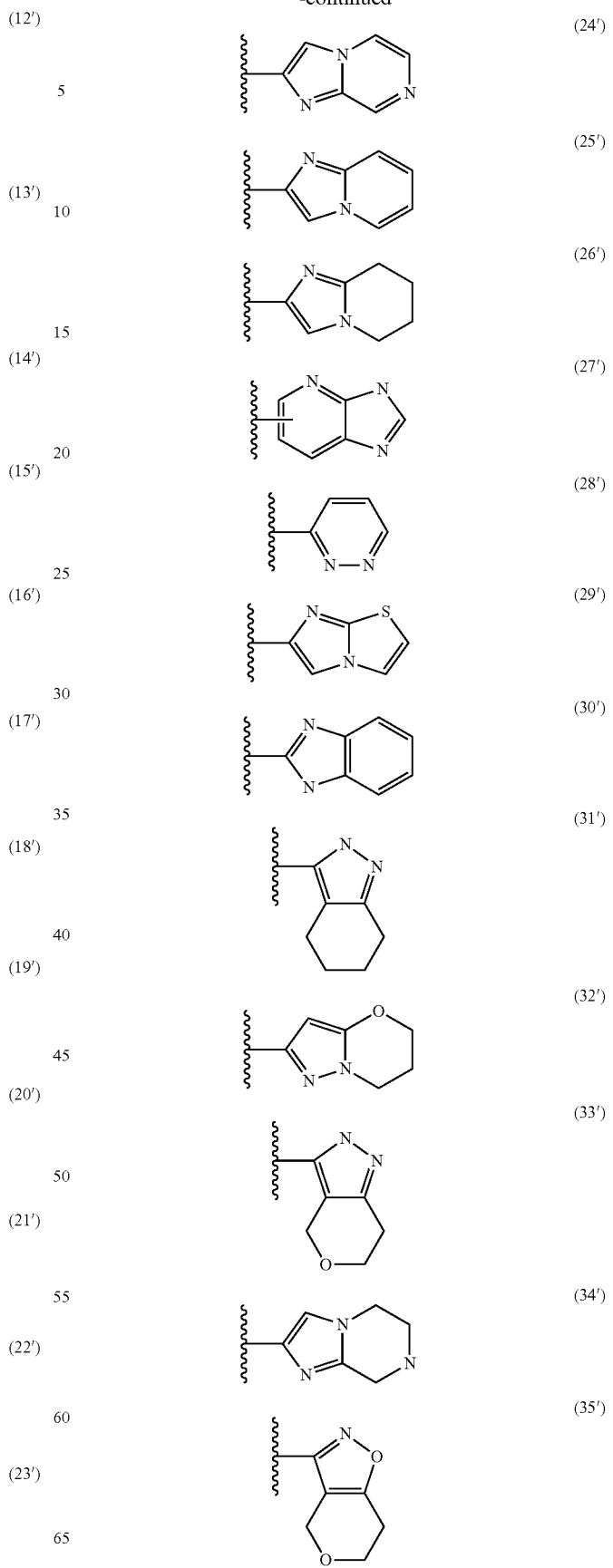

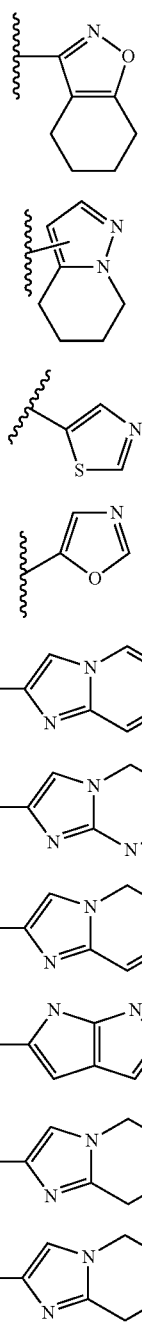

or pharmaceutically acceptable salts thereof;
with the proviso that the compound of formula (II) is not any of the following compounds:

(S)-3-acetyl-N-(1-(3-(3-chloro-4-cyano-5-fluorophenyl)-1H-pyrazol-1-yl)propan-2-yl)-1H-pyrazole-5-carboxamide;

(S)—N-(1-(3-(3-chloro-4-cyano-5-fluorophenyl)-1H-pyrazol-1-yl)propan-2-yl)-1-(pyridin-4-yl)-1H-pyrazole-3-carboxamide;

(S)—N-(1-(3-(3-chloro-4-cyano-5-fluorophenyl)-1H-pyrazol-1-yl)propan-2-yl)-1-(2-fluoroethyl)-2-methyl-1H-imidazole-4-carboxamide;

(S)—N-(1-(3-(3-chloro-4-cyano-5-fluorophenyl)-1H-pyrazol-1-yl)propan-2-yl)-3-(1H-imidazol-4-yl)-1,2,4-oxadiazole-5-carboxamide;

(S)-5-acetyl-N-(1-(3-(3-chloro-4-cyano-5-fluorophenyl)-1H-pyrazol-1-yl)propan-2-yl)isoxazole-3-carboxamide;

N—((S)-1-(3-(3-chloro-4-cyano-5-fluorophenyl)-1H-pyrazol-1-yl)propan-2-yl)-5-(1-hydroxyethyl)isoxazole-3-carboxamide;

(S)-5-acetyl-N-(2-(3-(3-chloro-4-cyano-5-fluorophenyl)-1H-pyrazol-1-yl)propyl)isoxazole-3-carboxamide;

(S)—N-(2-(3-(3-chloro-4-cyano-5-fluorophenyl)-1H-pyrazol-1-yl)propyl)-2-methyl-1H-imidazole-4-carboxamide;

N—((S)-1-(3-(3-chloro-4-cyano-5-fluorophenyl)-1H-pyrazol-1-yl)propan-2-yl)-3-(1-hydroxyethyl)-1H-pyrazole-5-carboxamide;

(R)—N-(1-(3-(3-chloro-4-cyano-5-fluorophenyl)-1H-pyrazol-1-yl)propan-2-yl)-2-methyl-1H-imidazole-4-carboxamide;

(S)—N-{1-[3-(3-Chloro-4-cyano-5-fluorophenyl)-1H-pyrazol-1-yl]propan-2-yl}-2-methyl-1H-imidazole-4-carboxamide;

(S)—N-{1-[3-(3-Chloro-4-cyano-5-fluorophenyl)-1H-pyrazol-1-yl]propan-2-yl}-1-methyl-1H-imidazole-4-carboxamide;

(S)—N-(1-(3-(3-chloro-4-cyano-5-fluorophenyl)-1H-pyrazol-1-yl)propan-2-yl)-3H-imidazo[4,5-b]pyridine-5-carboxamide;

(S)—N-(1-(3-(3-chloro-4-cyano-5-fluorophenyl)-1H-pyrazol-1-yl)propan-2-yl)-2-(pyridin-3-yl)thiazole-4-carboxamide;

(S)—N-(1-(3-(3-chloro-4-cyano-5-fluorophenyl)-1H-pyrazol-1-yl)propan-2-yl)-1-(pyridin-3-yl)-1H-pyrazole-3-carboxamide;

(S)—N-(1-(3-(3-chloro-4-cyano-5-fluorophenyl)-1H-pyrazol-1-yl)propan-2-yl)-2-methyl-1-(3-oxobutyl)-1H-imidazole-4-carboxamide;

(S)—N-(1-(3-(3-chloro-4-cyano-5-fluorophenyl)-1H-pyrazol-1-yl)propan-2-yl)-1-(3-hydroxy-3-methylbutyl)-2-methyl-1H-imidazole-4-carboxamide;

(S)—N-(1-(3-(3-chloro-4-cyano-5-fluorophenyl)-1H-pyrazol-1-yl)propan-2-yl)imidazo[1,2-a]pyridine-2-carboxamide;

(S)—N-(1-(3-(3-chloro-4-cyano-5-fluorophenyl)-1H-pyrazol-1-yl)propan-2-yl)-1-(pyridin-3-yl)-1H-imidazole-4-carboxamide;

(S)—N-(1-(3-(3-chloro-4-cyano-5-fluorophenyl)-1H-pyrazol-1-yl)propan-2-yl)-2-(2-hydroxypropan-2-yl)oxazole-4-carboxamide;

(S)—N-(1-(3-(3-chloro-4-cyano-5-fluorophenyl)-1H-pyrazol-1-yl)propan-2-yl)imidazo[1,2-a]pyrimidine-2-carboxamide;

(S)—N-(1-(3-(3-chloro-4-cyano-5-fluorophenyl)-1H-pyrazol-1-yl)propan-2-yl)-3-fluoroimidazo[1,2-a]pyridine-2-carboxamide;

(S)—N-(1-(3-(3-chloro-4-cyano-5-fluorophenyl)-1H-pyrazol-1-yl)propan-2-yl)-4,5,6,7-tetrahydro-2H-indazole-3-carboxamide;

(S)—N-(1-(3-(3-chloro-4-cyano-5-fluorophenyl)-1H-pyrazol-1-yl)propan-2-yl)-6,7-dihydro-5H-pyrazolo[5,1-b][1,3]oxazine-2-carboxamide;

(S)—N-(1-(3-(3-chloro-4-cyano-5-fluorophenyl)-1H-pyrazol-1-yl)propan-2-yl)-2,4,6,7-tetrahydropyrano[4,3-c]pyrazole-3-carboxamide;

(S)—N-(1-(3-(3-chloro-4-cyano-5-fluorophenyl)-1H-pyrazol-1-yl)propan-2-yl)-1-(6-methylpyridin-2-yl)-1H-imidazole-4-carboxamide;

(S)—N-(1-(3-(3-chloro-4-cyano-5-fluorophenyl)-1H-pyrazol-1-yl)propan-2-yl)-6,7-dihydro-4H-pyrano[3,4-d]isoxazole-3-carboxamide; or (S)—N-(1-(3-(3-chloro-4-cyano-5-fluorophenyl)-1H-pyrazol-1-yl)propan-2-yl)-5-(2-hydroxypropan-2-yl)isoxazole-3-carboxamide.

2. The compound according to claim 1, wherein the compound is of formula (I), wherein $R_x$ is halogen; $R_{14}$ is $C_{1-7}$ alkyl; and ring A is chosen from groups (1), (2), (3), (5), (6), (7) and (8).

3. The compound according to claim 2, wherein $R_x$ is chloro, $R_{14}$ is methyl, and ring A is any of groups (1), (2), (5), (6) or (7), $R_1$ is hydroxy $C_{3-7}$ alkyl, imidazolyl or carboxy $C_{1-7}$ alkyl carbonyloxy $C_{1-7}$ alkyl; $R_2$ is $C_{1-7}$ alkyl, $C_{2-7}$ alkenyl or methylpyrazolyl; $R_5$ is $C_{1-7}$ alkyl, $C_{3-7}$ cycloalkyl, hydroxy $C_{1-7}$ alkyl or methylpyrazolyl; $R_6$ is $C_{1-7}$ alkyl, cyano $C_{1-7}$ alkyl or hydroxy $C_{1-7}$ alkyl; and $R_8$ is $C_{1-7}$ alkyl, halogen, oxo $C_{1-7}$ alkyl or hydroxy $C_{1-7}$ alkyl.

4. The compound according to claim 1, wherein the compound is of formula (II) wherein $R_{14}$ is $C_{1-7}$ alkyl; $R_{14}'$, $R_{15}$ and $R_{15}'$ is hydrogen; ring B is chosen from groups (1'), (2'), (3'), (4'), (8'), (16'), (17'), (21'), (23'), (24'), (25'), (26'), (29'), (39'), (40'), (42') and (43'); $R_9$ is hydrogen, halogen, cyano, oxo, $C_{1-7}$ alkyl, $C_{2-7}$ alkenyl, $C_{3-7}$ cycloalkyl, halo $C_{1-7}$ alkyl, cyano $C_{1-7}$ alkyl, hydroxy $C_{1-7}$ alkyl, oxo $C_{1-7}$ alkyl, —NH—SO$_2$—R$_{19}$ or an optionally substituted 5-12 membered heterocyclic ring, wherein each $R_9$ group is linked to B-ring via a bond or via a $C_{1-7}$ alkylene linker; $R_{10}$ is hydrogen, $C_{1-7}$ alkyl or $C_{3-7}$ cycloalkyl; and $R_{19}$ is $C_{1-7}$ alkyl.

5. The compound according to claim 4, wherein the 5-12 membered heterocyclic ring is pyrazole, pyridine, isoxazole or imidazole ring, wherein the 5-12 membered heterocyclic ring is attached to B-ring via a bond or via $C_{1-7}$ alkylene linker.

6. The compound according to claim 5, wherein the 5-12 membered heterocyclic ring contains comprises 1-3 substituents chosen from $C_{1-7}$ alkyl, $C_{3-7}$ cycloalkyl, halogen and hydroxy $C_{1-7}$ alkyl.

7. The compound according to claim 4, wherein $R_z$ is hydrogen or fluoro, $R_{14}$ is methyl; $R_{14}'$, $R_{15}$ and $R_{15}'$ is hydrogen; ring B is any of groups (1'), (2'), (4'), (17'), (21') or (25'); $R_9$ is hydrogen, halogen, cyano, oxo, $C_{1-7}$ alkyl, $C_{2-7}$ alkenyl, $C_{3-7}$ cycloalkyl, halo $C_{1-7}$ alkyl, hydroxy $C_{1-3}$ alkyl, cyano $C_{1-7}$ alkyl, pyrazolyl, N-methylpyrazolyl, pyridinyl, isoxazolyl, imidazolyl or imidazolyl methyl; and $R_{10}$ is hydrogen, $C_{1-7}$ alkyl or $C_{3-7}$ cycloalkyl.

8. The compound according to claim 1, wherein the compound is (S)—N-(1-(3-(3-Chloro-4-cyano-2,5-difluorophenyl)-1H-pyrazol-1-yl)propan-2-yl)-2-methyl-1H-imidazole-5-carboxamide;

(S)—N-(1-(3-(3-Chloro-4-cyano-2,5-difluorophenyl)-1H-pyrazol-1-yl)-propan-2-yl)-2-(2-hydroxypropan-2-yl)oxazole-5-carboxamide;

(S)—N-(1-(3-(3-Chloro-4-cyano-5-fluorophenyl)-1H-pyrazol-1-yl)propan-2-yl)-6-cyanoimidazo[1,2-a]pyridine-2-carboxamide;

(S)—N-(1-(3-(3-Chloro-4-cyano-5-fluorophenyl)-1H-pyrazol-1-yl)propan-2-yl)-7-oxo-5,6,7,8-tetrahydroimidazo[1,2-a]pyrimidine-2-carboxamide;

(S)—N-(1-(3-(3-Chloro-4-cyano-5-fluorophenyl)-1H-pyrazol-1-yl)propan-2-yl)-3-isopropyl-1,2,4-oxadiazole-5-carboxamide;

(S)—N-(1-(3-(3-Chloro-4-cyano-5-fluorophenyl)-1H-pyrazol-1-yl)propan-2-yl)-5,7-dimethylimidazo[1,2-c]pyrimidine-2-carboxamide;

(S)-5-((1H-Imidazol-1-yl)methyl)-N-(1-(3-(3-chloro-4-cyano-5-fluorophenyl)-1H-pyrazol-1-yl)propan-2-yl)isoxazole-3-carboxamide;

(S)—N-(1-(3-(3-Chloro-4-cyano-5-fluorophenyl)-1H-pyrazol-1-yl)propan-2-yl)-5-oxo-5,6-dihydroimidazo[1,2-c]pyrimidine-2-carboxamide;

(S)—N-(1-(3-(3-Chloro-4-cyano-5-fluorophenyl)-1H-pyrazol-1-yl)propan-2-yl)-1,6-dihydropyrrolo[2,3-c]pyrazole-5-carboxamide;

(S)—N-(1-(3-(3-Chloro-4-cyano-5-fluorophenyl)-1H-pyrazol-1-yl)propan-2-yl)imidazo[2,1-b]thiazole-6-carboxamide;

(S)—N-(1-(3-(3-Chloro-4-cyano-5-fluorophenyl)-1H-pyrazol-1-yl)propan-2-yl)-6-nitroimidazo[1,2-a]pyridine-2-carboxamide;

(S)—N-(1-(3-(3-Chloro-4-cyano-5-fluorophenyl)-1H-pyrazol-1-yl)propan-2-yl)-5,6,7,8-tetrahydroimidazo[1,2-a]pyridine-2-carboxamide;

(S)—N-(1-(3-(3-Chloro-4-cyano-5-fluorophenyl)-1H-pyrazol-1-yl)-propan-2-yl)-1-isopropyl-2-methyl-1H-imidazole-4-carboxamide;

(S)—N-(1-(3-(3-Chloro-4-cyano-5-fluorophenyl)-1H-pyrazol-1-yl)propan-2-yl)-5-(2-hydroxypropan-2-yl)-1H-pyrazole-3-carboxamide;

(S)—N-(1-(3-(3-Chloro-4-cyano-5-fluorophenyl)-1H-pyrazol-1-yl)-propan-2-yl)-1-(2,2-difluoroethyl)-2-methyl-1H-imidazole-4-carboxamide;

N—((S)-1-(3-(3-Chloro-4-cyano-5-fluorophenyl)-1H-pyrazol-1-yl)-propan-2-yl)-1-((R)-2-hydroxypropyl)-2-methyl-1H-imidazole-4-carboxamide;

(S)—N-(1-(3-(3-Chloro-4-cyano-5-fluorophenyl)-1H-pyrazol-1-yl)propan-2-yl)-1'-methyl-1'1H-1,4'-bipyrazole-3-carboxamide;

(S)—N-(1-(3-(3-Chloro-4-cyano-5-fluorophenyl)-1H-pyrazol-1-yl)propan-2-yl)-1H,2'H-3,3'-bipyrazole-5-carboxamide;

N—((S)-1-(3-(3-Chloro-4-cyano-5-fluorophenyl)-1H-pyrazol-1-yl)-propan-2-yl)-1-((S)-2-hydroxypropyl)-2-methyl-1H-imidazole-4-carboxamide;

(S)—N-(1-(3-(3-Chloro-4-cyano-5-fluorophenyl)-1H-pyrazol-1-yl)propan-2-yl)-3,3'-bipyridine-6-carboxamide;

(S)—N-(1-(3-(3-Chloro-4-cyano-5-fluorophenyl)-1H-pyrazol-1-yl)-propan-2-yl)-6-(3,3-dimethylureido)imidazo[1,2-a]pyridine-2-carboxamide;

(S)—N-(1-(3-(3-Chloro-4-cyano-5-fluorophenyl)-1H-pyrazol-1-yl)propan-2-yl)-6-(methylsulfonamido)imidazo[1,2-a]pyridine-2-carboxamide;

N—((S)-1-(3-(3-Chloro-4-cyano-5-fluorophenyl)-1H-pyrazol-1-yl)-propan-2-yl)-5-(1-hydroxy-2-methylpropyl)isoxazole-3-carboxamide;

(S)—N-(1-(3-(3-Chloro-4-cyano-5-fluorophenyl)-1H-pyrazol-1-yl)propan-2-yl)-5-(1,5-dimethyl-1H-pyrazol-3-yl)-1,2,4-oxadiazole-3-carboxamide;

(S)—N-(1-(3-(3-Chloro-4-cyano-5-fluorophenyl)-1H-pyrazol-1-yl)propan-2-yl)-5-(isoxazol-3-yl)-1,2,4-oxadiazole-3-carboxamide;

(S)—N-(1-(3-(3-Chloro-4-cyano-5-fluorophenyl)-1H-pyrazol-1-yl)-propan-2-yl)-3-(1H-imidazol-4-yl)-1H-pyrazole-5-carboxamide;

(S)—N-(1-(3-(3-Chloro-4-cyano-5-fluorophenyl)-1H-pyrazol-1-yl)propan-2-yl)-2-(chloropropan-2-yl)oxazole-4-carboxamide;

(S)—N-(1-(3-(3-Chloro-4-cyano-5-fluorophenyl)-1H-pyrazol-1-yl)-propan-2-yl)-2-(2-propen-2-yl)oxazole-4-carboxamide;

(S)—N-(1-(3-(3-Chloro-4-cyano-5-fluorophenyl)-1H-pyrazol-1-yl)propan-2-yl)-N-5-cyclopropylisoxazole-3,5-dicarboxamide;

(S)-2-Bromo-N-(1-(3-(3-chloro-4-cyano-5-fluorophenyl)-1H-pyrazol-1-yl)propan-2-yl)-1H-imidazole-4-carboxamide;

(S)—N-(1-(3-(3-Chloro-4-cyano-5-fluorophenyl)-1H-pyrazol-1-yl)propan-2-yl)-1-(2-methylprop-1-enyl)-1H-pyrazole-3-carboxamide;

(S)—N-(1-(3-(3-Chloro-4-cyano-5-fluorophenyl)-1H-pyrazol-1-yl)propan-2-yl)-1-cyclopropyl-1H-pyrazole-3-carboxamide;

N—((S)-1-(3-(3-Chloro-4-cyano-5-fluorophenyl)-1H-pyrazol-1-yl)propan-2-yl)-2-(1-hydroxyethyl)-1H-imidazole-4-carboxamide;

(S)-2-acetyl-N-(1-(3-(3-chloro-4-cyano-5-fluorophenyl)-1H-pyrazol-1-yl)propan-2-yl)-1H-imidazole-4-carboxamide;

(S)—N-(1-(3-(3-Chloro-4-cyano-5-fluorophenyl)-1H-pyrazol-1-yl)propan-2-yl)-2-(2-hydroxypropan-2-yl)-1H-imidazole-4-carboxamide;

(S)—N-(1-(3-(3-Chloro-4-cyano-5-fluorophenyl)-1H-pyrazol-1-yl)-propan-2-yl)-2-cyclopropyl-1-methyl-1H-imidazole-4-carboxamide;

(S)—$N^4$-(1-(3-(3-Chloro-4-cyano-5-fluorophenyl)-1H-pyrazol-1-yl)propan-2-yl)-1H-imidazole-2,4-dicarboxamide:

4-(1-(3-((S)-1-(3-(3-Chloro-4-cyanophenyl)-1H-pyrazol-1-yl)propan-2-yl-carbamoyl)-1H-pyrazol-5-yl)ethoxy)-4-oxobutanoic acid;

(S)-5-Chloro-N-(1-(3-(3-chloro-4-cyanophenyl)-1H-pyrazol-1-yl)-propan-2-yl)-pyrazine-2-carboxamide;

N—((S)-1-(3-(3-Chloro-4-cyanophenyl)-1H-pyrazol-1-yl)propan-2-yl)-1-((S)-2-hydroxypropyl)-2-methyl-1H-imidazole-4-carboxamide;

(S)-1-Butyl-N-(1-(3-(3-chloro-4-cyanophenyl)-1H-pyrazol-1-yl)propan-2-yl)-2-methyl-1H-imidazole-4-carboxamide;

(S)—N-(1-(3-(3-Chloro-4-cyanophenyl)-1H-pyrazol-1-yl)propan-2-yl)-5-(2-hydroxypropan-2-yl)-1H-pyrazole-3-carboxamide;

(S)—N-(1-(3-(3-Chloro-4-cyanophenyl)-1H-pyrazol-1-yl)propan-2-yl)-1'-methyl-1'1H-1,4'-bipyrazole-3-carboxamide;

N—((S)-1-(3-(3-Chloro-4-cyanophenyl)-1H-pyrazol-1-yl)propan-2-yl)-1-((R)-2-hydroxypropyl)-2-methyl-1H-imidazole-4-carboxamide;

(S)-2-Bromo-N-(1-(3-(3-chloro-4-cyanophenyl)-1H-pyrazol-1-yl)-propan-2-yl)-1H-imidazole-4-carboxamide;

N—((S)-1-(3-(3-Chloro-4-cyanophenyl)-1H-pyrazol-1-yl)propan-2-yl)-5-(1-hydroxy-2-methylpropyl)isoxazole-3-carboxamide;

(S)—N-(1-(3-(3-Chloro-4-cyanophenyl)-1H-pyrazol-1-yl)propan-2-yl)-1-(2-cyanoethyl)-2-methyl-1H-imidazole-4-carboxamide;

N—((S)-1-(3-(3-Chloro-4-cyanophenyl)-1H-pyrazol-1-yl)propan-2-yl)-1-(1-cyanoethyl)-2-methyl-1H-imidazole-4-carboxamide;

(S)—N-(1-(3-(3-Chloro-4-cyanophenyl)-1H-pyrazol-1-yl)propan-2-yl)-1-(2-methylprop-1-enyl)-1H-pyrazole-3-carboxamide;

(S)—N-(1-(3-(3-Chloro-4-cyanophenyl)-1H-pyrazol-1-yl)propan-2-yl)-3-(1H-imidazol-4-yl)-1H-pyrazole-5-carboxamide;

(S)—N-(1-(3-(3-Chloro-4-cyanophenyl)-1H-pyrazol-1-yl)propan-2-yl)-1-cyclopropyl-1H-pyrazole-3-carboxamide;

(S)—N-(1-(3-(3-Chloro-4-cyanophenyl)-1H-pyrazol-1-yl)propan-2-yl)-1-(6-(dimethylamino)pyridin-3-yl)-1H-pyrazole-3-carboxamide;

(S)—N-(1-(3-(3-Chloro-4-cyanophenyl)-1H-pyrazol-1-yl)propan-2-yl)-4,5,6,7-tetrahydropyrazolo[1,5-a]pyridine-2-carboxamide);

N—((S)-1-(3-(3-Chloro-4-cyanophenyl)-1H-pyrazol-1-yl)propan-2-yl)-2-(1-hydroxyethyl)-1H-imidazole-4-carboxamide;

(S)—N-(1-(3-(3-Chloro-4-cyanophenyl)-1H-pyrazol-1-yl)propan-2-yl)-2-isopropyl-1H-imidazole-4-carboxamide;

(S)-2-Butyl-N-(1-(3-(3-chloro-4-cyanophenyl)-1H-pyrazol-1-yl)propan-2-yl)-1-methyl-1H-imidazole-4-carboxamide;

(S)—N-(1-(3-(3-Chloro-4-cyanophenyl)-1H-pyrazol-1-yl)propan-2-yl)-2-(2-hydroxypropan-2-yl)-1-methyl-1H-imidazole-4-carboxamide;

(S)—N-(1-(3-(3-Chloro-4-cyanophenyl)-1H-pyrazol-1-yl)propan-2-yl)-1-methyl-2-(1-methyl-1H-pyrazol-4-yl)-1H-imidazole-4-carboxamide;

(S)—N-(1-(3-(3-Chloro-4-cyanophenyl)-1H-pyrazol-1-yl)propan-2-yl)-2-cyclopropyl-1-methyl-1H-imidazole-4-carboxamide;

(S)—$N^4$-(1-(3-(3-Chloro-4-cyanophenyl)-1H-pyrazol-1-yl)propan-2-yl)-1H-imidazole-2,4-dicarboxamide;

(S)—N-(1-(3-(4-Cyano-3-(trifluoromethyl)phenyl)-1H-pyrazol-1-yl)propan-2-yl)-2-(2-hydroxypropan-2-yl)oxazole-4-carboxamide or a pharmaceutically acceptable salt thereof.

9. The compound according to claim 1, wherein the compound is (S)—N-(2-(3-(3-Chloro-4-cyano-5-fluorophenyl)-1H-pyrazol-1-yl)propyl)-2-(2-hydroxypropan-2-yl)oxazole-4-carboxamide;

(R)—N-(2-(3-(3-Chloro-4-cyano-5-fluorophenyl)-1H-pyrazol-1-yl)propyl)-2-(2-hydroxypropan-2-yl)oxazole-4-carboxamide;

(R)—N-(2-(3-(3-Chloro-4-cyano-5-fluorophenyl)-1H-pyrazol-1-yl)propyl)-2-(2-hydroxypropan-2-yl)-1H-imidazole-4-carboxamide;

(S)—N-(1-(3-(3-Chloro-4-cyano-5-fluorophenyl)-1H-pyrazol-1-yl)propan-2-yl)-2-(2,2,2-trifluoroethyl)-1H-imidazole-4-carboxamide;

(S)—N-(1-(3-(3-Chloro-4-cyano-5-fluorophenyl)-1H-pyrazol-1-yl)propan-2-yl)-2-(trifluoromethyl)-1H-imidazole-4-carboxamide;

N—((S)-1-(3-(3-Chloro-4-cyano-5-fluorophenyl)-1H-pyrazol-1-yl)propan-2-yl)-3-((S)-1-hydroxyethyl)-1,2,4-oxadiazole-5-carboxamide;

N—((S)-1-(3-(3-chloro-4-cyano-5-fluorophenyl)-1H-pyrazol-1-yl)propan-2-yl)-3-((R)-1-hydroxyethyl)-1,2,4-oxadiazole-5-carboxamide;

(S)—N-(2-(3-(3-Chloro-4-cyano-5-fluorophenyl)-1H-pyrazol-1-yl)propyl)-3-(2-hydroxypropan-2-yl)-1,2,4-oxadiazole-5-carboxamide;

(S)—N-(1-(3-(3-Chloro-4-cyano-5-fluorophenyl)-1H-pyrazol-1-yl)propan-2-yl)-3-(2-hydroxypropan-2-yl)-1,2,4-oxadiazole-5-carboxamide;

(S)—N-(1-(3-(3-Chloro-4-cyano-5-fluorophenyl)-1H-pyrazol-1-yl)propan-2-yl)-2-cyclopropyl-1H-imidazole-4-carboxamide;

(S)—N$^4$-(1-(3-(3-Chloro-4-cyano-5-fluorophenyl)-1H-pyrazol-1-yl)propan-2-yl)-N$^2$,N$^2$-dimethyl-1H-imidazole-2,4-dicarboxamide;

(S)—N-(1-(3-(3-Chloro-4-cyano-5-fluorophenyl)-1H-pyrazol-1-yl)propan-2-yl)-2-(2-ethoxypropan-2-yl)-1H-imidazole-4-carboxamide;

N—((S)-1-(3-(3-Chloro-4-cyano-5-fluorophenyl)-1H-pyrazol-1-yl)propan-2-yl)-2-(1-ethoxyethyl)-1H-imidazole-4-carboxamide;

(S)—N-(1-(3-(3-Chloro-4-cyano-5-fluorophenyl)-1H-pyrazol-1-yl)propan-2-yl)-2-(2-ethoxypropan-2-yl)oxazole-4-carboxamide;

(S)—N-(1-(3-(3-Chloro-4-cyano-5-fluorophenyl)-1H-pyrazol-1-yl)propan-2-yl)-5-(2-hydroxy-2-methyl propyl)-1H-pyrazole-3-carboxamide;

or a pharmaceutically acceptable salt thereof.

10. A pharmaceutical composition comprising a compound of claim 1 and a pharmaceutically acceptable carrier.

11. A method for the treatment of an androgen receptor dependent cancer, comprising administering to a subject in need thereof a therapeutically effective amount of a compound according to claim 1.

12. The method according to claim 11, wherein the androgen receptor dependent cancer is prostate cancer.

* * * * *

UNITED STATES PATENT AND TRADEMARK OFFICE
CERTIFICATE OF CORRECTION

| | | |
|---|---|---|
| PATENT NO. | : 8,921,378 B2 | Page 1 of 1 |
| APPLICATION NO. | : 14/112727 | |
| DATED | : December 30, 2014 | |
| INVENTOR(S) | : Olli Törmäkangas et al. | |

It is certified that error appears in the above-identified patent and that said Letters Patent is hereby corrected as shown below:

In the Claims

Claim 1, col. 86, line 5, "$R_{24}$ is hydroxy, halogen or $C_{1\text{-}}$ alkoxy;" should read -- $R_{24}$ is hydroxy, halogen or $C_{1\text{-}7}$ alkoxy; --.

Signed and Sealed this
Twenty-first Day of April, 2015

Michelle K. Lee
*Director of the United States Patent and Trademark Office*

UNITED STATES PATENT AND TRADEMARK OFFICE
CERTIFICATE OF CORRECTION

PATENT NO.           : 8,921,378 B2
APPLICATION NO.      : 14/112727
DATED                : December 30, 2014
INVENTOR(S)          : Olli Törmäkangas et al.

Page 1 of 1

It is certified that error appears in the above-identified patent and that said Letters Patent is hereby corrected as shown below:

In the Claims

Claim 1, col. 85, line 12, "$R_X$ is hydrogen or halogen;" should read -- $R_Z$ is hydrogen or halogen; --.

Claim 1, col. 86, line 7, "ring B is chosen from any one of the following groups" should read -- ring B is chosen from the following groups --.

Claim 1, col. 89, line 51, delete the "." at the end of structure (45').

Claim 6, col. 91, line 40, "ring contains comprises" should read -- ring comprises --.

Claim 8, col. 93, lines 48-49, "-1'-methyl-1'1H-1,4'-" should read -- -1'-methyl-1'H-1,4'- --.

Claim 9, col. 95, lines 17-18, "methyl propyl" should read -- methylpropyl --.

Signed and Sealed this
Twenty-first Day of July, 2015

Michelle K. Lee
*Director of the United States Patent and Trademark Office*